(12) United States Patent
Abe et al.

(10) Patent No.: US 10,131,665 B2
(45) Date of Patent: Nov. 20, 2018

(54) PROCESSES FOR PRODUCING DIAZABICYCLOOCTANE COMPOUNDS

(71) Applicant: MEIJI SEIKA PHARMA CO., LTD., Chuo-ku, Tokyo (JP)

(72) Inventors: Takao Abe, Kanagawa (JP); Takeshi Furuuchi, Kanagawa (JP); Yoshiaki Sakamaki, Kanagawa (JP); Nakako Mitsuhashi, Kanagawa (JP); Yumiko Saito, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/027,956

(22) PCT Filed: Oct. 8, 2014

(86) PCT No.: PCT/JP2014/076875
§ 371 (c)(1),
(2) Date: Apr. 7, 2016

(87) PCT Pub. No.: WO2015/053297
PCT Pub. Date: Apr. 16, 2015

(65) Prior Publication Data
US 2016/0272641 A1    Sep. 22, 2016

(30) Foreign Application Priority Data
Oct. 8, 2013   (JP) .................................. 2013-211242

(51) Int. Cl.
C07D 471/08   (2006.01)
A61K 31/439   (2006.01)
A61K 45/06    (2006.01)

(52) U.S. Cl.
CPC .......... *C07D 471/08* (2013.01); *A61K 31/439* (2013.01); *A61K 45/06* (2013.01); *C07B 2200/13* (2013.01)

(58) Field of Classification Search
None
See application file for complete search history.

(56) References Cited

U.S. PATENT DOCUMENTS 5,286,856 A   2/1994   Kaneko et al.
5,424,069 A   6/1995   Kaneko et al.
(Continued)

FOREIGN PATENT DOCUMENTS

EP   0213595      3/1987
EP   0533149 A1   3/1993
(Continued)

OTHER PUBLICATIONS

Knight: "N-Hydroxysuccinimide" In "Encyclopedia of Reagents for Organic Synthesis", 1995, John Wiley and Sons, vol. 4, pp. 2780-2781.*
(Continued)

*Primary Examiner* — Karl J Puttlitz
(74) *Attorney, Agent, or Firm* — Holtz, Holtz & Volek PC

(57) ABSTRACT

A crystalline form of a diazabicyclooctane derivative represented by the following Formula (VII), and processes for producing the same:

(Continued)

Powder X-ray Diffraction Pattern of Crystalline Form I

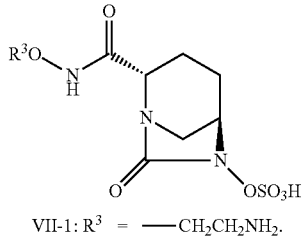

VII-1: $R^3$ = —$CH_2CH_2NH_2$.

17 Claims, 2 Drawing Sheets

(56) References Cited

U.S. PATENT DOCUMENTS

| | | |
|---|---|---|
| 6,111,098 A | 8/2000 | Inoue et al. |
| 7,112,592 B2 | 9/2006 | Lampilas et al. |
| 7,612,087 B2 | 11/2009 | Aszodi et al. |
| 7,638,529 B2 | 12/2009 | Lampilas et al. |
| 7,732,610 B2 | 6/2010 | Lampilas et al. |
| 8,178,554 B2 | 5/2012 | Lampilas et al. |
| 8,288,553 B2 | 10/2012 | Priour et al. |
| 8,471,025 B2 | 6/2013 | Dedhiya et al. |
| 8,487,093 B2 | 7/2013 | Blizzard et al. |
| 8,772,490 B2 | 7/2014 | Abe et al. |
| 8,796,257 B2 | 8/2014 | Maiti et al. |
| 8,822,450 B2 | 9/2014 | Patel et al. |
| 8,829,191 B2 | 9/2014 | Ronsheim et al. |
| 8,835,455 B2 | 9/2014 | Dedhiya et al. |
| 8,877,743 B2 | 11/2014 | Maiti et al. |
| 8,969,566 B2 | 3/2015 | Ronsheim et al. |
| 9,006,230 B2 | 4/2015 | Bhagwat et al. |
| 9,035,062 B2 | 5/2015 | Abe et al. |
| 9,062,053 B2 | 6/2015 | Dedhiya et al. |
| 9,181,250 B2 | 11/2015 | Abe et al. |
| 9,284,273 B2 | 3/2016 | Abe et al. |
| 9,284,314 B2 | 3/2016 | Ronsheim et al. |
| 2003/0199541 A1 | 10/2003 | Lampilas et al. |
| 2003/0220521 A1 | 11/2003 | Reitz et al. |
| 2005/0020572 A1 | 1/2005 | Aszodi et al. |
| 2005/0245505 A1 | 11/2005 | Aszodi et al. |
| 2006/0046995 A1 | 3/2006 | Lampilas et al. |
| 2006/0189652 A1 | 8/2006 | Lampilas et al. |
| 2007/0299108 A1 | 12/2007 | Aszodi et al. |
| 2009/0215747 A1 | 8/2009 | Aszodi et al. |
| 2010/0048528 A1 | 2/2010 | Aszodi et al. |
| 2010/0087648 A1 | 4/2010 | Lampilas et al. |
| 2010/0197928 A1 | 8/2010 | Priour et al. |
| 2011/0021772 A1 | 1/2011 | Lampilas et al. |
| 2011/0046102 A1 | 2/2011 | Ledoussal et al. |
| 2011/0152311 A1 | 6/2011 | Dedhiya et al. |
| 2011/0213147 A1 | 9/2011 | Lampilas et al. |
| 2011/0245254 A1 | 10/2011 | Aszodi et al. |
| 2011/0294777 A1 | 12/2011 | Blizzard et al. |
| 2012/0053350 A1 | 3/2012 | Mangion et al. |
| 2013/0012712 A1 | 1/2013 | Priour et al. |
| 2013/0225554 A1 * | 8/2013 | Maiti .............. C07D 519/00 514/210.21 |
| 2013/0267480 A1 | 10/2013 | Dedhiya et al. |
| 2013/0274475 A1 | 10/2013 | Mangion et al. |
| 2013/0281359 A1 | 10/2013 | Maiti et al. |
| 2014/0221341 A1 | 8/2014 | Maiti et al. |
| 2014/0288051 A1 | 9/2014 | Malti et al. |
| 2015/0141401 A1 | 5/2015 | Abe et al. |
| 2015/0246920 A1 | 9/2015 | Dedhiya et al. |
| 2016/0024090 A1 | 1/2016 | Abe et al. |
| 2016/0264573 A1 | 9/2016 | Abe |
| 2017/0233393 A1 | 8/2017 | Abe et al. |
| 2017/0283415 A1 | 10/2017 | Abe et al. |

FOREIGN PATENT DOCUMENTS

| | | |
|---|---|---|
| GB | 1589317 A | 5/1981 |
| JP | 60019759 B2 | 5/1985 |
| JP | 03074643 B2 | 11/1991 |
| JP | 2767171 B2 | 6/1998 |
| JP | 2843444 B2 | 1/1999 |
| JP | 2004505088 A | 2/2004 |
| JP | 2005518333 A | 6/2005 |
| JP | 2005523897 A | 8/2005 |
| JP | 2010138206 A | 6/2010 |
| JP | 4515704 B2 | 8/2010 |
| JP | 2010539147 A | 12/2010 |
| JP | 2011510012 A | 3/2011 |
| JP | 2011518871 A | 6/2011 |
| JP | 2011207900 A | 10/2011 |
| JP | 2012504593 A | 2/2012 |
| JP | 5038509 B2 | 10/2012 |
| WO | 9529913 A1 | 11/1995 |
| WO | 0210172 A1 | 2/2002 |
| WO | 02100860 A2 | 12/2002 |
| WO | 03063864 A2 | 8/2003 |
| WO | 2009090320 A1 | 7/2009 |
| WO | 2009091856 A2 | 7/2009 |
| WO | 2009133442 A1 | 11/2009 |
| WO | 2010038115 A1 | 4/2010 |
| WO | 2010126820 A2 | 11/2010 |
| WO | 2011042560 A1 | 4/2011 |
| WO | 2012086241 A1 | 6/2012 |
| WO | 2012172368 * | 12/2012 |
| WO | 2012172368 A1 | 12/2012 |
| WO | 2013030735 A1 | 3/2013 |
| WO | 2013038330 A1 | 3/2013 |
| WO | 2013180197 A1 | 12/2013 |
| WO | 2015053297 A1 | 4/2015 |

OTHER PUBLICATIONS

Hans Cerfontain & Bert H, Bakker: In; Leo A. Paquette; "Encyclopedia of Reagents for Organic Synthesis", 1995, John Wiley and Sons, vol. 7, pp. 4699-4702.*
John M. McIntosh: "Sulfur Troxide-1,4-Dioxane" In "Encyclopedia of Reagents for Organic Synthesis", 1995, John Wiley and Sons, vol. 7, pp. 4702-470.*
Thomas T. Tidwell: "Sulfur Trioxide-Pyridine" In: "Encyclopedia of Reagents for Organic Synthesis", 1995, John Wiley and Sons, vol . 7, pp. 4703-4704.*
Partial Supplementary European Search Report dated Feb. 17, 2017 issued in counterpart European Application No. 14852849.0.
Cerfontain, et al., "Sulfur Trioxide", Encyclopedia of Reagents for Organic Synthesis, vol. 7, edited by Leo A. Paquette, 1995, John Wiley and Sons, pp. 4699-4702.
Knight, "N-Hydroxysuccinimide", Encyclopedia of Reagents for Organic Synthesis, vol. 4, Edited by Leo A. Paquette, 1995, John Wiley and Sons, pp. 2780-2781.
McIntosh, "Sulfur Troxide-1, 4-Dioxane", Encyclopedia of Reagents for Organic Synthesis, vol. 7, Edited by Leo A. Paquette, 1995, John Wiley and Sons, pp. 4702-4703.
Tidwell, "Sulfur Trioxide-Pyridine", Encyclopedia of Reagents for Organic Synthesis, vol. 7, Edited by Leo A Paquette, 1995, John Wiley and Sons, pp. 4703-4704.
Brown et al, "Some Active Derivatives of Penicillin", Applied Microbiology 1969, vol. 17, No. 3, pp. 339-343.
Mangion et al, "A Concise Synthesis of a β-Lactamase Inhibitor", Organic Letters, 2011, vol. 13, No. 20, pp. 5480-5483.
Baldwin, et al., "A Novel Entry to Carbenoid Species via β-Ketosulfoxonium Ylides", Journal of the Chemical Society, Chemical Communications, 1993, pp. 1434-1435.
Dolence, et al., "Synthesis and Siderophore Activity of Albomycin-like Peptides Derived from N5-Acetyl-N5-hydroxy-L-ornithine", Journal of Medicinal Chemistry, 1991, vol. 34, No. 3, pp. 956-968.
Freed, et al., "Synthesis of 5-Ketopipecolic Acid from Glutamic Acid", The Journal of Organic Chemistry, Dec. 1960, vol. 25, No. 12, pp. 2105-2107.

(56) References Cited

OTHER PUBLICATIONS

Jung, et al., "Diastereoselective synthesis of (2S,5S)- and (2S,5R)-N-benzyloxycarbonyl-5-hydroxypipecolic acids from trans-4-hydroxy-L-proline", Tetrahedron: Asymmetry 17 (2006), pp. 2479-2486.
King, et al., "The Chemistry of Extractives from Hardwoods. Part III. Baikiain, an Amino-acid Present in Baikiaea plurijuga", Journal of the Chemical Society, 1950, pp. 3590-3597.
Mangion, et al., "Iridium-Catalyzed X-H Insertions of Sulfoxonium Ylides", Organic Letters, 2009, vol. 11, No. 16, pp. 3566-3569.
Pettit, et al., "8-Hydroxy-5-trifluoromethylquinoline", Journal of Chemical Society (1954), 3852-3854.
Witkop, et al., "The Configuration of 5-Hydroxypipecolic Acid from Dates", Journal of the American Chemical Society, Jan. 5, 1957, vol. 79, No. 1, pp. 192-197.
Extended European Search Report (EESR) dated Mar. 24, 2017 issued in counterpart European Application No. 14852849.0.
Caira, "Crystalline Polymorphism of Organic Compounds", Topics in Current Chemistry, Springer, Berlin, DE, vol. 198, Jan. 1, 1998: pp. 163-208.
U.S. Appl. No. 15/532,281: First Named Inventor: Takaya Ogawa; Title: "Production Process of Crystals of Diazabicyclooctane Derivative and Stable Lyophilized Preparation"; filed Jun. 1, 2017.
"Flow of research of Ryuichi Kato and optical isomerism medicine", Time Signal Company, Oct. 1, 1987, 29th volume, No. 10: pp. 2039-2042.
In edited by Chemical Society of Japan, "4th Edition Experimental Science Lecture 1 basic operation I", The Maruzen Co., Ltd: pp. 184-189.
Hirayama, "Organic compound crystal production handbooks", 2008: pp. 17-23, 37-40, 45-51, 57-65.
Nohira, "Agricultural chemicals, medicine, optically active substance, The organic industrial chemistry", Asakura Publishing Co.,Ltd., Jan. 20, 1989, 1st printing: pp. 20, 21.
Asahara Teruzo, "Solvent Handbook", Incorporated Company Kodansha, 1985: pp. 47-51.
Yamanaka, et al., "The Preparation, bioactive and use of an optically active substance, Quarterly Chemistry Survey—Separation of an optical isomer", Japan Scientific Societies Press, Inc., Jun. 10, or 1989, No. 6: pp. 8-9,124, 212-213.
International Search Report (ISR) dated Jan. 20, 2015 issued in International Application No. PCT/JP2014/076875.
Noriaki Hirayama, Yuki Kagobutsu Kessho Sakusei Handbook—Genri to Know-how-, Maruzen Co., Ltd., Jul. 25, 2008, pp. 57-84.
U.S. Appl. No. 15/007,906, Title: "Compounds Useful for Producing an Optically Active Diazabicyclooctane Compound", filed Jan. 27, 2016, First Named Inventor: Takao Abe.
U.S. Appl. No. 15/023,976, Title: "Process for Producing Diazabicyclooctane Derivative and Intermediate Thereof", filed Mar. 22, 2016, First Named Inventor: Takao Abe.
U.S. Appl. No. 14/872,988, Title: "Beta-Lactamase Inhibitor and Process for Preparing the Same", filed Oct. 1, 2015, First Named Inventor: Takao Abe.
Japanese Office Action dated Sep. 12, 2017 which issued in Japanese Application No. 2014-518712.
U.S. Appl. No. 15/532,281, filed Jun. 1, 2017; Confirmation No. 9316.
Korey, et al., "Effects of Excipients on the Crystallization of Pharmaceutical Compounds During Lyophilization", Journal of Parenteral Science & Technology, vol. 43, No. 2, Mar.-Apr. 1989, pp. 80-83.
Rowe, "Handbook of Pharmaceutical Excipients", 5th Edition 2006.
Walker, "The Management of Chemical Process Development in the Pharmaceutical Industry", 2008, John Wiley & Sons, p. 186.
European Office Action dated Jul. 24, 2018 issued in counterpart European Application No. 14852849.0.
Merriam Webster, "Alternate/Alternately", Merriam Webster Online Dictionary, Jul. 17, 2018, XP55493061, <https://www.merriamwebster.com/dictionary/alternately>.
Merriam Webster, "Alternative/Alternatively", Merriam Webster Online Dictionary, Jul. 17, 2018, XP55493064, <https://www.merriam-webster.com/dictionary/alternatively>.

* cited by examiner

Powder X-ray Diffraction Pattern of Crystalline Form I

Powder X-ray Diffraction Pattern of Crystalline Form II

Powder X-ray Diffraction Pattern of Crystalline Form III

PROCESSES FOR PRODUCING DIAZABICYCLOOCTANE COMPOUNDS

TECHNICAL FIELD

The present invention relates to a process for producing crystalline forms of a diazabicyclooctane derivative represented by Formula (VII), particularly Formula (VII-1).

BACKGROUND ART

Japanese Patent No. 4515704 (Patent Document 1) indicates a novel heterocyclic compound, a production process thereof, and the use thereof as a pharmaceutical agent, and discloses as an example of a typical compound thereof sodium trans-7-oxo-6-(sulfooxy)-1,6-diazabicyclo [3.2.1]octane-2-carboxamide (NXL104). Production processes of a specific piperidine derivative as an intermediate are also indicated in Japanese Unexamined Patent Publication No. 2010-138206 (Patent Document 2) and Japanese Unexamined Patent Application Publication (Translation of PCT Application) No. 2010-539147 (Patent Document 3), while a production process of NXL104 and crystalline forms thereof is disclosed in International Publication No. WO 2011/042560 (Patent Document 4).

In addition, Japanese Patent No. 5038509 (Patent Document 5) indicates (2S,5R)-7-oxo-N-(piperidin-4-yl)-6-(sulfooxy)-1,6-diazabicyclo[3.2.1]octane-2-carboxamide (MK7655), while a production process of a specific piperidine derivative and MK7655 is disclosed in Japanese Unexamined Patent Publication No. 2011-207900 (Patent Document 6) and International Publication No. WO 2010/126820 (Patent Document 7).

The inventors of the present invention also disclosed a novel diazabicyclooctane derivative represented by the following Formula (VII) in Japanese Patent Application No. 2012-122603 (Patent Document 8):

[Chemical Formula 1]

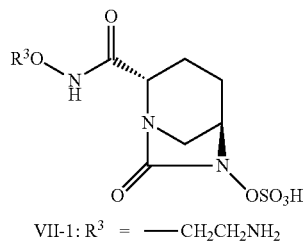

VII-1: $R^3$ = —$CH_2CH_2NH_2$ (wherein $R^3$ is same as will be subsequently described).

PRIOR ART DOCUMENTS

Patent Documents

Patent Document 1: Japanese Patent No. 4515704 specification
Patent Document 2: Japanese Unexamined Patent Publication No. 2010-138206 specification
Patent Document 3: Japanese Unexamined Patent Application Publication (Translation of PCT Application) No. 2010-539147
Patent Document 4: International Publication No. WO 2011/042560
Patent Document 5: Japanese Patent No. 5038509 specification
Patent Document 6: Japanese Unexamined Patent Publication No. 2011-207900 specification
Patent Document 7: International Publication No. WO 2010/126820
Patent Document 8: Japanese Patent Application No. 2012-122603 specification

SUMMARY OF THE INVENTION

Problems to be Solved by the Invention

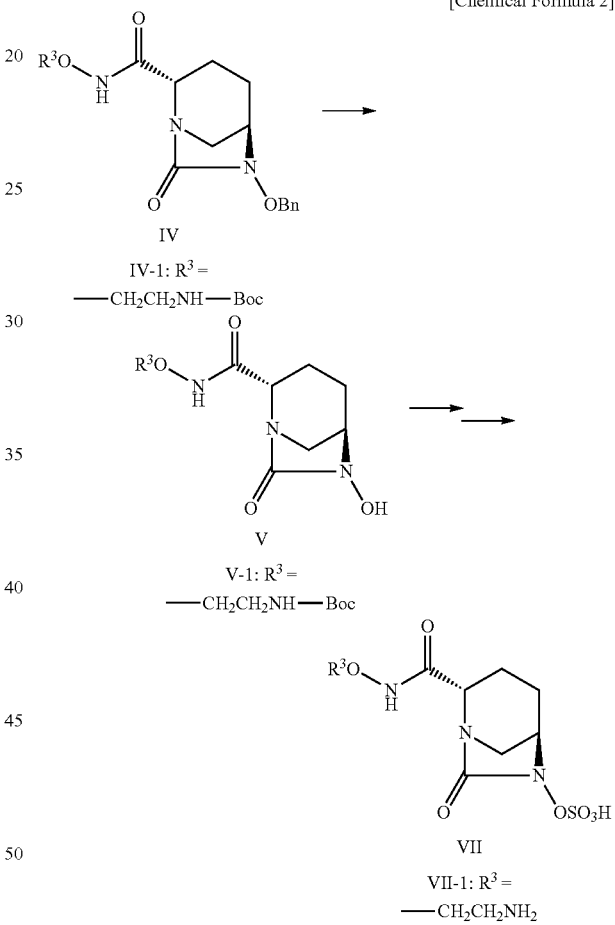

Scheme 1

[Chemical Formula 2]

(In the above Formulas, $R^3$ is same as will be subsequently described, OBn is benzyloxy and Boc is tert-butoxycarbonyl.)

During the course of examining industrialization of (2S, 5R)—N-(2-aminoethoxy)-7-oxo-6-(sulfooxy)-1,6-diazabicyclo[3.2.1]octane-2-carboxamide represented by the aforementioned Formula (VII), particularly Formula (VII-1), various problems relating to production were indicated, such as 1) the need to provide the compound in a stable crystalline form due to the handling difficulty during production of the amorphous active pharmaceutical ingredient (API), particularly the lyophilized product, and the difficulty in ensuring stability; 2) the need to isolate the crude active pharmaceutical ingredient containing an acid obtained after deprotecting the protecting group in the side chain $R^3ONHC(=O)$— group and to establish a procedure for adjusting to a stable pH range; 3) the need to improve yield and to avoid contamination with byproduct by controlling overreaction that causes the side chain $R^3ONHC(=O)$— group to also be sulfated during sulfation of a compound represented by Formula (V); 4) being unable to ignore isolation loss in addition to instability in solution state, particularly instability during evaporation of the reaction solvent to concentrate the compound represented by the aforementioned Formula (V); and 5) unsatisfactory yield of the compound represented by the aforementioned Formula (IV). In particular, the step from isolation and pH adjustment of the crude compound represented by Formula (VII-1-CR) containing an acid to crystallization of the compound represented by Formula (VII-1) was extremely difficult due to complex factors in the effects of instability and high solubility of compound, decomposition products and contaminants.

Means for Solving the Problems

The inventors conducted detailed studies on a process for producing the compound represented by the aforementioned Formula (VII), and established a series of production processes for providing a highly pure solution of the compound represented by Formula (VII) that does not affect crystallization of the compound represented by Formula (VII), as well as a process for producing highly stable crystalline forms.

Namely, (1) the present invention relates to a process for producing a compound represented by the following Formula (VII):

[Chemical Formula 3]

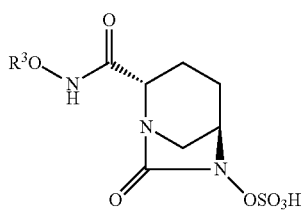

VII comprising: reacting a compound represented by the following Formula (III):

[Chemical Formula 4]

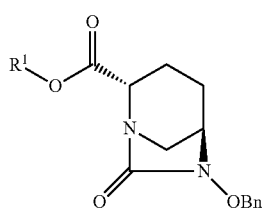

III with a compound: $R^3ONH_2$ to obtain a compound represented by the following Formula (IV):

[Chemical Formula 5]

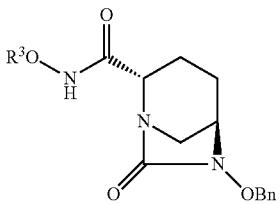

IV treating with a palladium carbon catalyst in a hydrogen atmosphere, simultaneously or consecutively subjecting to a sulfation reaction using sulfur trioxide-trimethylamine complex in the presence of a catalytic amount of base in a hydrous solvent and treating with tetrabutylammonium hydrogensulfate to obtain a compound represented by the following Formula (VI):

[Chemical Formula 6]

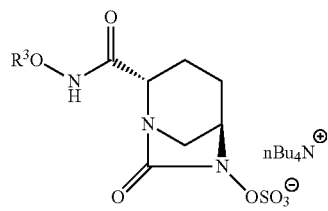

VI followed by, in a case where the $R^3ONHC(=O)$— side chain has a protecting group, removing the protecting group with an acid, and precipitating a crude product by adding a poor solvent to the reaction solution to obtain a crude compound represented by the following Formula (VII-CR):

[Chemical Formula 7]

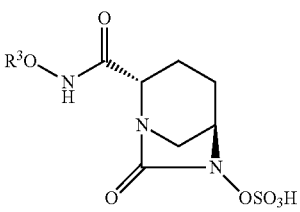

VII-CR (in each of the above formulas, OBn is benzyloxy, $R^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2.6}$]dec-8-en-4-yl, $R^3$ is $C_{1-6}$ alkyl or heterocyclyl. $R^3$ may be modified with 0 to 5 $R^4$, $R^4$ may be consecutively substituted. Here, $R^4$ is $C_{1-6}$ alkyl, heterocyclyl, $R^5(R^6)N$— or a protecting group. $R^5$ and $R^6$ each independently is hydrogen or $C_{1-6}$ alkyl or together forms a heterocyclyl. Further, $R^3$, $R^5$ and $R^6$ can undergo ring closure at an arbitrary position).

followed by alternately adding the crude compound represented by Formula (VII-CR) and an ice-cold buffer to obtain a solution having a pH of 4 to 5.5, concentrating after desalting with a synthetic adsorbent as necessary, adjusting the temperature, seeding as necessary and crystallizing by adding a poor solvent.

In addition, (2) another aspect of the present invention relates to a process for producing a compound represented by the following Formula (IV):

[Chemical Formula 8]

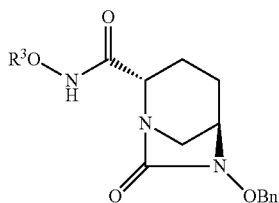

IV comprising: reacting a compound represented by the following Formula (III):

[Chemical Formula 9]

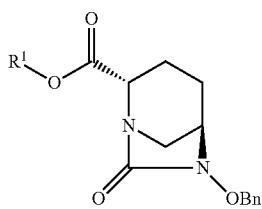

III (in each of the above formulas, $R^1$, $R^3$ and OBn are same as described above) with a compound: $R^3ONH_2$.

In addition, (3) another aspect of the present invention relates to a process for producing a compound represented by the following Formula (VI):

[Chemical Formula 10]

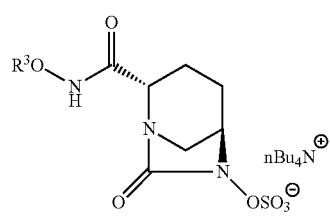

VI comprising: treating a compound represented by the following Formula (IV):

[Chemical Formula 11]

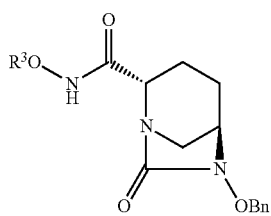

IV (in each of the above formulas, $R^3$ and OBn are same as described above) with a palladium carbon catalyst in a hydrogen atmosphere, simultaneously or consecutively subjecting to a sulfation reaction using sulfur trioxide-trimethylamine complex in the presence of a catalytic amount of base in a hydrous solvent, and treating with tetrabutylammonium hydrogensulfate.

In addition, (4) another aspect of the present invention relates to a process for producing a crude compound represented by the following Formula (VII-CR):

[Chemical Formula 12]

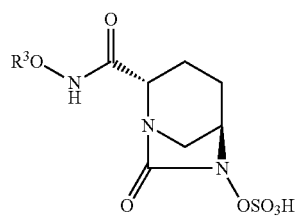

VII-CR comprising: in a case where the $R^3ONHC(=O)-$ side chain has a protecting group, removing the protecting group with an acid from a compound represented by the following Formula (VI):

[Chemical Formula 13]

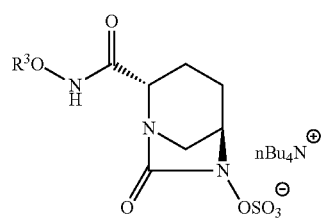

VI (in each of the above formulas, $R^3$ is same as described above)

followed by adding an ester-based poor solvent to the reaction solution to precipitate a crude product.

In addition, (5) another aspect of the present invention relates to a process for producing a compound represented by the following Formula (VII):

[Chemical Formula 14]

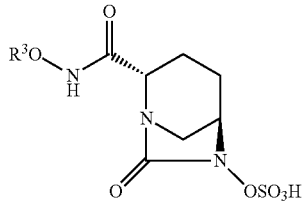

VII comprising: alternately adding a crude compound represented by the following Formula (VII-CR):

[Chemical Formula 15]

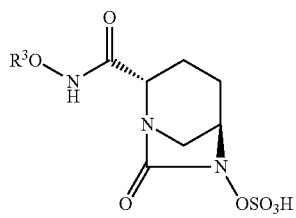

VII-CR (in each of the above formulas, $R^3$ is same as described above)
and an ice-cold buffer to obtain a solution having a pH of 4 to 5.5, concentrating after desalting with a synthetic adsorbent as necessary, adjusting the temperature, seeding as necessary and crystallizing by adding an alcohol-based poor solvent.

In addition, (6) another aspect of the present invention relates to the production process described in any of (1) to (5) above, wherein $R^3$ in the Formulas (IV), (VI), (VII-CR) and (VII) is selected from
2-(tert-butoxycarbonylamino)ethyl;
2-aminoethyl;
2-((tert-butoxycarbonyl)(methyl)amino)ethyl;
2-(methylamino)ethyl;
2-((tert-butoxycarbonyl)(isopropyl)amino)ethyl;
2-(isopropylamino)ethyl;
2-(dimethylamino)ethyl;
(2S)-2-((tert-butoxycarbonyl)amino)propyl;
(2S)-2-(amino)propyl;
(2R)-2-((tert-butoxycarbonyl)amino)propyl;
(2R)-2-(amino)propyl;
3-((tert-butoxycarbonyl)amino)propyl;
3-(amino)propyl;
(2S)-tert-butoxycarbonylazetidin-2-ylmethyl;
(2S)-azetidin-2-ylmethyl;
(2R)-tert-butoxycarbonylpyrrolidin-2-ylmethyl;
(2R)-pyrrolidin-2-ylmethyl;
(3R)-tert-butoxycarbonylpiperidin-3-ylmethyl;
(3R)-piperidin-3-ylmethyl;
(3S)-tert-butoxycarbonylpyrrolidin-3-yl;
(3S)-pyrrolidin-3-yl;
1-(tert-butoxycarbonyl)azetidin-3-yl; and
azetidin-3-yl.

In addition, (7) another aspect of the present invention relates to a process for producing a compound represented by the following Formula (VII-1):

[Chemical Formula 16]

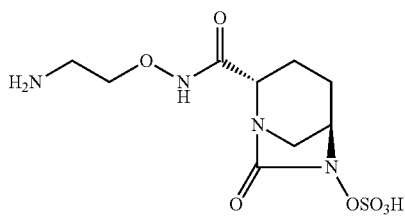

VII-1 comprising: reacting a compound represented by the following Formula (III):

[Chemical Formula 17]

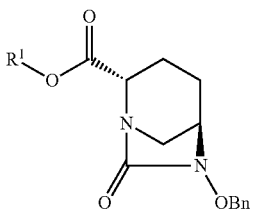

III with tert-butyl 2-(aminooxy)ethylcarbamate in the presence of a base to obtain a compound represented by the following Formula (IV-1):

[Chemical Formula 18]

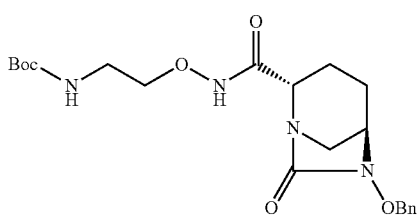

IV-1 followed by treating with a palladium carbon catalyst under a hydrogen atmosphere, simultaneously or consecutively subjecting to a sulfation reaction using sulfur trioxide-trimethylamine catalyst in the presence of a catalytic amount of base in a hydrous solvent, and treating with tetrabutylammonium hydrogensulfate to obtain a compound represented by Formula (VI-1):

[Chemical Formula 19]

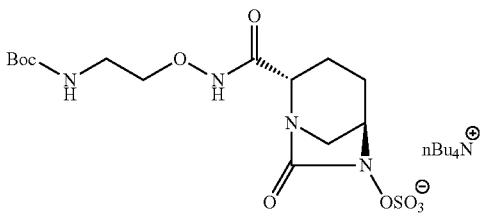

VI-1 followed by removing the tert-butoxycarbonyl (Boc) group with trifluoroacetic acid and dropping ethyl acetate into the reaction solution to precipitate a crude product and obtain a crude compound represented by the following Formula (VII-1-CR):

[Chemical Formula 20]

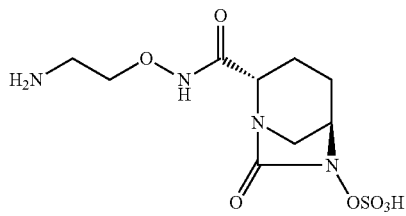

VII-1-CR (in each of the above formulas, $R^1$ and OBn are same as described above) followed by alternately adding the crude compound represented by Formula (VII-1-CR) and an ice-cold phosphate buffer to obtain a solution having a pH of 4 to 5.5, concentrating after desalting with a synthetic adsorbent as necessary, adjusting the temperature, seeding as necessary and adding isopropanol to crystallize.

In addition, (8) another aspect of the present invention relates to a process for producing a compound represented by the following Formula (IV-1):

[Chemical Formula 21]

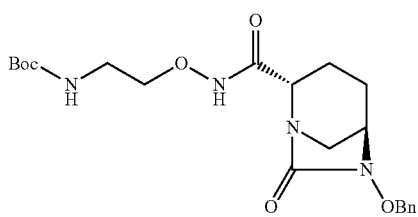

IV-1 comprising: reacting a compound represented by the following Formula (III):

[Chemical Formula 22]

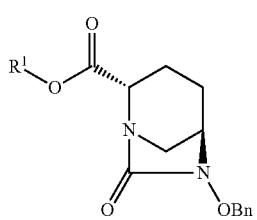

III (in each of the above formulas, $R^1$ and OBn are same as described above) with tert-butyl 2-(aminooxy)ethylcarbamate in the presence of a base.

In addition, (9) another aspect of the present invention relates to a process for producing a compound represented by the following Formula (VI-1):

[Chemical Formula 23]

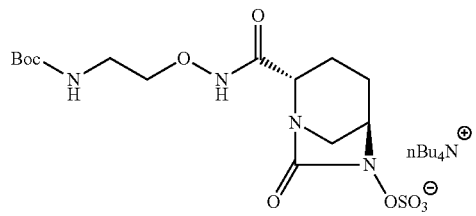

VI-1 comprising: treating a compound represented by the following Formula (IV-1):

[Chemical Formula 24]

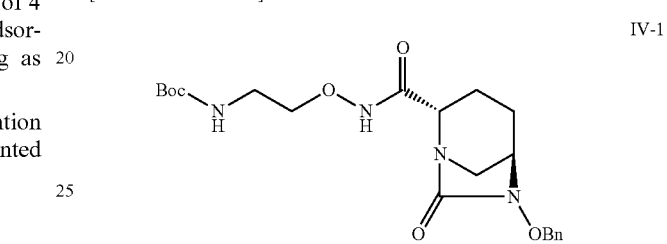

IV-1

(in each of the above formulas, OBn is same as described above with a palladium carbon catalyst under a hydrogen atmosphere, simultaneously or consecutively subjecting to a sulfation reaction using sulfur trioxide-trimethylamine complex in the presence of a catalytic amount of base in a hydrous solvent, and treating with tetrabutylammonium hydrogensulfate.

In addition, (10) another aspect of the present invention relates to a process for producing a crude compound represented by the following Formula (VII-1-CR):

[Chemical Formula 25]

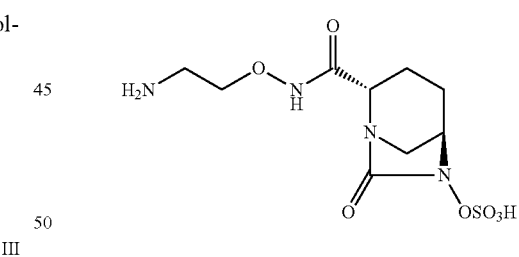

VII-1-CR comprising: removing the tert-butoxycarbonyl (Boc) group with trifluoroacetic acid from a compound represented by the following Formula (VI-1):

[Chemical Formula 26]

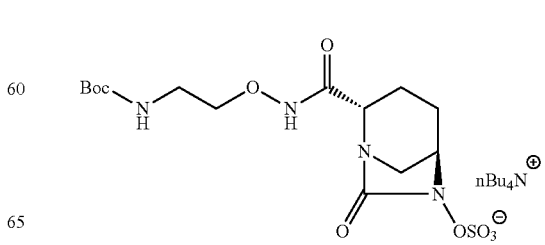

VI-1 followed by dropping ethyl acetate into the reaction solution to precipitate a crude product.

In addition, (11) another aspect of the present invention relates to a process for producing a compound represented by the following Formula (VII-1):

[Chemical Formula 27]

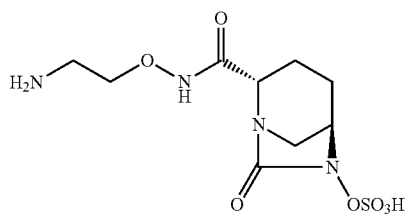

VII-1 comprising: alternately adding a crude compound represented by the following Formula (VII-1-CR):

[Chemical Formula 28]

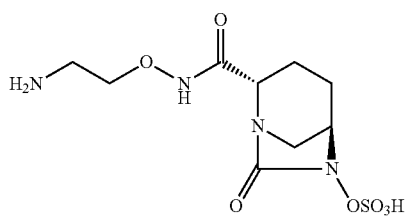

VII-1-CR and an ice-cold phosphate buffer to obtain a solution having a pH of 4 to 5.5, concentrating after desalting with a synthetic adsorbent as necessary, and adjusting the temperature followed by seeding as necessary and adding isopropanol to crystallize.

In addition, (12) another aspect of the present invention relates to a crystalline form I of a compound represented by Formula (VII-1):

[Chemical Formula 29]

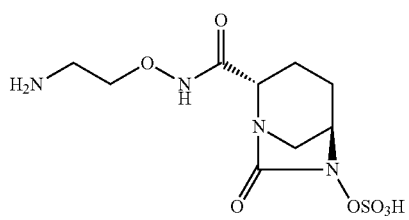

VII-1 having characteristic peaks appearing at lattice spacing (d) of 7.34, 5.66, 5.53, 5.30, 5.02, 4.66, 4.37, 4.28, 4.06, 3.68, 3.62, 3.47, 3.36, 3.30, 3.16, 3.11, 3.03, 2.99 and 2.50 Å in the powder X-ray diffraction pattern.

In addition, (13) another aspect of the present invention relates to the process described in any of (1) to (11) for producing the crystalline form I described in (12).

In addition, (14) another aspect of the present invention relates to a process for producing the crystalline form I described in (12), comprising: adjusting the temperature of a solution of the compound represented by Formula (VII-1) between 20 to 25° C., seeding with a crystalline form I and stirring, followed by further adding isopropanol.

In addition, (15) another aspect of the present invention relates to a use of the crystalline form I described in (12) for producing a pharmaceutical composition optionally comprising a pharmaceutically acceptable carrier.

In addition, (16) another aspect of the present invention relates to a use of the crystalline form I described in (12) for producing a pharmaceutical composition comprising a β-lactam antibiotic selected from the group consisting of ampicillin, amoxicillin, piperacillin, ticarcillin, flomoxef, cefotaxime, ceftriaxone, ceftazidime, cefepime, ceftaroline, ceftolozane, imipenem, meropenem, biapenem, dorinenem, ertapenem and aztreonam, and optionally a pharmaceutically acceptable carrier.

In addition, (17) another aspect of the present invention relates to a crystalline form II of a compound represented by Formula (VII-1):

[Chemical Formula 30]

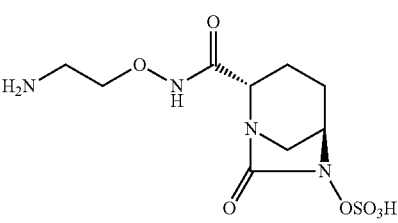

VII-1 having characteristic peaks appearing at lattice spacing (d) of 9.46, 5.62, 5.23, 5.10, 5.00, 4.91, 4.67, 4.45, 4.29, 3.96, 3.78, 3.71, 3.52, 3.24, 3.18, 3.10, 3.02, 2.88, 2.81, 2.77, 2.67, 2.50 and 2.45 Å in the powder X-ray diffraction pattern.

In addition, (18) another aspect of the present invention relates to the process described in any of (1) to (11) for producing the crystalline form II described in (17).

In addition, (19) another aspect of the present invention relates to a process for producing the crystalline form II described in (17), comprising: adjusting the temperature of a solution of the compound represented by Formula (VII-1) between 10 to 15° C., adding isopropanol and stirring.

In addition, (20) another aspect of the present invention relates to a use of the crystalline form II described in (17) for producing a pharmaceutical composition optionally comprising a pharmaceutically acceptable carrier.

In addition, (21) another aspect of the present invention relates to a use of the crystalline form II described in (17) for producing a pharmaceutical composition comprising a β-lactam antibiotic selected from the group consisting of ampicillin, amoxicillin, piperacillin, ticarcillin, flomoxef, cefotaxime, ceftriaxone, ceftazidime, cefepime, ceftaroline, ceftolozane, imipenem, meropenem, biapenem, doripenem, ertapenem and aztreonam, and optionally a pharmaceutically acceptable carrier.

In addition, (22) another aspect of the present invention relates to a crystalline form III of a compound represented by Formula (VII-1):

[Chemical Formula 31]

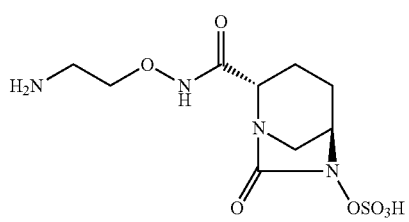

VII-1 having characteristic peaks appearing at lattice spacing (d) of 8.32, 6.10, 5.98, 5.51, 5.16, 5.07, 4.85, 4.70, 4.61, 4.35, 4.20, 4.06, 4.00, 3.95, 3.77, 3.73, 3.65, 3.42, 3.39, 3.36, 3.26, 3.23, 3.13, 3.09, 2.99, 2.81 and 2.52 Å in the powder X-ray diffraction pattern.

In addition, (23) another aspect of the present invention relates to the process described in any of (1) to (11) for producing the crystalline form III described in (22).

In addition, (24) another aspect of the present invention relates to a process for producing the crystalline form III described in (22), comprising: adjusting the temperature of a solution of the compound represented by Formula (VII-1) between 20 to 25° C., seeding with a crystalline form III, adding isopropanol and stirring.

In addition, (25) another aspect of the present invention relates to a use of the crystalline form III described in (22) for producing a pharmaceutical composition optionally comprising a pharmaceutically acceptable carrier.

In addition, (26) another aspect of the present invention relates to a use of the crystalline form III described in (22) for producing a pharmaceutical composition comprising a β-lactam antibiotic selected from the group consisting of ampicillin, amoxicillin, piperacillin, ticarcillin, flomoxef, cefotaxime, ceftriaxone, ceftazidime, cefepime, ceftaroline, ceftolozane, imipenem, meropenem, biapenem, doripenem, ertapenem and aztreonam, and optionally comprising a pharmaceutically acceptable carrier.

In addition, (27) another aspect of the present invention relates to a crystalline form IV of a compound represented by Formula (VII-1):

[Chemical Formula 32]

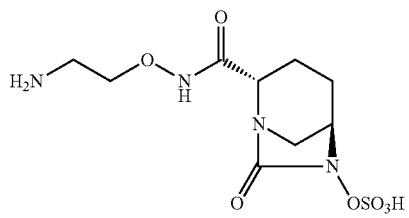

VII-1 having characteristic peaks appearing at lattice spacing (d) of 7.88, 6.41, 5.20, 4.67, 4.50, 4.02, 3.81, 3.75, 3.70, 3.62, 3.38, 3.23, 3.20 and 2.74 Å in the powder X-ray diffraction pattern.

In addition, (28) another aspect of the present invention relates to the process described in any of (1) to (11) for producing the crystalline form IV described in (27).

In addition, (29) another aspect of the present invention relates to a process for producing the crystalline form IV described in (27), comprising: adjusting the temperature of a solution of the compound represented by the Formula (VII-1) between 20 to 25° C., adding methanol, and stirring.

In addition, (30) another aspect of the present invention relates to a process for producing the crystalline form IV described in (27), comprising: stirring the crystalline form I, II or III described in (12), (17) or (22) in methanol, ethanol or isopropanol.

In addition, (31) another aspect of the present invention relates to a use of the crystalline form IV described in (27) for producing a pharmaceutical composition optionally comprising a pharmaceutically acceptable carrier.

In addition, (32) another aspect of the present invention relates to a use of the crystalline form IV described in (27) for producing a pharmaceutical composition comprising a β-lactam antibiotic selected from the group consisting of ampicillin, amoxicillin, piperacillin, ticarcillin, flomoxef, cefotaxime, ceftriaxone, ceftazidime, cefepime, ceftaroline, ceftolozane, imipenem, meropenem, biapenem, doripenem, ertapenem and aztreonam, and optionally comprising a pharmaceutically acceptable carrier.

In addition, (33) another aspect of the present invention relates to a use of a mixture of the crystalline forms I, II, III or IV described in (12), (17), (22) or (27) for producing a pharmaceutical composition optionally comprising a pharmaceutically acceptable carrier.

In addition, (34) another aspect of the present invention relates to a use of a mixture of the crystalline form I, II, III or IV described in (12), (17), (22) or (27) for producing a pharmaceutical composition comprising a β-lactam antibiotic selected from the group consisting of ampicillin, amoxicillin, piperacillin, ticarcillin, flomoxef, cefotaxime, ceftriaxone, ceftazidime, cefepime, ceftaroline, ceftolozane, imipenem, meropenem, biapenem, doripenem, ertapenem and aztreonam, and optionally a pharmaceutically acceptable carrier.

Effects of the Invention

According to the series of production processes of the present invention, crystalline forms of a compound represented by the aforementioned Formula (VII), particularly a compound represented by Formula (VII-1) and crystalline forms thereof having favorable stability, can be produced with good reproducibility and high yield.

Scheme 2

[Chemical Formula 33]

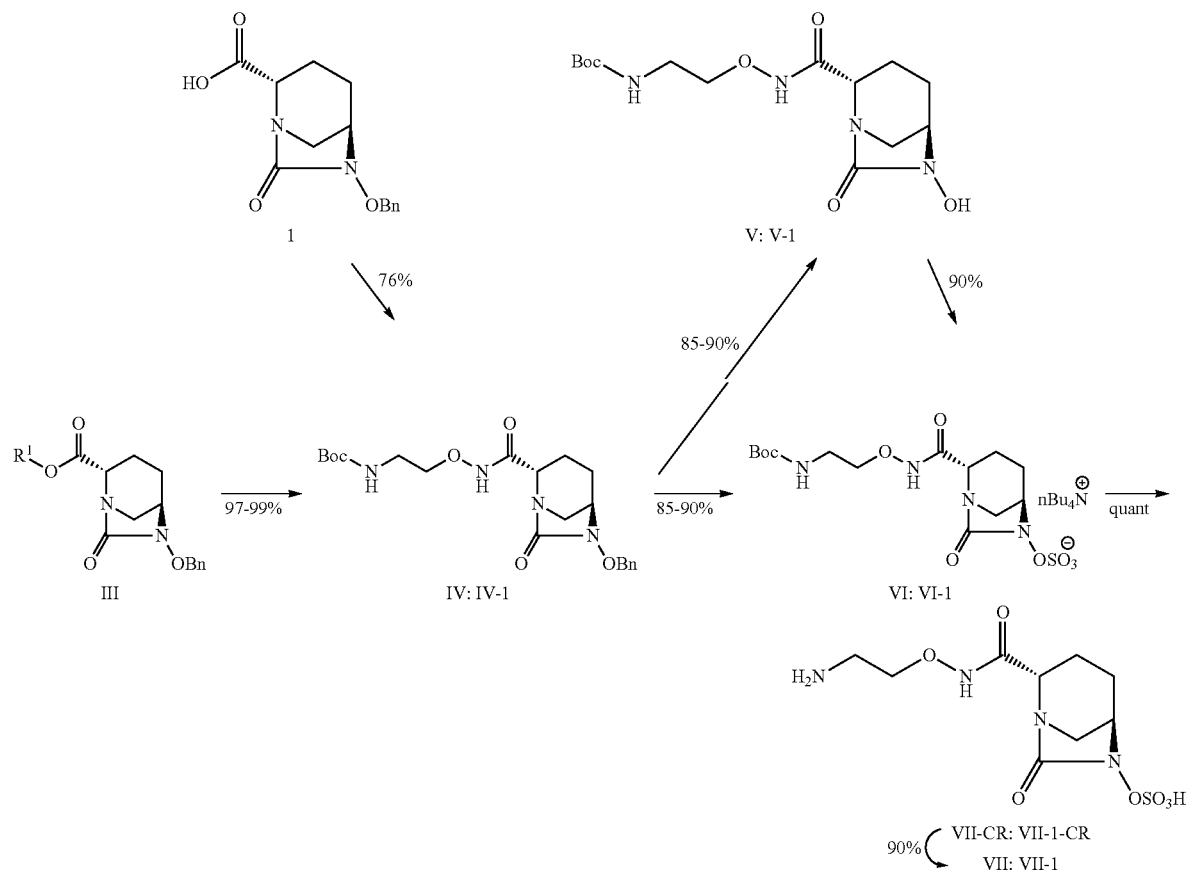

Although there were factors that directly impaired crystallization of the compound represented by Formula (VII) and that was caused from decomposition of the compound represented by Formula (VII) during adjustment of pH and from carrying over of degraded products in a series of steps to the next step, decomposition of the compound represented by Formula (VII) is completely controlled, and a solution with high purity of the compound represented by Formula (VII) that is able to be crystallized can be obtained at high yield by employing processes for producing a compound represented by Formula (VI) and a compound represented by Formula (VII-CR) established in the present invention, and further employing a series of steps for isolation, neutralization and desalting of the compound represented by Formula (VII-CR) containing an acid.

A compound represented by the aforementioned Formula (III), particularly a compound in which $R^1$ represents 2,5-dioxopyrrolidin-1-yl, 1,3-dioxo-3a,4,7,7a-tetrahydro-1H-isoindol-2(3H)-yl, 1,3-dioxohexahydro-1H-isoindol-2 (3H)-yl or 3,5-dioxo-4-azatricyclo[5.2.1.0$^{2.6}$]dec-8-en-4-yl, yields a compound represented by Formula (IV) at a higher purity and a higher yield as compared with synthesizing from the aforementioned Formula (1).

Although the yield of a compound represented by the aforementioned Formula (V) that is unstable in a solution tended to decrease accompanying an increase of the production scale, the formation of decomposed products during concentration of a compound represented by Formula (V), decreases in yield caused by isolation loss, and contamination by overreacted products in the sulfation step are avoided by deriving a compound represented by Formula (VI) from a compound represented by Formula (IV) by either a one-pot or sequential reaction. Although an alcohol-based solvent is superior for that of the debenzylation reaction of the compound represented by Formula (IV), sulfur trioxide-pyridine complex, which is typically used in the subsequent sulfation step, is deactivated in alcohol-based solvents and therefore cannot be applied. The sulfur trioxide-trimethylamine complex found in the present invention exhibits superior stability in alcohol-based solvents, and enables the sulfation reaction to be carried out in one-pot or sequentially.

In the step for producing the compound represented by Formula (VII-CR), a compound represented by Formula (VII-CR) can be produced with favorable reproducibility in the form of an easily handled solid having low hygroscopicity and few decomposed-products by precipitating with a poor solvent such as an ester-based solvent or an ether-based solvent having low hygroscopicity, particularly versatile ethyl acetate, to the reaction solution. The contamination ratio of acid components having an effect on the neutralization step can be controlled within the allowable range for the subsequent step between 10 to 30 mol % by washing a wet solid, thereby making it possible to maintain a high level of purity and demonstrate an HPLC area ratio of 99% or more.

Crystal transformation in the polymorphism of the compound represented by Formula (VII-1) obtained in the present invention are not observed in a stability test carried out at 40° C. in the solid state or in stirring the suspension in a hydrous solvent for a long time. When crystalline form III of the compound represented by Formula (VII-1) was subjected to an XRD-DSC experiment, heated to 160° C. at 60% RH, and then allowed to cool on standing to 63° C., the crystalline form changed to anhydrous crystalline form over about 145° C., and then returned to the crystalline form III below about 90° C. after cooling. On the basis of these findings, a crystalline form of a compound represented by Formula (VII-1), particularly the crystalline form III constitutes a stable form under ordinary conditions.

When the changes over time of the water content, total amounts of related substances and content of the amorphous form and the crystalline forms I, II, III and IV of the compound represented by Formula (VII-1) were simultaneously compared under conditions of 40° C. (75% RH), as shown in the following Table 1, in contrast to the total amount of related substances of the amorphous form being 0.5% at the start of the experiment, the amount subsequently increased considerably to, 6.6% after 1 month and 12.3% after 3 months, and also in contrast to the content being 99.4% at the start, it decreased to 93.3% after 1 month and 87.5% after 3 months. On the other hand, in contrast to the total amounts of related substances of the crystalline forms I, II, III and IV being 0.0-0.1% at the start of the experiment, the amounts are unchanged demonstrating 0.0% after 1 month and 0.0-0.5% after 3 months, and also in contrast to the content being 99.8-99.9% at the start of the experiment, it remained unchanged and stable, demonstrating 99.8-100.0% after 1 month and 99.3-99.9% after 3 months, and also in contrast to the water content of the crystalline forms I, II, III and IV being 5.3-5.7% and 0.1% at the start of the experiment, it remained unchanged and stable, demonstrating 5.5-5.9% and 0.1 after 3 months and 1 month.

Moreover, when contact stability of the crystalline form III in a bulk drug packaging container was observed over time as shown in Table 2 and Table 3, in contrast to the content, the total amount of related substances and water content at the start of the experiment being 99.9%, 0.09% and 5.20%, respectively, after 3 months at 40° C. (75% RH), the values were 99.9%, 0.06% and 5.29%, respectively, and after 1 month at 60° C., the values were 99.9%, 0.04% and 5.08%, respectively, demonstrating that the crystals were unchanged and remained stable.

TABLE 2

Inner package: a low-density polyethylene bag, Nylon tie band
Outer package: an aluminum laminated bag, heat-sealed
Storage conditions: 40° C./75% RH

| Test Parameters | At start | 1 month | 2 months | 3 months |
|---|---|---|---|---|
| Total amount of related substances (%) | 0.09 | 0.07 | 0.04 | 0.06 |
| Water content (%) | 5.20 | 5.51 | 5.27 | 5.29 |
| Content (%) | 99.9 | 99.9 | 99.9 | 99.9 |

TABLE 3

Inner package: a low-density polyethylene bag, Nylon tie band
Outer package: an aluminum laminated bag, heat-sealed
Storage conditions: 60° C.

| Test Parameters | At start | 2 weeks | 4 weeks |
|---|---|---|---|
| Total amount of related substances (%) | 0.09 | 0.02 | 0.04 |
| Water content (%) | 5.20 | 5.20 | 5.08 |
| Content (%) | 99.9 | 99.9 | 99.9 |

TABLE 1

Figure 1:
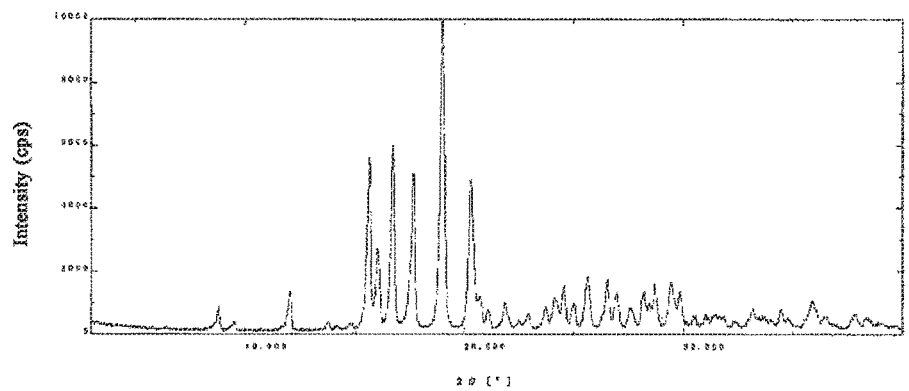
FIG. 1 shows a powder X-ray diffraction pattern of crystalline form I.

Storage conditions: 40° C./75% RH, airtight container

| Crystalline form | At start | | | 1 month | | | 3 months | | |
|---|---|---|---|---|---|---|---|---|---|
| | Water content (%) | Total amount of related substances (%) | Content (%) | Water content (%) | Total amount of related substances (%) | Content (%) | Water content (%) | Total amount of related substances (%) | Content (%) |
| Amorphous form | 1.3 | 0.5 | 99.4 | 3.3 | 6.6 | 93.3 | 3.8 | 12.3 | 87.5 |
| Crystalline form I | 5.4 | 0.1 | 99.9 | 5.4 | 0.0 | 99.9 | 5.6 | 0.1 | 99.8 |
| Crystalline form II | 5.7 | 0.1 | 99.8 | 5.6 | 0.0 | 99.8 | 5.9 | 0.5 | 99.3 |
| Crystalline form III | 5.3 | 0.0 | 99.9 | 5.3 | 0.0 | 100.0 | 5.5 | 0.0 | 99.9 |
| Crystalline form IV | 0.1 | 0.0 | 99.9 | 0.1 | 0.0 | 99.8 | NT | NT | NT |

MODE FOR CARRYING OUT THE INVENTION

As has been previously described, the present invention provides highly stable crystalline forms of a compound represented by the aforementioned Formula (VII), particularly a compound represented by Formula (VII-1), and a production process thereof.

[Chemical Formula 34]

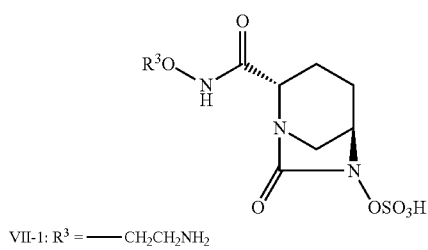

VII

VII-1: R³ = ―CH₂CH₂NH₂

(In Formula (VII) above, $R^3$ is $C_{1-6}$ alkyl or heterocyclyl. $R^3$ may be modified with 0 to 5 $R^4$, $R^4$ may be consecutively substituted. Here, $R^4$ is $C_{1-6}$ alkyl, heterocyclyl, $R^5(R^6)N$— or a protecting group. $R^5$ and $R^6$ each independently is hydrogen or $C_{1-6}$ alkyl or together forms a heterocyclyl. Further, $R^3$, $R^5$ and $R^6$ can undergo ring closure at an arbitrary position.)

The following provides a detailed explanation of the process of the present invention for producing a crystalline form of the compound represented by Formula (VII), but the present invention is not limited to the scope of the indicated specific examples thereof.

"$C_{1-6}$ alkyl" refers to an alkyl group having 1 to 6 carbon atoms, which may be linear, branched or cyclic.

"Heterocyclyl" refers to a 3- to 7-membered monocyclic heterocyclic saturated ring or non-aromatic ring having a total of 1 to 3 heteroatoms selected from a nitrogen atom, oxygen atom and sulfur atom as ring constituents thereof.

"$R^5(R^6)N$—" refers to an amino, namely an amino, mono-$C_{1-6}$ alkyl amino or di-$C_{1-6}$ alkylamino substituted with $R^5$ and $R^6$, or a heterocyclyl formed by $R^5$ and $R^6$ together with a nitrogen atom.

"Modified" refers to a hydrogen in $R^3$ being substituted with or connected to $R^4$.

"$R^3$ may be modified with 0 to 5 $R^4$, $R^4$ may be consecutively substituted" means that $R^4$ that modifies $R^3$ may be further modified with $R^4$, and examples thereof include $R^3$—$(R^4)_{0-5}$, $R^3$—$(R^4$—$R^4_{0-4})$, $R^3$—$(R^4$—$R^4_{0-3})_2$, $R^3$—$(R^4$—$R^4_{0-2})_3$ and $R^3$—$(R^4$—$R^4_{0-1})_4$.

Specific examples of a "protecting group" include carbamate-type protecting groups and trialkylsilyl groups that are protecting groups of amino groups and hydroxyl groups as described in Protective Groups in Organic Synthesis (T. W. Greene et al., Wiley, New York (1999)), and preferable examples thereof include triisopropylsilyl (TIPS), tert-butyldimethylsilyl (TBDMS or TBS), tert-butoxycarbonyl (Boc), trimethylsilylethoxycarbonyl (Teoc), 4-methoxybenzyloxycarbonyl (PMZ, Moz) and diphenylmethoxycarbonyl.

Specific examples of "$C_{1-6}$ alkyl" include linear or branched $C_{1-6}$ alkyl groups such as a methyl, ethyl, propyl, isopropyl, butyl, tert-butyl, s-butyl, isobutyl, pentyl, 1,1-dimethylpropyl, 1,2-dimethylpropyl, neopentyl, 1-methylbutyl, 2-methylbutyl, isopentyl or hexyl group; $C_{3-6}$ cycloalkyl groups such as a cyclopropyl, cyclobutyl, cyclopentyl or cyclohexyl group; and methyl groups substituted with a $C_{3-5}$ cycloalkyl group such as a cyclopropylmethyl, cyclobutylmethyl or cyclopentylmethyl group, and preferably include methyl, ethyl, propyl, isopropyl, butyl, tert-butyl, cyclopropyl, cyclobutyl, cyclopropylmethyl and cyclobutylmethyl groups.

Specific examples of "heterocyclyl" groups include aziridine, oxirane, thiirane, azetidine, oxetane, thietane, pyrrolidine, tetrahydrofuran, tetrahydrothiophene, imidazolidine, oxazolidine, thiazolidine, pyrazolidine, piperidine, tetrahydro-2H-pyran, tetrahydro-2H-thiopyran, hexahydropyridazine, piperazine, morphorine, thiomorphorine, 1,2-oxazolidine, 1,3-oxazolidine, 1,2-oxazinane, 1,3-oxazinane, 1,4-dioxane, 1,2-thiazolidine, 1,3-thiazolidine, 1,2-thiazinane, 1,3-thiazinane, azepane, oxepane, thiepane, 1,4-diazepane, 1,4-oxazepane, 1,4-thiazepane, 1,2,5-triazepane, 1,4,5-oxadiazepane, 1,2,5-oxadiazepane, 1,4,5-thiadiazepane, 1,5,2-dioxazepane, 1,5,2-oxathiazepane, 3,4-dihydro-2H-pyrrole, 4,5-dihydro-1H-pyrazole, 4,5-dihydro-1H-imidazole, 4,5-dihydro-1,2-oxazole, 4,5-dihydro-1,3-oxazole, 4,5-dihydro-1,3-thiazole, 2,3,4,5-tetrahydropyridine, 1,2,3,6-tetrahydropyrazine, 5,6-dihydro-4H-1,2-oxazine and 3,6-dihydro-2-H-1,4-oxazine and preferably include azetidine, pyrrolidine, tetrahydrofuran, piperidine, tetrahydro-2H-pyran, imidazolidine, 1,3-oxazolidine, 1,3-thiazolidine, hexahydropyridazine, piperazine, morphorine, 1,2-oxazinane, azepane, 1,4-diazepane and 1,2-oxazepane. Here, it goes without saying that the aforementioned specific examples include those connected with a protecting group such as a tert-butoxycarbonyl (Boc) group.

Specific examples of "$R^5(R^6)N$—" include amino, methylamino, ethylamino, propylamino, isopropylamino, butylamino, tert-butylamino, s-butylamino, isobutylamino, pentylamino, 1,1-dimethylpropylamino, 1,2-dimethylpropylamino, neopentylamino, 1-methylbutylamino, 2-methylbutylamino, isopentylamino, hexylamino, N,N-dimethylamino, N,N-diethylamino, N,N-dipropylamino, N,N-di(isopropyl)amino, N,N-dibutylamino, N,N-di(tert-butyl)amino, N,N-di(s-butyl)amino, N,N-di(isobutyl)amino, N,N-dipentylamino, N,N-di(1,1-dimethylpropyl)amino, N,N-di(1,2-dimethylpropyl)amino, N,N-di(neopentyl)amino, N,N-di(1-methylbutyl)amino, N,N-di(2-methylbutyl)amino, N,N-di(isopentyl)amino and N,N-di(hexyl)amino and preferably include amino, methylamino, ethylamino, propylamino, isopropylamino, N,N-dimethylamino and N,N-diethylamino. Here, it goes without saying that the aforementioned specific examples include those connected with a protecting group such as a tert-butoxycarbonyl (Boc)group.

Specific examples of groups formed in the case of $R^5$ and $R^6$ of $R^5(R^6)N$— connecting to form a heterocyclyl group include azetidin-1-yl, pyrrolidin-1-yl, piperidin-1-yl and azepan-1-yl groups. It goes without saying that the aforementioned specific examples include those connected with a protecting group such as a tert-butoxycarbonyl (Boc).

"$R^3$, $R^5$ and $R^6$ can undergo ring closure at an arbitrary position" means that, in the case $R^3$ is $C_{1-6}$ alkyl and $R^4$ that modifies $R^3$, namely $R^5$ or $R^6$ contained in $R^5(R^6)N$—, is $C_{1-6}$ alkyl, $R^3$ and $R^5$ or $R^6$ can together form a 3- to 7-membered saturated ring.

Continuing, although specific examples of compounds formed in the case of a substituent defined by $R^4$ modifying a $C_{1-6}$ alkyl or heterocyclyl that forms $R^3O$— are explained by listing even more specific typical examples thereof, it goes without saying that these compounds are not limited to the scope of the indicated specific examples.

Specific examples of an amino group ($H_2N$—) of a typical example of $R^5(R^6)N$— modifying a "$C_{1-6}$ alkyl" include 2-aminoethyl, 2-aminopropyl, 3-aminopropyl, 2-amino-1-methylethyl, 2-aminobutyl, 3-aminobutyl, 4-aminobutyl, 2-amino-1,1-dimethylethyl, 2-amino-1-methylpropyl, or 3-amino-2-methylpropyl. Here, it goes without saying that the aforementioned specific examples include those connected with a protecting group such as a tert-butoxycarbonyl (Boc) group contained in R⁵OCO—.

Specific examples of a methyl group of a typical example of a $C_{1-6}$ alkyl modifying a heterocyclyl include 1-methylazetidine, 3-methylazetidine, 1-methylpyrrolidine, 3-methylpyrrolidine, 1-methylimidazolidine, 3-methyloxazolidine, 1-methylpyrazolidine, 1-methylpiperidine, 4-methylpiperidine, 2-methyltetrahydro-2H-pyran, 4-methyltetrahydro-2H-pyran, 1-methylpiperazine, 1,4-dimethylpiperazine, 4-methylmorpholine, 4-methyl-thiomorpholine, 1-methylazepane, 1-methyl-1,4-diazepane and 1,4-dimethyl-1,4-diazepane. Here, it goes without saying that the aforementioned specific examples include those connected with a protecting group such as a tert-butoxycarbonyl (Boc) group.

Specific examples of an amino group (H₂N—) of a typical example of R⁵(R⁶)N— modifying a heterocyclyl include 3-aminoazetidine, 3-aminopyrrolidine, 3-amino-tetrahydrofuran, 3-amino-tetrahydrothiophene, 4-aminopyrazolidine, 4-aminopiperidine, 4-amino-tetrahydro-2H-pyran, 4-amino-tetrahydro-2H-thiopyran, 4-amino-hexahydropyridazine, 4-amino-1,2-oxazolidine, 4-amino-1,2-oxazinane, 4-aminoazepane, 4-aminooxepane and 6-amino-1,4-diazepane. Here, it goes without saying that the aforementioned specific examples include those connected with a protecting group such as a tert-butoxycarbonyl (Boc) group.

Specific examples of a heterocyclyl modifying a methyl or ethyl of a typical example of a $C_{1-6}$ alkyl include azetidin-2-ylmethyl, azetidin-3-ylmethyl, pyrrolidin-2-ylmethyl, pyrrolidin-3-ylmethyl, tetrahydrofuran-3-ylmethyl, tetrahydrothiophen-3-ylmethyl, pyrazolidin-4-ylmethyl, 1,2-oxazolidin-3-ylmethyl, piperidine-2-ylmethyl, piperidin-3-ylmethyl, piperidin-4-ylmethyl, tetrahydro-2H-pyran-4-ylmethyl, tetrahydro-2H-thiopyran-4-ylmethyl, hexahydropyridazin-4-ylmethyl, piperazin-2-ylmethyl, 1,2-oxazinan-3-ylmethyl, morphorin-2-ylmethyl, morphorin-3-ylmethyl, thiomorphorin-2-ylmethyl, thiomorphorin-3-ylmethyl, azepan-2-ylmethyl, azepan-4-ylmethyl, oxepan-2-ylmethyl, oxepan-4-ylmethyl, 1,4-diazepan-2-ylmethyl, 1,4-diazepan-6-ylmethyl, 2-(azetidin-1-yl)ethyl, 2-(pyrrolidin-1-yl)ethyl, 2-(pyrazolidin-1-yl)ethyl, 2-(piperidin-1-yl)ethyl, 2-(hexahydropyridazine-1-yl)ethyl, 2-(piperazine-1-yl)ethyl, 2-(morpholin-4-yl)ethyl, 2-(thiomorpholin-4-yl)ethyl, 2-(1,2-oxazolidin-2-yl)ethyl, 2-(1,2-oxazinan-2-yl)ethyl, 2-(azepan-1-yl)ethyl, or 2-(1,4-diazepan-1-yl)ethyl. Here, it goes without saying that the aforementioned specific examples include those connected with a protecting group such as a tert-butoxycarbonyl (Boc) group.

Specific examples of compounds represented by chemical Formulas (IV), (VI), (VII-CR) and (VII) provided by the present invention are compounds selected from tert-butyl{2-[({[(2S,5R)-6-benzyloxy-7-oxo-1,6-diazabicyclo[3.2.1]oct-2-yl]carbonyl}amino)oxy]ethyl}carbamate;

tetrabutylammonium tert-butyl{2-[({[(2S,5R)-7-oxo-6-(sulfooxy)-1,6-diazabicyclo[3.2.1]oct-2-yl]carbonyl}amino) oxy]ethyl}carbamate;

(2S,5R)—N-(2-aminoethoxy)-7-oxo-6-(sulfooxy)-1,6-diazabicyclo[3.2.1]octane-2-carboxamide;

tert-butyl{2-[({[(2S,5R)-6-benzyloxy-7-oxo-1,6-diazabicyclo[3.2.1]oct-2-yl]carbonyl}amino)oxy]ethyl}(methyl) carbamate;

tetrabutylammonium tert-butyl{2-[({[(2S,5R)-7-oxo-6-(sulfooxy)-1,6-diazabicyclo[3.2.1]oct-2-yl]carbonyl}amino) oxy]ethyl}(methyl)carbamate;

(2S,5R)—N-[2-(methylamino)ethoxy]-7-oxo-6-(sulfooxy)-1,6-diazabicyclo[3.2.1]octane-2-carboxamide;

tert-butyl{2-[({[(2S,5R)-6-benzyloxy-7-oxo-1,6-diazabicyclo[3.2.1]oct-2-yl]carbonyl}amino)oxy]ethyl}(propan-2-yl)carbamate;

tetrabutylammonium tert-butyl{2-[({[(2S,5R)-7-oxo-6-(sulfooxy)-1,6-diazabicyclo[3.2.1]oct-2-yl]carbonyl}amino) oxy]ethyl}(propan-2-yl)carbamate;

(2S,5R)-7-oxo-N-[2-(propan-2-ylamino)ethoxy]-6-(sulfooxy)-1,6-diazabicyclo[3.2.1]octane-2-carboxamide;

(2S,5R)-6-benzyloxy-N-[2-(dimethylamino)ethoxy]-7-oxo-1,6-diazabicyclo[3.2.1]octane-2-carboxamide;

tetrabutylammonium (2S,5R)—N-[2-(dimethylamino) ethoxy]-7-oxo-6-(sulfooxy)-1,6-diazabicyclo[3.2.1]octane-2-carboxamide;

(2S,5R)—N-[2-(dimethylamino)ethoxy]-7-oxo-6-(sulfooxy)-1,6-diazabicyclo[3.2.1]octane-2-carboxamide;

tert-butyl{(2S)-1-[({[(2S,5R)-6-benzyloxy-7-oxo-1,6-diazabicyclo[3.2.1]oct-2-yl]carbonyl}amino)oxy]propan-2-yl}carbamate;

tetrabutylammonium tert-butyl{(2S)-1-[({[(2S,5R)-7-oxo-6-(sulfooxy)-1,6-diazabicyclo[3.2.1]oct-2-yl] carbonyl}amino)oxy]propan-2-yl}carbamate;

(2S,5R)—N-{[(2S)-2-aminopropyl]oxy}-7-oxo-6-(sulfooxy)-1,6-diazabicyclo[3.2.1]octane-2-carboxamide;

tert-butyl{(2R)-1-[({[(2S,5R)-6-benzyloxy-7-oxo-1,6-diazabicyclo[3.2.1]oct-2-yl]carbonyl}amino)oxy]propan-2-yl}carbamate;

tetrabutylammonium tert-butyl{(2R)-1-[({[(2S,5R)-7-oxo-6-(sulfooxy)-1,6-diazabicyclo[3.2.1]oct-2-yl] carbonyl}amino)oxy]propan-2-yl}carbamate;

(2S,5R)—N-{[(2R)-2-aminopropyl]oxy}-7-oxo-6-(sulfooxy)-1,6-diazabicyclo[3.2.1]octane-2-carboxamide;

tert-butyl{3-[({[(2S,5R)-6-benzyloxy-7-oxo-1,6-diazabicyclo[3.2.1]oct-2-yl]carbonyl}amino)oxy] propyl}carbamate;

tetrabutylammonium tert-butyl {3-[({[(2S,5R)-7-oxo-6-(sulfooxy)-1,6-diazabicyclo[3.2.1]oct-2-yl] carbonyl}amino)oxy]propyl}carbamate, (2S,5R)—N-(3-aminopropoxy)-7-oxo-6-(sulfooxy)-1,6-diazabicyclo[3.2.1]octane-2-carboxamide;

tert-butyl(2S)-2-{[({[(2S,5R)-6-benzyloxy-7-oxo-1,6-diazabicyclo[3.2.1]oct-2-yl]carbonyl}amino)oxy] methyl}azetidine-1-carboxylate;

tetrabutylammonium tert-butyl(2S)-2-{[({[(2S,5R)-7-oxo-6-(sulfooxy)-1,6-diazabicyclo[3.2.1]oct-2-yl] carbonyl}amino)oxy]methyl}azetidine-1-carboxylate;

(2S,5R)—N-[(2S)-azetidin-2-ylmethoxy]-7-oxo-6-(sulfooxy)-1,6-diazabicyclo[3.2.1]octane-2-carboxamide;

tert-butyl(2R)-2-{[({[(2S,5R)-6-benzyloxy-7-oxo-1,6-diazabicyclo[3.2.1]oct-2-yl]carbonyl}amino)oxy] methyl}pyrrolidine-1-carboxylate;

tetrabutylammonium tert-butyl(2R)-2-{[({[(2S,5R)-7-oxo-6-(sulfooxy)-1,6-diazabicyclo[3.2.1]oct-2-yl] carbonyl}amino)oxy]methyl}pyrrolidine-1-carboxylate;

(2S,5R)-7-oxo-N-[(2R)-pyrrolidin-2-ylmethoxy]-6-(sulfooxy)-1,6-diazabicyclo[3.2.1]octane-2-carboxamide;

tert-butyl(3R)-3-{[({[(2S,5R)-6-benzyloxy-7-oxo-1,6-diazabicyclo[3.2.1]oct-2-yl]carbonyl}amino)oxy] methyl}piperidine-1-carboxylate, tetrabutylammonium tert-butyl(3R)-3-{[({[(2S,5R)-7-oxo-6-(sulfooxy)-1,6-diazabicyclo[3.2.1]oct-2-yl] carbonyl}amino)oxy]methyl}piperidine-1-carboxylate;

(2 S,5R)-7-oxo-N-[(3R)-piperidin-3-ylmethoxy]-6-(sulfooxy)-1,6-diazabicyclo[3.2.1]octane-2-carboxamide;

tert-butyl(3S)-3-[({[(2S,5R)-6-benzyloxy-7-oxo-1,6-diazabicyclo[3.2.1]oct-2-yl]carbonyl}amino)oxy]pyrrolidine-1-carboxylate;

tetrabutylammonium tert-butyl(3S)-3-[({[(2S,5R)-7-oxo-6-(sulfooxy)-1,6-diazabicyclo[3.2.1]oct-2-yl]carbonyl}amino)oxy]pyrrolidine-1-carboxylate;

(2S,5R)-7-oxo-N-[(3S)-pyrrolidin-3-yloxy]-6-(sulfooxy)-1,6-diazabicyclo[3.2.1]octane-2-carboxamide;

tert-butyl 3-{[({[(2S,5R)-6-benzyloxy-7-oxo-1,6-diazabicyclo[3.2.1]oct-2-yl]carbonyl}amino)oxy]methyl}azetidine-1-carboxylate;

tetrabutylammonium tert-butyl 3-{[({[(2S,5R)-7-oxo-6-(sulfooxy)-1,6-diazabicyclo[3.2.1]oct-2-yl]carbonyl}amino)oxy]methyl}azetidine-1-carboxylate; and (2S,5R)—N-(azetidin-3-ylmethoxy)-7-oxo-6-(sulfooxy)-1,6-diazabicyclo[3.2.1]octane-2-carboxamide, and include the following group of compounds:

[Chemical Formula 35]

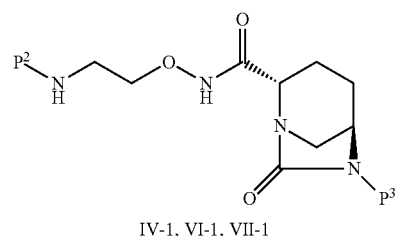

IV-1, VI-1, VII-1

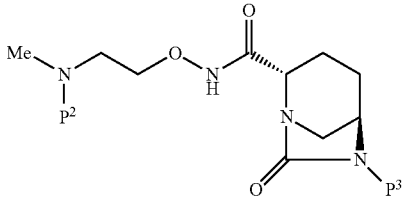

IV-2, VI-2, VII-2

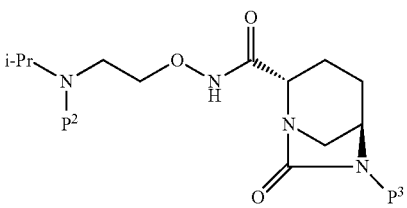

IV-3, VI-3, VII-3

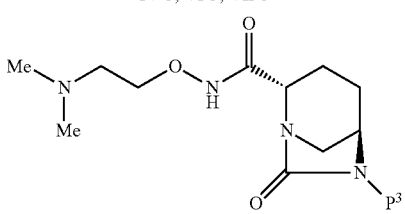

IV-4, VI-4, VII-4

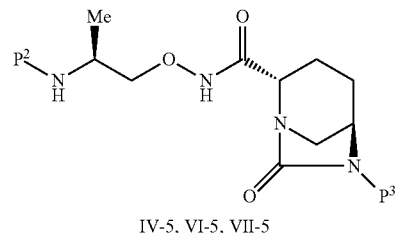

IV-5, VI-5, VII-5

-continued

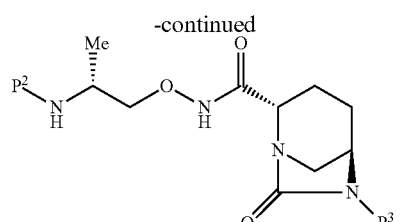

IV-6, VI-6, VII-6

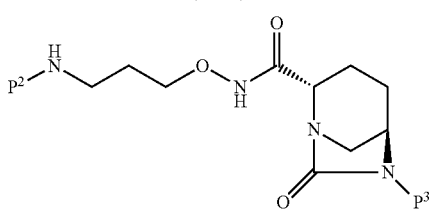

IV-7, VI-7, VII-7

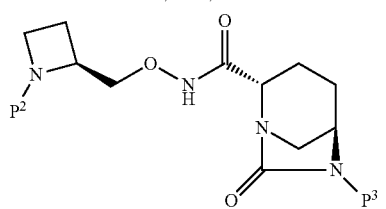

IV-8, VI-8, VII-8

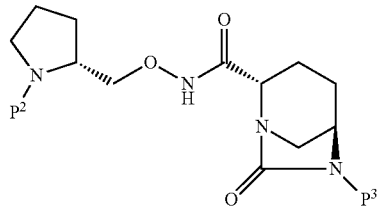

IV-9, VI-9, VII-9

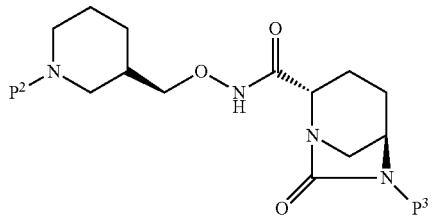

IV-10, VI-10, VII-10

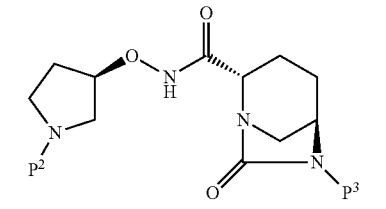

IV-11, VI-11, VII-11

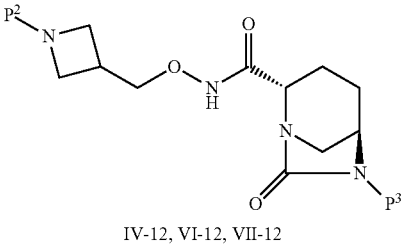

IV-12, VI-12, VII-12

(wherein P² is a protecting group such as tert-butoxycarbonyl (Boc) or hydrogen, and P³ is benzyloxy (OBn), tetrabutylammoniumsulfooxy or sulfooxy).

Most preferably, specific examples include tert-butyl{2-[({[(2S,5R)-6-benzyloxy-7-oxo-1,6-diazabicyclo[3.2.1]oct-2-yl]carbonyl}amino)oxy]ethyl}carbamate;

tetrabutylammonium tert-butyl{2-[({[(2S,5R)-7-oxo-6-(sulfooxy)-1,6-diazabicyclo[3.2.1]oct-2-yl] carbonyl}amino)oxy]ethyl}carbamate;

(2S,5R)—N-(2-aminoethoxy)-7-oxo-6-(sulfooxy)-1,6-diazabicyclo[3.2.1]octane-2-carboxamide;

and they are represented by the aforementioned Formulas (IV-1), (VI-1), (VII-1-CR) and (VII-1).

The compound provided by the present invention is a β-lactamase inhibitor, and demonstrates an action that inhibits decomposition of β-lactam antimicrobial agents by this enzyme. Thus, a pharmaceutical provided by the present invention is premised on concomitant use with a β-lactam antimicrobial agent.

The pharmaceutical provided by the present invention is characterized by containing as active ingredients thereof a substance selected from the group consisting of a compound represented by Formula (VII), a pharmaceutically acceptable salt thereof and a hydrate or solvate thereof, and although it may be administered orally or parenterally, is preferably administered parenterally. A compound of the present invention and a β-lactam antibiotic can be administered by producing a pharmaceutical composition by a method consisting of concomitantly using each pharmaceutical agent individually prepared at the time of use and administering simultaneously or separately, or by mixing both pharmaceutical agents in advance and typically using one or two or more preparation additives (carriers).

Specific examples of pharmaceutical compositions for oral administration include tablets, capsules, granules, powders, pills, aqueous and non-aqueous oral solutions and suspensions.

Examples of administration routes for parenteral administration include intranasal administration, eye drops, ear drops, percutaneous administration, intratracheal administration, intrarectal administration, intraurological administration, subcutaneous administration, intramuscular administration and intravenous administration.

Specific examples of pharmaceutical compositions for parenteral administration include solutions for intravenous injection using a pharmaceutical composition in powdered form with an acceptable solvent for intravenous administration. Examples of acceptable solvents include sterile water for injection, physiological saline solution, glucose solution, Ringer's solution, sterile water for injection containing methylparahydroxybenzoate or propylparahydroxybenzoate, and sterile water for injection containing benzyl alcohol.

A powdered form of a pharmaceutical composition for intravenous administration is produced by dispensing an active pharmaceutical ingredient in the form of a compound of the present invention and a β-lactam antibiotic into a sealed vial after going through a sterilization step.

Here, examples of β-lactam antibiotics that can be used concomitantly with a compound of the present invention include penicillin, cephem and carbapenem antibiotics.

Specific examples of penicillin include benzyl penicillin, phenethicillin, cloxacillin, dicloxacillin, ampicillin, cyclacillin, amoxycillin, talampicillin, becampicillin, lenampicillin, aspoxicillin, piperacillin, sulbenicillin, pivmecillinam, sultamicillin, phenoxymethylpenicillin, carbenicillin, azidocillin, propicillin, epicillin, ticarcillin, pirbenicillin, azlocillin, mezlocillin, and other known penicillin.

Specific examples of cephem include cefaclor, cefazolin, cefatrizine, cefadroxil, cephapirin, cefamandole nafate, cefradine, cephalexin, cephalothin, cefepim, cefoxitin, cefixime, cefzidime, cefditoren, cefdinir, cefsulodin, cefselis, cefzopran, ceftaxime, ceftazidime, ceftaroline, ceftiam, ceftizoxime, ceftibuten, ceftezole, ceftetam, ceftriaxone, cefnicid, cefpiramide, cefpirome, cefbuperazone, cefprozil, cefperazone, cefpodoxime, cefminox, cefmetazole, cefmenoxime, cefradine, cefroxadine, cefroxadine, ceftolozane (CXA101; hydrogen sulfate salt of (6R,7R)-3-[5-amino-4-[3-(2-aminoethyl)ureide]-1-methyl-1H-pyrazol-2-ium-2-yl-methyl]-7-[2-(5-amino-1,2,4-thiadiazol-3-yl)-2-[(Z)-1-carboxy-1-methylethoxyimino]acetamide]-3-cephem-4-carboxylic acid), and other known cephem.

Examples of carbapenem antibiotics include imipenem, panipenem, meropenem, biapenem, doripenem, ertapenem and tebipenem, and these can be used concomitantly with DHP-1 inhibitors such as cilastatin sodium as necessary.

Examples of β-lactam antibiotics other than carbepenem, penicillin and cephem include aztreonam, carumonam, latamoxef, loracarbef, faropenem and ritipenem.

Examples of penicillin those are particularly preferable for concomitant administration with a compound according to the present invention include ampicillin, amoxicillin, carbenicillin, piperacillin, azlocillin, mezlocillin and ticarcillin. These penicillins can be used in the form of a pharmaceutically acceptable salt in the manner of a sodium salt, for example. In another form, ampicillin or amoxicillin can be used concomitantly with a compound represented by Formula (VII) in the form of a suspension for injection or zwitterionic (ampicillin trihydrate or amoxicillin trihydrate) fine granules for use in a suspension for injection. Examples of cephem-based antibiotics particularly preferable for concomitant administration with a compound according to the present invention include cefotaxime, ceftriaxone, ceftazidime and cefepime, and these can be used in the form of a pharmaceutically acceptable salt in the manner of a sodium salt. Examples of carbapenem antibiotics particularly preferable for concomitant administration with a compound according to the present invention include imipenem, meropenem, biapenem, doripenem and ertapenem.

An example of a β-lactam antibiotic other than carbepenems, penicillins and cephems antibiotics that is particularly preferable for concomitant administration with a compound according to the present invention is aztreonam.

The following provides sequential explanations of processes for producing a compound represented by the following Formula (VII) and crystals thereof provided by the present invention.

[Chemical Formula 36]

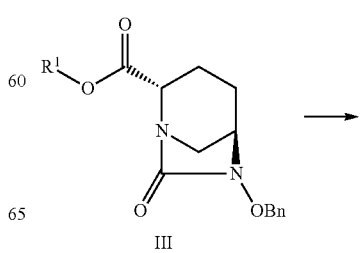

III

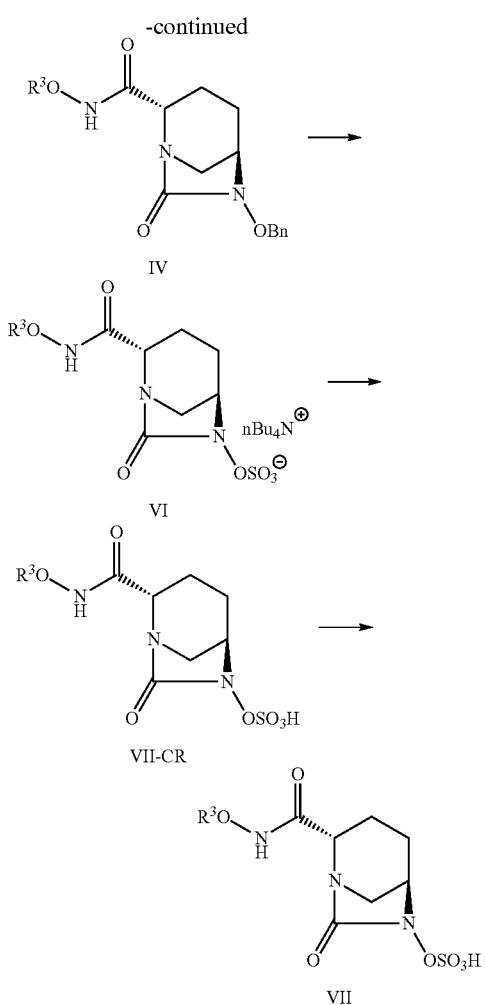

(In the above Formulas (III), (IV), (VI), (VII-CR) and (VII), OBn, R¹ and R³ are same as described above.)

The step for obtaining a compound represented by Formula (IV) from a compound represented by the following Formula (III):

(wherein OBn, R¹ and R³ are same as described above) is carried out in the manner described below.

Examples of solvent used include water, methanol, ethanol, isopropanol, ethyl acetate, tetrahydrofuran, dioxane, dichloromethane, chloroform, 1,2-dichloroethane and 2,2,2-trifluoroethanol, preferable examples include ethyl acetate, dioxane, dichloromethane, chloroform and dichloroethane, and these solvents are used alone or as a mixture.

The compound: $R^3ONH_2$ used in the reaction is selected from those listed as specific examples of $R^3$, and is used within the range of 1 to 2 equivalents, and preferably 1 to 1.3 equivalents, based on the compound represented by Formula (III).

Examples of base used in the reaction include sodium hydrogencarbonate, potassium hydrogencarbonate, sodium carbonate, potassium carbonate, cesium carbonate, sodium hydroxide, potassium hydroxide, triethylamine, diisopropylethylamine, dimethylbutylamine, tributylamine, N-methylmorpholine, pyridine, N-methylimidazole, 4-dimethylaminopyridine, and triethylamine is used preferably, and the base can be used in the form of an aqueous solution in the case of using an inorganic base. The base is used within the range of 0 to 2 equivalents, and preferably 0 to 1.5 equivalents, based on the compound represented by Formula (III). The reaction temperature is within the range of −25 to 50° C. and preferably within the range of −10 to 10° C. The reaction time is within the range of 1 to 24 hours and preferably within the range of 1 to 16 hours.

The compound represented by Formula (IV) can be isolated after completion of the reaction by diluting the reaction solution with a suitable solvent and sequentially washing with water, diluted acid and an aqueous basic solution (such as dilute hydrochloric acid, potassium hydrogensulfate, citric acid and aqueous sodium bicarbonate or saturated brine) followed by concentrating by evaporating the solvent. Examples of organic solvents used for dilution include diethyl ether, ethyl acetate, butyl acetate, toluene, dichloromethane and chloroform, and ethyl acetate is preferable. Although the product is isolated by ordinary work-up and purification procedures, it can be used in the next step after work-up only.

The step for converting a compound represented by the following Formula (IV):

[Chemical Formula 37]

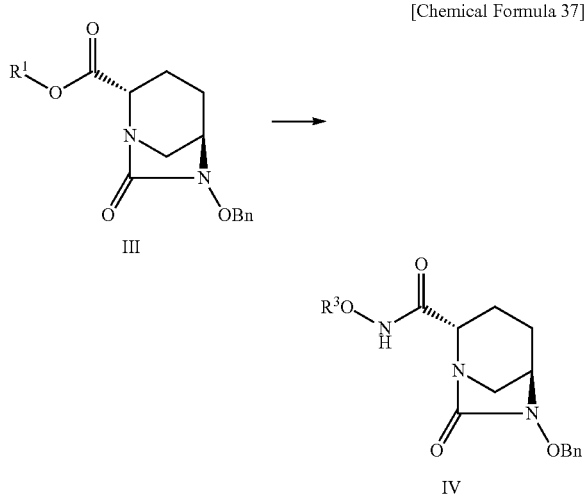

[Chemical Formula 38]

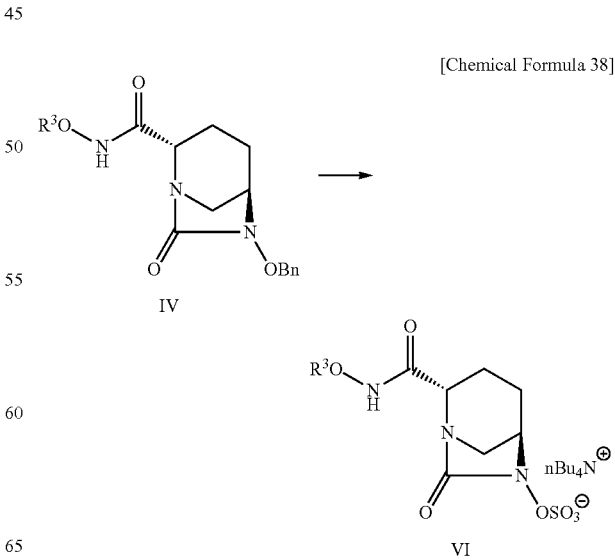

to a compound represented by Formula (VI) above is carried out in the manner described below.

Examples of solvents used in the reaction include water, methanol, ethanol, isopropanol and acetonitrile, and these solvents are used alone or as a mixture. In the case of carrying out the debenzylation reaction and sulfation reaction simultaneously, a hydrous solvent is preferable, and in the case of carrying out continuously, water is preferably added during sulfation. The amount of water added is within the range of 50 to 200% by volume, and preferably 75 to 125% by volume, of the solvent.

The amount of palladium carbon used is within the range of 5 to 100% by weight, and preferably 5 to 30% by weight, based on the compound represented by Formula (IV).

The supply source of hydrogen used in hydrogenolysis is hydrogen gas, and the hydrogen pressure is selected within a range of atmospheric pressure to 1 MPa and preferably from atmospheric pressure to 0.5 MPa. The amount of hydrogen supplied is at least that used in an amount equal to or greater than the stoichiometric amount.

The reaction temperature of hydrogenolysis is within the range of 10 to 50° C. and preferably within the range of 20 to 30° C. The reaction time is within the range of 0.5 to 3 hours and preferably within the range of 0.5 to 2 hours.

The sulfur trioxide-trimethylamine complex used as a sulfation reagent is used within the range of 1 to 2 equivalents, and preferably 1 to 1.3 equivalents, based on the compound represented by Formula (IV).

Examples of base used in sulfation include triethylamine, tributylamine, diisopropylethylamine, N-methylmorpholine and disodium hydrogenphosphate, and triethylamine is used preferably, and the base can be used within the range of 0.1 to 1 equivalent, and preferably 0.1 to 0.3 equivalents, based on the compound represented by Formula (IV).

The reaction temperature of sulfation is within the range of 0 to 50° C. and preferably within the range of 15 to 30° C. The reaction time is within the range of 12 to 48 hours and preferably within the range of 12 to 24 hours.

After completion of the reaction, the compound represented by Formula (VI) can be obtained by filtering out impurities such as catalyst and adding a concentrate obtained by solvent evaporation to an aqueous sodium dihydrogenphosphate solution, followed by adding 1 to 3 molar equivalents of tetrabutylammonium hydrogen sulfate, extracting with an organic solvent such as ethyl acetate and concentrating by evaporating the solvent. The resulting compound represented by Formula (VI) can be used as a concentrated solution to the next step without isolating or purifying.

The step for converting a compound represented by the following Formula (VI):

[Chemical Formula 39]

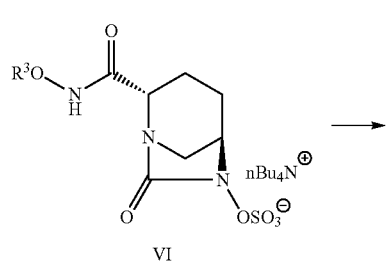

VI

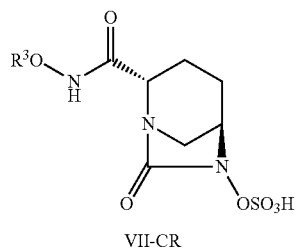

VII-CR to a compound represented by Formula (VII-CR) above is carried out in the manner described below.

Examples of solvents used in the step for deprotecting a protecting group optionally contained in $R^3O$—NHC(=O)—, particularly a tert-butoxycarbonyl (Boc) group, include ethyl acetate, tetrahydrofuran, dioxane, dichloromethane, chloroform, 1,2-dichloroethane and 2,2,2-trifluoroethanol, and dichloromethane or ethyl acetate is used preferably, and the solvent is used alone or as a mixture. The amount of solvent used is within the range of 2 to 10 vol/wt, and preferably 2 to 6 vol/wt, based on the net weight of the compound represented by Formula (VI).

Examples of acids used in deprotection include hydrochloric acid, sulfuric acid, phosphoric acid, formic acid, trifluoroacetic acid, methanesulfonic acid, trifluoromethanesulfonic acid, chloromethanesulfonic acid and tetrafluoroboric acid, and trifluoroacetic acid is preferable. The acid is used within the range of 2 to 10 vol/wt, and preferably 2 to 6 vol/wt based on the net weight of the compound represented by Formula (VI). The acid is added within orange of −50 to 0° C. and preferably within a range of −20 to 0° C. The reaction temperature is within the range of −5 to 20° C. and preferably within the range of −5 to 5° C. The reaction time is within the range of 0.5 to 5 hours and preferably within the range of 0.5 to 3 hours.

Following completion of deprotection, the step for obtaining a compound represented by Formula (VII-CR) by cooling the reaction solution and adding a poor solvent is carried out in the manner described below. Examples of the poor solvent used include ether-based poor solvents and ester-based poor solvents, preferable examples include ester-based poor solvents such as ethyl acetate, isopropyl acetate or butyl acetate, and ethyl acetate is even more preferable. The amount of poor solvent used is 1 to 3 times, and preferably 1.5 to 2 times, the volume of the reaction solution. The poor solvent, preliminarily cooled to −5 to 5° C., is added to the reaction solution by dividing or dropping. Following completion of addition of the poor solvent, the reaction solution is additionally stirred. Precipitated material is filtered and washed several times as necessary, the resulting wet solid is subjected to vacuum ring and dried for 10 hours or more until the temperature of the material reaches room temperature to obtain the compound represented by Formula (VII-CR).

The step for converting a compound represented by the following Formula (VII-CR):

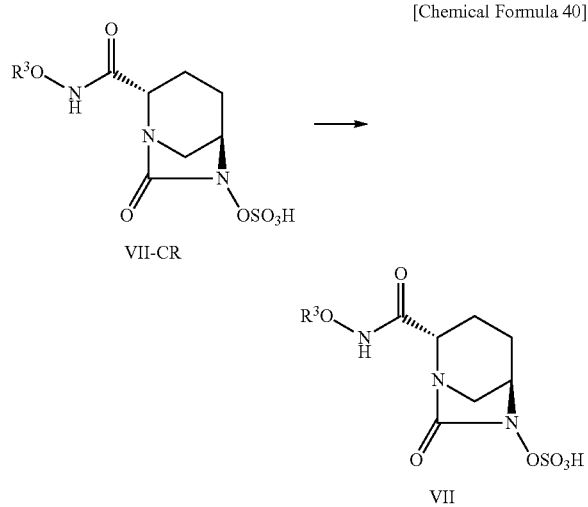

[Chemical Formula 40]

VII-CR

VII to a compound represented by Formula (VII) above is carried out in the manner described below.

A phosphate buffer having a pH of 6.5 is preferable for the buffer used to adjust the pH of the compound represented by the aforementioned Formula (VII-CR). The concentration of the buffer is selected within the range of 0.1 to 0.5 M and is preferably 0.2 M, although varying according to remaining of the trifluoroacetic acid in the compound represented by the aforementioned Formula (VII-CR). The total amount of buffer used is within the range of 10 to 50 vol/wt based on the net weight of the compound represented by Formula (VII-CR).

Following 5 to 7 vol/wt of phosphate buffer is preliminarily cooled to 0 to 10° C., the pH is adjusted by alternately adding and dissolving small part of the compound represented by Formula (VII-CR) and the cooled phosphate buffer so that the pH is between 4 and 5.5 and preferably 4.2 and 4.8 and ultimately adjusting to pH 4.6, followed by diluting by adding water to 25 vol/wt in the case the total amount is less than 25 vol/wt based on the net weight of the compound represented by Formula (VII-CR), and concentrating under reduced pressure to 20 vol/wt at a solution temperature of 15° C. or lower. Moreover, the pH of the aqueous solution is adjusted to 5.4 with phosphate buffer followed by diluting with water to obtain an aqueous solution having a concentration of 36 vol/wt.

Desalting of the aqueous solution following the aforementioned adjustment of pH is carried out as necessary by column purification using a synthetic adsorbent. Examples of synthetic adsorbents used include Diaion HP-20 and SepaBeads SP-207, Mitsubishi Chemical, and SepaBeads SP-207 is used preferably. The synthetic adsorbent is used within a range of 55 to 65 vol/wt based on the net weight of the compound represented by Formula (VII-CR). Desalting is carried out by adsorbing the aforementioned aqueous solution to the synthetic adsorbent, desalting with 65 to 70 vol/wt of water, and eluting with 150 to 200 vol/wt of 10% isopropanol. The active fraction is contained within the range of 20 to 25 vol/wt. Crystallization is carried out using a concentrate obtained by concentrating the resulting active fraction under reduced pressure to 5 to 7 vol/wt at a solution temperature of 20° C. or lower.

Crystal polymorphs may be solvated or anhydrous (such as an anhydride, monohydrate or dihydrate). Crystalline forms I, II, III and IV exist as crystal polymorphs of a compound represented by Formula (VII-1). Crystalline forms I and III crystallize at 0 to 35° C. and preferably room temperature of 20 to 25° C., more preferably as a result of seeding with a seed crystal, while crystalline form II can crystallize in the absence of seed crystal under supersaturated conditions by cooling at 15° C. or lower and addition of poor solvent. Crystalline form IV can crystallize at room temperature using alcohol-based solvents such as methanol which dissolve a compound represented by Formula (VII-1) well as poor solvent, or be obtained by recrystallizing crystalline forms I to III in an alcohol solvent under a dehydrating condition.

Crystalline forms I, II and III are distinguished by DSC, solubility in aqueous isopropanol, and lattice spacing in powder X-ray diffraction patterns. Crystalline form I has the lowest solubility in aqueous isopropanol, while crystalline forms II and III have similar solubility.

Crystallization of the compound represented by the aforementioned Formula (VII) is carried out in the manner described below. The initial amount of chemical solution is adjusted to a concentration that allows the crystalline form having the lowest solubility to adequately dissolve. In the case of the compound represented by Formula (VII-1), the initial amount is within the range of 10% to 30% and preferably 10% to 20%. In the case of a crystalline form for which seeding is preferred, seed crystal is prepared in advance. Seed crystals of crystalline form I are acquired at room temperature, while seed crystals of crystalline form III can be obtained in free of contamination by successive crystallization within the range of 15% to 25%. The amount of seed crystal used is 0.01 to 20% and preferably 0.01% to 2%.

Examples of poor solvents used include methanol, ethanol, isopropanol, acetone, acetonitrile and tetrahydrofuran, and preferably include alcohol-based poor solvents such as methanol, ethanol or isopropanol. The amount of the poor solvent is adjusted based on solubility so that isolation loss is 1% or less. In the case of the compound represented by Formula (VII-1), the poor solvent is used at 1 to 10 times, and preferably 6 to 7 times, the initial volume of the solution. The timing of the addition of poor solvent is such that the poor solvent is dropped in after the mixture has formed a slurry following seeding in the case of crystalline form I, immediately after seeding in the case of the crystalline forms II and III, and without seeding in the case of the crystalline form IV.

The crystalline form IV can be also obtained by suspending and stirring the crystalline form I, II or III in methanol, ethanol or isopropanol instead of making an aqueous solution thereof.

Controlling the temperature of the solution is an important factor in terms of controlling the desired crystal polymorphism, and is determined by referring to the precipitation rate of crystal polymorphs at a set temperature. In the case of a compound represented by Formula (VII-1), crystalline forms I, and IV are controlled to within a range of 20 to 25° C., while crystalline form II is controlled to a temperature of 15° C. or lower. In addition, in the case of a crystalline form IV obtained by suspending and stirring the crystalline form I, II or III in a solvent instead of making an aqueous solution thereof, in conjunction with the solubility of the crystalline form I, II or III in the solvent, it is controlled at a temperature within a range of 20 to 100° C. and preferably within a range of 20 to 65° C.

Stirring time is dependent upon precipitation rate, and stirring is carried out for 1 hour to 24 hours and preferably for 1 hour to 15 hours.

The crystalline form of the compound represented by Formula (VII) can be obtained by ordinary filtration, washing and vacuum drying or through-flow drying of the precipitated crystals. In the case of solvated crystals, excessive drying is avoided by using means to controlling material temperature, loss on drying, humidified and limited vacuum drying or humidified through-flow drying.

EXAMPLES

The present invention will be described below in more detail by way of Examples, but the present invention is not intended to be limited by these Examples, and various modifications can be made.

Reference Example 1

Methyl(2S,5R)-5-(benzyloxyamino)piperidine-2-carboxylate dihydrochloride

Step 1

Methyl(2S,5S)-5-hydroxypiperidine-2-carboxylate

To a 2 M hydrogen chloride in methanol solution (12.8 L) was added commercially available (2S,5S)-5-hydroxypiperidine-2-carboxylic acid (prelabel HPLC content 84%, net 912.22 g, washed with 3.1 L of 2 M hydrogen chloride in methanol), followed by refluxing for 3 hours (internal temperatures of 63 to 67° C.). After the reaction solution was cooled, 1,4-dioxane (12.8 L) was added, and the solvent was distilled off under reduced pressure. To the residue (4.1 kg) were added ethyl acetate (18.3 L) and an ice cold 44% aqueous potassium carbonate solution (23.7 L) to separate the organic layer, and the aqueous layer was further extracted with ethyl acetate (3×18.3 L). Each of the organic layers was washed with a 50% aqueous potassium carbonate solution (7.3 L). The organic layers were combined, dried over anhydrous potassium carbonate (2.37 kg) and filtered, and the solvent was distilled off under reduced pressure. The residue was dissolved in toluene (9.1 L), and 9.2 g of activated carbon was added, followed by stirring for 30 minutes and filtering. The solvent was then distilled off under reduced pressure. The solvent of the residue was switched to ethyl acetate (9.1 L) to afford 1130 g of the title compound as a pale yellow oil (prelabel HPLC content 78.9%, net 891.57 g, yield 89%).

Step 2

Methyl(2S,5S)-5-hydroxy-1-(2,2,2-trifluoroacetyl)piperidine-2-carboxylate

A dehydrated ethyl acetate solution (7.4 L) of methyl(2S,5S)-5-hydroxypiperidine-2-carboxylate (prelabel HPLC content 78.8%, net 459.48 g) was cooled to −40° C., followed by addition of triethylamine (1300 g), and then dropwise addition of trifluoroacetic acid anhydride (1349 g, washed with 100 mL of dehydrated ethyl acetate) at −40 to −12° C. for 30 minutes. After completion of the dropwise addition, the temperature was elevated to −2° C. in 15 minutes, and the mixture was stirred for 75 minutes, and to the mixture was further added water (1277 mL), followed by stirring at 25° C. for 1 hour. The mixture was introduced into water (8.4 L) (washed with 4.5 L of ethyl acetate) and further extracted with ethyl acetate (2×9.8 L), and the combined organic layer was washed sequentially with 1 M hydrochloric acid (8.5 L), saturated sodium bicarbonate (8.5 L), and saturated brine (8.5 L), dried over anhydrous sodium sulfate (1.8 kg), and filtered. The solvent of the organic layer was distilled off under reduce pressure, and to the residue was added ethyl acetate (3.6 L), followed by substitution-concentration. The residue was then dried in vacuo to afford 793.4 g of the title compound (HPLC content 81.5%, net 648.66 g, yield 88%).

Step 3

Methyl(2S,5R)-5-(benzyloxyamino)-1-(2,2,2-trifluoroacetyl)piperidine-2-carboxylate 4.0 L of a solution of methyl(2S,5S)-5-hydroxy-1-(2,2,2-trifluoroacetyl)piperidine-2-carboxylate (HPLC content 81.5%, net 556.23 g) in dehydrated acetonitrile was cooled to −40° C., and 2,6-lutidine (259.24 g) was added (washed with 100 mL of acetonitrile), followed by dropwise addition of trifluoromethanesulfonic anhydride (645.72 g) at −43 to −37° C. over 1 hour and 10 minutes (washed with 100 mL of acetonitrile). The reaction solution was stirred at −35° C. for 50 minutes, and then benzyloxyamine (550.27 g) was added dropwise at −35° C. or less, followed by washing with acetonitrile (500 mL). After gradually elevating the reaction solution to −5° C. 2,6-lutidine (259.24 g) was added, followed by stirring at 5° C. for 40 hours. After concentration to 1.8 L, the mixture was diluted with ethyl acetate (12.4 L) and washed sequentially with water (12.4 L), 10% citric acid (4×8 L+4.7 L), saturated sodium bicarbonate (6.3 L), and saturated brine (7.2 L). The organic layer was dried over anhydrous sodium sulfate, filtered, and then concentrated under reduced pressure. The residue was dried in vacuo to afford 867.73 g of the title compound (HPLC content 71.56%, yield 79%).

Step 4

Methyl(2S,5R)-5-(benzyloxyamino)-1-(2,2,2-trifluoroacetyl)piperidine-2-carboxylate hydrochloride Methyl(2S,5R)-5-(benzyloxyamino)-1-(2,2,2-trifluoroacetyl)piperidine-2-carboxylate (HPLC content 70.13%, net 673.20 g) was diluted with ethyl acetate (4.8 L), and 48 g of activated carbon was added, followed by stirring for 1 hour. The mixture was filtered and washed with 2 L of ethyl acetate. The filtrate was diluted with 4.7 L of ethyl acetate, and a 1 M hydrogen chloride in ethyl acetate solution (2.7 L) was added at room temperature, followed by stirring for 15 minutes, and then 28.6 L of hexane was added, followed by cooling to 0° C. After stirring for 3 hours, the crystalline solid were filtered, washed with hexane/ethyl acetate=4/1 (3 L), and dried in vacuo to afford 724.0 g of the title compound (HPLC content 91.72%, yield 90%).

Step 5

Methyl(2S,5R)-5-(benzyloxyamino)piperidine-2-carboxylate dihydrochloride

Methyl(2S,5R)-5-(benzyloxyamino)-1-(2,2,2-trifluoroacetyl)piperidine-2-carboxylate hydrochloride (HPLC content 92.01%, net 732.25 g) was dissolved in a 2 M hydrogen chloride in methanol solution (15 L), followed by heating at reflux for 27 hours. The mixture was cooled to room temperature and concentrated under reduced pressure to 3 L. The mixture was diluted with 2.7 L of methanol, and then 16.3 L of ethyl acetate was added, followed by stirring for 1 hour. The precipitated crystalline-solid was filtered, washed with ethyl acetate (3×1.1 L), and dried in vacuo to afford 572.0 g of the title compound (HPLC content 98.06%, yield 92%).

$^1$H NMR (400 MHz, D$_2$O) δ 1.40-1.51 (m, 1H), 1.61-1.72 (m, 1H), 1.90-1.94 (m, 1H), 2.25-2.30 (m, 1H), 2.80 (t, J=11.2 Hz, 1H), 3.19-3.27 (m, 1H), 3.51-3.55 (m, 1H), 3.66 (s, 3H), 3.87-3.91 (m, 1H), 4.68 (s, 2H), 7.27 (s, 5H); MS m/z 265 [M-2HCl+H]$^+$.

Reference Example 2

(2S,5R)-6-(Benzyloxy)-7-oxo-1,6-diazabicyclo[3.2.1]octane-2-carboxylic acid

Step 1

Methyl(2S,5R)-5-(benzyloxyamino)piperidine-2-carboxylate

To methyl(2S,5R)-5-(benzyloxyamino)piperidine-2-carboxylate dihydrochloride (Reference Example 1, 1.319 g) were added ethyl acetate (20 mL) and 50% potassium carbonate (20 mL) to separate the layers. The aqueous layer was extracted three times with ethyl acetate (15 mL). The organic layer was washed with saturated brine, dried over anhydrous sodium sulfate, filtered, concentrated under reduced pressure and then dried in vacuo overnight to afford 975 mg of the title compound (yield 94%).

$^1$H NMR (400 MHz, CDCl$_3$) δ 1.25-1.35 (m, 1H), 1.49-1.59 (m, 1H), 1.89-2.11 (m, 2H), 2.45 (t, J=11.7 Hz, 1H), 2.96-3.03 (m, 1H), 3.28-3.39 (m, 2H), 3.72 (s, 3H), 4.68 (s, 2H), 7.26-7.35 (m, 5H); MS m/z 265 [M+H]$^+$.

Step 2

Methyl(2S,5R)-6-(benzyloxy)-7-oxo-1,6-diazabicyclo[3.2.1]octane-2-carboxylate

To methyl(2S,5R)-5-(benzyloxyamino)piperidine-2-carboxylate (1.154 g, 4.37 mmol) was added dehydrated acetonitrile (198 mL), followed by ice-cooling. At 5° C. or less, triethylamine (1.60 mL) and diphosgene (0.389 mL) were sequentially added dropwise, followed by stirring at 2° C. for 20 minutes. To the reaction solution was then added 4-dimethylaminopyridine (70.0 mg), followed by stirring at room temperature for 10 hours. The reaction solution was concentrated under reduced pressure and solvent-switched three times to ethyl acetate, and the solution was concentrated to 30 mL. To this were added ethyl acetate (20 mL) and water (40 mL) to separate the layers. The separated aqueous layer was extracted twice with ethyl acetate (30 mL). The combined organic layer was washed sequentially with 5% citric acid (40 mL), 6.5% sodium bicarbonate (30 mL), and 5% brine (30 mL), dried over anhydrous sodium sulfate, filtered, and then concentrated under reduced pressure. 1.16 g of the resulting residue was diluted with ethyl acetate (5.5 mL), n-hexane (11 mL) was added, and seed crystals were seeded and crystallized. n-Hexane (49 mL) was further added and stirred at 0° C. for 1 hour, and then crystalline solid was filtered, washed with n-hexane (60 mL), and dried in vacuo to afford 882.3 mg of the title compound as a colorless crystalline powder (yield 71%).

$^1$H NMR (400 MHz, CDCl$_3$) δ 1.65-1.70 (m, 1H), 2.03-2.12 (m, 3H), 2.90 (d, J=12.0 Hz, 1H), 3.07 (m, 1H), 3.32 (m, 1H), 4.12 (dd, J=4.6&4.4 Hz, 1H), 4.91 (d, J=11.2 Hz, 1H), 5.06 (d, J=11.2 Hz, 1H), 7.35-7.44 (m, 5H); MS m/z 291 [M+H]$^+$.

Step 3

(2S,5R)-6-(Benzyloxy)-7-oxo-1,6-diazabicyclo[3.2.1]octane-2-carboxylic acid

To methyl(2S,5R)-6-(benzyloxy)-7-oxo-1,6-diazabicyclo[3.2.1]octane-2-carboxylate (809.0 mg, 2.79 mmol) were added tetrahydrofuran (8 mL) and water (3.6 mL), followed by dropwise addition of 0.5 M lithium hydroxide (6.41 mL) at 4.9° C. or less over 10 minutes. After stirring the reaction solution at 2° C. for 2 hours, water (30 mL) was added, followed by washing with ethyl acetate (25 mL). To the separated aqueous layer was added ethyl acetate (15 mL), and the pH was adjusted to 4.0 with 1 M hydrochloric acid, followed by extraction twice with ethyl acetate (ethyl acetate: 65 mL in total). The separated aqueous layer was adjusted to pH 3.4 with 1 M hydrochloric acid, extracted once with ethyl acetate, and then the aqueous layer was adjusted to pH 2.4 and extracted twice with ethyl acetate. The ethyl acetate-extract extracted five times in total (175 mL) was washed with saturated brine (40 mL), dried over anhydrous sodium sulfate, filtered, and then concentrated under reduced pressure. 759.1 mg of the resulting residue was diluted with ethyl acetate (5 mL), n-hexane (3 mL) was added, and seed crystals were seeded and crystallized. An ethyl acetate/n-hexane (5/3) solution (8 mL) was further added and stirred, and then n-hexane (20 mL) was added, followed by stirring at 4° C. for 14 hours. The crystalline solid was filtered, washed with n-hexane (55 mL), and then dried in vacuo to afford 633.6 mg of the title compound as a colorless crystalline powder (yield 82%).

$^1$H NMR (400 MHz, CDCl$_3$) δ 1.67 (m, 1H), 2.04-2.26 (m, 3H), 2.85 (d, J=12.0 Hz, 1H), 3.13 (m, 1H), 3.35 (m, 1H), 4.12 (m, 1H), 4.91 (d, J=11.3 Hz, 1H), 5.06 (d, J=11.3 Hz, 1H), 7.37-7.44 (m, 5H); MS m/z 277 [M+H]$^+$.

Reference Example 3

2,5-Dioxopyrrolidin-1-yl(2S,5R)-6-(benzyloxy)-7-oxo-1,6-diazabicyclo[3.2.1]octane-2-carboxylate

[Chemical Formula 41]

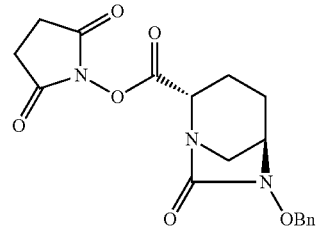

Step 1

(2S,5R)-5-((Benzyloxy)amino)-1-(tert-butoxycarbonyl)piperidine-2-carboxylic acid Methyl(2S,5R)-5-(benzyloxyamino)piperidine-2-carboxylate dihydrochloride (Reference Example 1, 65.4 g, 200 mmol) was dissolved in water (400 mL) and 1,4-dioxane (270 mL), and the solution was ice-cooled. 5 M sodium hydroxide (132 mL) was then added, followed by stirring for 1 hour. To the reaction solution was added 5 M hydrochloric acid (12 mL), potassium carbonate (27.6 g), and di-tert-butyl dicarbonate (48 g), and the temperature of the mixture was elevated to room temperature, followed by stirring overnight. The concentrated aqueous solution of the reaction solution was washed with ethyl acetate, adjusted to pH 3.3 with citric acid monohydrate, extracted twice with ethyl acetate (500 mL), washed with saturated brine, dried over anhydrous sodium sulfate, and filtered, and the solvent was concentrated under reduced pressure and further solvent-switched to ethyl acetate to afford 68.7 g of the title compound (quantitative). The compound was used in the next step without purification. A portion thereof was crystallized with ethyl acetate/hexane to confirm the structure thereof.

$^1$H NMR (400 MHz, CDCl$_3$) δ 1.46 (s, 9H), 1.50-1.72 (m, 2H), 1.98-2.10 (m, 2H), 3.12-3.19 (m, 2H), 4.13-4.20 (m, 1H), 4.76 (d, J=11.5 Hz), 4.70 (d, J=11.5 Hz), 4.85-4.92 (m, 1H), 7.26-7.35 (m, 5H); MS m/z 351 [M+H]$^+$.

Step 2

2,5-Dioxopyrrolidin-1-yl(2S,5R)-6-(benzyloxy)-7-oxo-1,6-diazabicyclo[3.2.1]octane-2-carboxylate (2S,5R)-5-((Benzyloxy)amino)-1-(tert-butoxycarbonyl) piperidine-2-carboxylic acid (Reference Example 3, Step 1, 700 mg, 2 mmol) was dissolved in dehydrated tetrahydrofuran (10 mL), and cooled to −20° C. To the mixture were sequentially added dropwise isobutyl chloroformate (300 mg) and triethylamine (444 mg), followed by stirring for 15 minutes. To the reaction solution was added 1-hydroxypyrrolidine-2,5-dione (253 mg), followed by stirring for 30 minutes and further stirring at room temperature for 30 minutes. The reaction solution was diluted with ethyl acetate (35 mL), washed sequentially with 10% citric acid (10 mL), saturated sodium bicarbonate (10 mL), and saturated brine (10 mL), dried over anhydrous magnesium sulfate, and filtered, and the solvent was distilled off under reduced pressure to afford 985 mg of a residue. The total amount of the residue was dissolved in dehydrated chloroform (10 mL), and to the solution was added triethylamine (303 mg), followed by ice-cooling. To the mixture was added triphosgene (237 mg), followed by stirring for 30 minutes. To this was then added methanol (0.1 mL), followed by stirring for 30 minutes. A solution of methanesulfonic acid (1.3 mL) in dichloromethane (4.0 mL) was then added dropwise and stirred further for 30 minutes. The mixture was added dropwise to ice-cold 1 M potassium hydrogencarbonate (2.4 g/20 mL), followed by stirring for 30 minutes. Chloroform (10 mL) was then added to separate the layers. The organic layer was washed sequentially with 1 M hydrochloric acid (10 mL), saturated sodium bicarbonate (10 mL), and saturated brine (10 mL). The organic layer was dried over anhydrous magnesium sulfate, filtered, and concentrated under reduced pressure. The residue was seeded with crystals, and to the solid was added hexane/ethyl acetate (1/2, 3 mL). The mixture was then stirred, filtered, and washed sequentially with hexane/ethyl acetate (1/1, 3 mL) and hexane (3 mL) to afford 556 mg of the title compound as crystals (yield 75%).

$^1$H NMR (400 MHz, CDCl$_3$) δ 1.70-1.77 (m, 1H), 2.04-2.27 (m, 3H), 2.80-2.90 (m, 4H), 3.09-3.19 (m, 2H), 3.35 (br.s., 1H), 4.48 (d, J=6.9 Hz, 1H), 4.92 (d, J=11.3 Hz, 1H), 5.07 (d, J=11.3 Hz, 1H), 7.35-7.45 (m, 5H); MS m/z 374 [M+H]$^+$.

Reference Example 4

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate

[Chemical Formula 42]

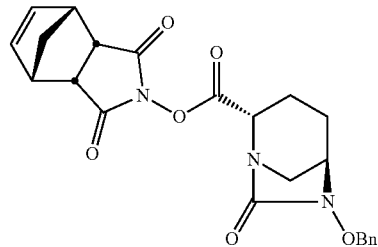

(2S,5R)-5-((Benzyloxy)amino)-1-(tert-butoxycarbonyl) piperidine-2-carboxylic acid (Reference Example 3, Step 1, 14.0 g, 41.09 mmol) was dissolved in dehydrated tetrahydrofuran (200 mL), followed by cooling to around −20° C. To the mixture was added dropwise isobutyl chloroformate (6.11 g) and then triethylamine (8.86 g), followed by stirring at the same temperature for 15 minutes. To the reaction solution was then added (1R,2S,6R,7S)-4-hydroxy-4-azatricyclo[5.2.1.0$^{2,6}$]dec-8-en-3,5-dione (7.87 g), followed by stirring at the same temperature for 30 minutes and further stirring at room temperature for 30 minutes. The reaction solution was diluted with ethyl acetate (700 mL), washed sequentially with ice-cold 10% citric acid (200 mL), saturated sodium bicarbonate (200 mL), and saturated brine (200 mL), dried over anhydrous magnesium sulfate, and filtered. The solvent was distilled off under reduced pressure, and again substitution-concentrated with ethyl acetate. The total amount of the resulting residue (25.1 g) (net yield 92%) was dissolved in dehydrated chloroform (180 mL), and to the solution was added triethylamine (5.5 g), followed by ice-cooling. To the mixture was added triphosgene (4.29 g), followed by stirring for 30 minutes. To this was then added methanol (1 mL), followed by stirring for 30 minutes. To the reaction solution was added dropwise a solution of methanesulfonic acid (23.5 mL) in dichloromethane (30 mL), followed by further stirring for 30 minutes. The mixture was added dropwise to ice-cold 1 M potassium hydrogencarbonate (43.5 g/200 mL), followed by stirring for 30 minutes. Chloroform (100 mL) was then added to separate the layers. The organic layer was washed sequentially with 1 M hydrochloric acid (200 mL), saturated sodium bicarbonate (200 mL), and saturated brine (200 mL). Each of the aqueous layers was sequentially back-extracted with chloroform (100 mL). The organic layers were combined, dried over anhydrous magnesium sulfate, and filtered. The solvent was concentrated under reduced pressure, and the resulting residue was dissolved in chloroform (70 mL). To the solution was added hexane (100 mL), followed by stirring for 30 minutes for crystallization. To this was further added hexane (100 mL), followed by stirring for 1 hour. The crystalline material was filtered and dried to afford 15.4 g of the title compound (content 100%, yield 88%).

HPLC: COSMOSIL 5C18 MS-II 4.6×150 mm, 35° C., 0.02 M TFA/CH$_3$CN=50/50, 1.0 mL/min, UV 210 nm, RT 7.1 min; enantiomeric excess 99.9% ee or more: CHIRAL-PAK AD-H, 4.6×150 mm, 40° C., Hexane/EtOH=1/1, UV 210 nm, 1 mL/min, RT 37.3 min (cf. enantiomer 16.5 min); Mp 196° C.; [α]$^{26}_D$+12.686° (c 0.885, CHCl$_3$); $^1$H NMR (400 MHz, CDCl$_3$) δ 1.52 (d, J=9.1 Hz, 1H), 1.70 (m, 1H), 1.78 (d, J=9.1 Hz, 1H), 2.01-2.26 (m, 3H), 3.04-3.17 (m, 2H), 3.32 (m, 3H), 3.45 (br.s., 2H), 4.41 (d, J=6.7 Hz, 1H), 4.91 (d, J=11.4 Hz, 1H), 5.06 (d, J=1.15 Hz, 1H), 6.19 (br.s., 2H), 7.33-7.46 (m, 5H); MS m/z 438 [M+H]$^+$.

Reference Example 5

(2S,5R)—N-(2-Aminoethoxy)-7-oxo-6-(sulfooxy)-1,6-diazabicyclo[3.2.1]octane-2-carboxamide (VII-1)

[Chemical Formula 43]

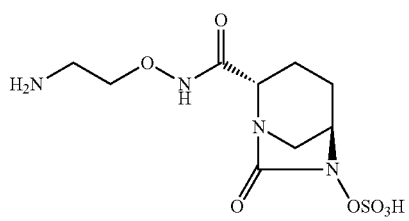

VII-1

Step 1 tert-Butyl{2-[({[(2S,5R)-6-benzyloxy-7-oxo-1,6-diazabicyclo[3.2.1]oct-2-yl]carbonyl}amino)oxy]ethyl}carbamate (IV-1)

A solution of (2S,5R)-6-(benzyloxy)-7-oxo-1,6-diazabicyclo[3.2.1]octane-2-carboxylic acid (4.30 g, 15.56 mmol) in dehydrated ethyl acetate (47 mL) was cooled to −30° C., and isobutyl chloroformate (2.17 g, washed with dehydrated ethyl acetate 1 mL) and triethylamine (1.61 g, washed with 1 mL of dehydrated ethyl acetate) were sequentially added dropwise at −30° C., followed by stirring for 1 hour. To the reaction solution was added a solution of tert-butyl 2-(aminooxy)ethylcarbamate (3.21 g) in dehydrated ethyl acetate (4 mL) (washed with 1 mL of dehydrated ethyl acetate), and the temperature of the mixture was elevated to 0° C. over 1.5 hours, followed by stirring overnight. The mixture was washed sequentially with 8% aqueous citric acid (56 mL), saturated sodium bicarbonate (40 mL), and saturated brine (40 mL), and dried over anhydrous magnesium sulfate. The mixture was then filtered, concentrated to 5 mL, and further substitution-concentrated with ethanol (10 mL) to 6 mL. To the resulting solution was added ethanol (3 mL) and hexane (8 mL), and the mixture was ice-cooled and seeded with crystals, followed by stirring for 15 minutes. To the mixture was added dropwise hexane (75 mL) over 2 hours, followed by stirring overnight. The crystalline material was filtered, washed with hexane, and dried in vacuo to afford 5.49 g of the title compound (net 4.98 g, yield 74%).

HPLC: COSMOSIL 5C18 MS-II 4.6×150 mm, 33.3 mM phosphate buffer/MeCN=50/50, 1.0 mL/min, UV 210 nm, RT 4.4 min; $^1$H NMR (400 MHz, CDCl$_3$) δ 1.44 (s, 9H), 1.56-1.70 (m, 1H), 1.90-2.09 (m, 2H), 2.25-2.38 (m, 1H), 2.76 (d, J=11.6 Hz, 1H), 3.03 (br.d, J=11.6 Hz, 1H), 3.24-3.47 (m, 3H), 3.84-4.01 (m, 3H), 4.90 (d, J=11.6 Hz, 1H), 5.05 (d, J=11.6 Hz, 1H), 5.44 (br.s., 1H), 7.34-7.48 (m, 5H), 9.37 (br.s., 1H); MS m/z 435 [M+H]$^+$.

Step 2 tert-Butyl{2-[({[(2S,5R)-6-hydroxy-7-oxo-1,6-diazabicyclo[3.2.1]oct-2-yl]carbonyl}amino)oxy]ethyl}carbamate (V-1)

To a solution of tert-butyl{2-[({[(2S,5R)-6-benzyloxy-7-oxo-1,6-diazabicyclo[3.2.1]oct-2-yl]carbonyl}amino)oxy]ethyl}carbamate (3.91 g, 9.01 mmol) in methanol (80 mL) was added a 10% palladium carbon catalyst (50% wet, 803 mg), followed by stirring for 45 minutes under hydrogen atmosphere. The reaction solution was filtered through a Celite pad and concentrated under reduced pressure to afford 3.11 g of the title compound (quantitative).

HPLC: COSMOSIL 5C18 MS-II 4.6×150 mm, 33.3 mM phosphate buffer/MeCN=75/25, 1.0 mL/min, UV 210 nm, RT 3.9 min; $^1$H NMR (400 MHz, CD$_3$OD) δ 1.44 (s, 9H), 1.73-1.83 (m, 1H), 1.86-1.99 (m, 1H), 2.01-2.12 (m, 1H), 2.22 (br.dd., J=15.0, 7.0 Hz, 1H), 3.03 (d, J=12.0 Hz, 1H), 3.12 (br.d., J=12.0 Hz, 1H), 3.25-3.35 (m, 2H), 3.68-3.71 (m, 1H), 3.82-3.91 (m, 3H); MS m/z 345 [M+H]$^+$.

Step 3

Tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}carbamate (VI-1)

To a solution of ted-butyl{2-[({[(2S,5R)-6-hydroxy-7-oxo-1,6-diazabicyclo[3.2.1]oct-2-yl]carbonyl}amino)oxy]ethyl}carbamate (3.09 g, 8.97 mmol) in dichloromethane (80 mL), 2,6-lutidine (3.20 mL) and sulfur trioxide-pyridine complex (3.58 g) were added, followed by stirring at room temperature overnight. The reaction solution was poured into semi-saturated sodium bicarbonate, and the aqueous layer was washed with chloroform. To the aqueous layer was added tetrabutylammonium hydrogensulfate (3.47 g) and chloroform (30 mL), followed by stirring for 10 minutes. After the aqueous layer was extracted with chloroform, the resulting organic layer was dried over anhydrous sodium sulfate, filtered, and then concentrated under reduced pressure to afford 5.46 g of the title compound (yield 91%).

HPLC: COSMOSIL 5C18 MS-II 4.6×150 mm, 33.3 mM phosphate buffer/MeCN=80/20, 1.0 mL/min, UV 210 nm, RT 2.0 min; $^1$H NMR (400 MHz, CDCl$_3$) δ 1.01 (t, J=7.4 Hz, 12H), 1.37-1.54 (m, 8H), 1.45 (s, 9H), 1.57-1.80 (m, 9H), 1.85-1.98 (m, 1H), 2.14-2.24 (m, 1H), 2.30-2.39 (m, 1H), 2.83 (d, J=11.6 Hz, 1H), 3.20-3.50 (m, 11H), 3.85-3.99 (m, 3H), 4.33-4.38 (m, 1H), 5.51 (br s, 1H), 9.44 (br.s., 1H); MS m/z 425 [M-Bu$_4$N+2H]$^+$.

Step 4

(2S,5R)—N-(2-Aminoethoxy)-7-oxo-6-(sulfooxy)-1,6-diazabicyclo[3.2.1]octane-2-carboxamide (VII-1)

To a solution of tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}carbamate (5.20 g, 7.82 mmol) in dichloromethane (25 mL), trifluoroacetic acid (25 mL) was added under ice-cooling, followed by stirring at 0° C. for 1 hour. The reaction solution was concentrated under reduced pressure. The resulting residue was washed with diethyl ether, adjusted to pH 7 with a sodium bicarbonate aqueous solution, purified by octadecylsilica gel column chromatography (water) and lyophilised to afford 1.44 g of the title compound (yield 57%).

HPLC: COSMOSIL 5C18 MS-II 4.6×150 mm, 33.3 mM phosphate buffer/MeCN=99/1, 1.0 mL/min, UV 210 nm, RT 3.1 min; $^1$H NMR (400 MHz, D$_2$O) δ 1.66-1.76 (m, 1H), 1.76-1.88 (m, 1H), 1.91-2.00 (m, 1H), 2.00-2.08 (m, 1H), 3.02 (d, J=12.0 Hz, 1H), 3.15 (t, J=5.0 Hz, 2H), 3.18 (br d, J=12.0 Hz, 1H), 3.95 (dd, J=7.8, 2.2 Hz, 1H), 4.04 (t, J=5.0 Hz, 2H), 4.07 (dd, J=6.4 & 3.2 Hz, 1H); MS m/z 325 [M+H]$^+$.

Reference Example 6

(2S,5R)—N-[2-(Methylamino)ethoxy]-7-oxo-6-(sulfooxy)-1,6-diazabicyclo[3.2.1]octane-2-carboxamide (VII-2)

[Chemical Formula 44]

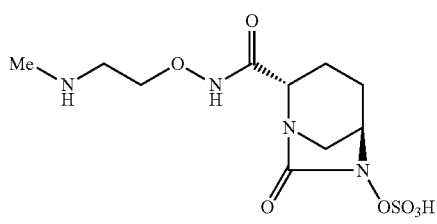

VII-2

Step 1 tert-Butyl{2-[({[(2S,5R)-6-benzyloxy-7-oxo-1,6-diazabicyclo[3.2.1]oct-2-yl]carbonyl}amino)oxy]ethyl}(methyl)carbamate (IV-2)

In a similar manner to Reference Example 5, a crude product was obtained from (2S,5R)-6-(benzyloxy)-7-oxo-1,6-diazabicyclo[3.2.1]octane-2-carboxylic acid (390 mg, 1.41 mmol) and tert-butyl(2-(aminooxy)ethyl)(methyl)carbamate (436 mg) and was then subjected to purification by silica gel column chromatography to afford 347.8 mg of the title compound (yield 55%).

$^1$H NMR (400 MHz, CDCl$_3$) δ 1.46 (s, 9H), 1.58-1.70 (m, 1H), 1.88-2.07 (m, 2H), 2.25-2.36 (m, 1H), 2.70-3.08 (m, 2H), 2.88 (s, 3H), 3.23-3.41 (m, 2H), 3.51-3.68 (m, 1H), 3.83-4.10 (m, 3H), 4.90 (d, J=11.4 Hz, 1H), 5.06 (d, J=11.4 Hz, 1H), 7.32-7.47 (m, 5H), 10.11 (br s, 1H); MS m/z 449 [M+H]$^+$.

Step 2 tert-Butyl{2-[({[(2S,5R)-6-hydroxy-7-oxo-1,6-diazabicyclo[3.2.1]oct-2-yl]carbonyl}amino)oxy]ethyl}(methyl) carbamate (V-2)

In a similar manner to Reference Example 5, the title compound was obtained from the total amount of the compound of Step 1 (quantitative).

$^1$H NMR (400 MHz, CD$_3$OD) δ 1.46 (s, 9H), 1.73-1.83 (m, 1H), 1.86-2.00 (m, 1H), 2.01-2.13 (m, 1H), 2.14-2.28 (m, 1H), 2.93 (s, 3H), 3.04 (d, J=10.8 Hz, 1H), 3.08-3.18 (m, 1H), 3.43-3.55 (m, 2H), 3.65-3.72 (m, 1H), 3.79-3.88 (m, 1H), 3.92-4.05 (m, 2H); MS m/z 359 [M+H]$^+$.

Step 3

(2S,5R)—N-[2-(Methylamino)ethoxy]-7-oxo-6-(sulfooxy)-1,6-diazabicyclo[3.2.1]octane-2-carboxamide (VII-2)

In a similar manner to Reference Example 5, tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}(methyl)carbamate was obtained from the total amount of the compound of Step 2 (quantitative).

$^1$H NMR (400 MHz, CDCl$_3$) δ 1.01 (t, J=7.2 Hz, 12H), 1.36-1.53 (m, 8H), 1.47 (s, 9H), 1.57-1.77 (m, 9H), 1.83-1.98 (m, 1H), 2.13-2.25 (m, 1H), 2.28-2.40 (m, 1H), 2.82-2.96 (m, 4H), 3.22-3.42 (m, 11H), 3.60-4.08 (m, 3H), 4.34 (br.s., 1H), 10.15 (br.s., 1H); MS m/z 437 [M-Bu$_4$N]$^-$.

The total amount of the above-mentioned tetrabutylammonium salt was deprotected with trifluoroacetic acid, and after purification by octadecylsilica gel column chromatography, 149.4 mu of the title compound was obtained (3 step yield 57%).

$^1$H NMR (500 MHz, D$_2$O) δ 1.73-1.97 (m, 2H), 1.98-2.07 (m, 1H), 2.08-2.18 (m, 1H), 2.74 (s, 3H), 3.09 (d, J=12.0 Hz, 1H), 3.21-3.32 (m, 3H), 4.04 (dd, J=7.5, 2.0 Hz, 1H), 4.10-4.23 (m, 3H); MS m/z 337 [M–H]$^+$.

Reference Example 7

(2S,5R)-7-Oxo-N-[2-(propan-2-ylamino)ethoxy]-6-(sulfooxy)-1,6-diazabicyclo[3.4.1]octane-2-carboxamide (VII-3)

[Chemical Formula 45]

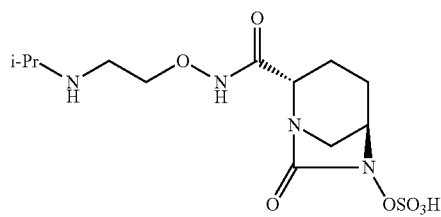

VII-3

Step 1 tert-Butyl{2-[({[(2S,5R)-6-benzyloxy-7-oxo-1,6-diazabicyclo[3.2.1]oct-2-yl]carbonyl}amino)oxy]ethyl}(propan-2-yl)carbamate (IV-3)

A solution of (2S,5R)-6-(benzyloxy)-7-oxo-1,6-diazabicyclo[3.2.1]octane-2-carboxylic acid (414 mg, 1.50 mmol) in dehydrated dichloromethane (14.1 mL) was cooled under argon atmosphere to 0° C., and to this were added sequentially isobutyl chloroformate (245.9 mg) and then triethylamine (197 mg), followed by stirring for 30 minutes. To this reaction mixture was added dropwise tert-butyl(2-(aminooxy)ethyl)(isopropyl)carbamate (596 mg). After completion of the addition, the temperature was elevated to room temperature, and the mixture was stirred for 1 hour. This reaction mixture was sequentially washed with 0.5 M hydrochloric acid and saturated brine, and the organic layer was dried over magnesium sulfate and concentrated under reduced pressure. The resulting residue was subjected to silica gel column chromatography to afford 578.4 mg of the title compound (yield 81%).

$^1$H NMR (400 MHz, CDCl$_3$) δ 1.15 (d, J=6.8 Hz, 6H), 1.46 (s, 9H), 1.55-1.70 (m, 1H), 1.89-2.07 (m, 2H), 2.25-2.37 (m, 1H), 2.73-2.90 (m, 1H), 2.98-3.08 (m, 1H), 3.22-3.38 (m, 2H), 3.40-3.60 (m, 1H), 3.83-4.06 (m, 4H), 4.90 (d, J=11.2 Hz, 1H), 5.06 (d, J=11.2 Hz, 1H), 7.35-7.46 (m, 5H), 10.29 (br.s., 1H); MS m/z 477 [M+H]$^+$.

Step 2 tert-Butyl{2-[({[(2S,5R)-6-hydroxy-7-oxo-1,6-diazabicyclo[3.2.1]oct-2-yl]carbonyl}amino)oxy]ethyl}(propan-2-yl)carbamate (V-3)

In a similar manner to Reference Example 5, the title compound was obtained from the total amount of compound of Step 1 (quantitative).

$^1$H NMR (400 MHz, CD$_3$OD) δ 1.09-1.23 (m, 6H), 1.46 (s, 9H), 1.73-2.27 (m, 4H), 3.06 (d, J=11.6 Hz, 1H), 3.08-3.50 (m, 4H), 3.64-3.73 (m, 1H), 3.79-3.98 (m, 3H); MS m/z 387 [M+H]$^+$.

Step 3

(2S,5R)-7-Oxo-N-[2-(propan-2-ylamino)ethoxy]-6-(sulfooxy)-1,6-diazabicyclo[3.2.1]octane-2-carboxamide (VII-3)

In a similar manner to Reference Example 5, tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}(propan-2-yl)carbamate was obtained from the total amount of the compound of Step 2 (quantitative).

$^1$H NMR (400 MHz, CDCl$_3$) δ 1.01 (d, J=7.4 Hz, 12H), 1.10-1.20 (m, 6H), 1.33-1.77 (m, 17H), 1.46 (s, 9H), 1.84-1.97 (m, 1H), 2.12-2.25 (m, 1H), 2.28-2.40 (m, 1H), 2.79-2.95 (m, 1H), 3.17-3.45 (m, 9H), 3.50-3.67 (m, 1H), 3.80-4.07 (m, 5H), 4.34 (br.s., 1H), 10.36 (br.s., 1H); MS m/z 465 [M-Bu$_4$N]$^-$.

The total amount of the above-mentioned tetrabutylammonium salt was deprotected with trifluoroacetic acid, and after purification by octadecylsilica gel column chromatography, 252.1 mg of the title compound was obtained (3 step yield 57%).

$^1$H NMR (500 MHz, D$_2$O) δ 1.28 (d, J=6.5 Hz, 6H), 1.74-1.83 (m, 1H), 1.85-1.96 (m, 1H), 1.98-2.14 (m, 2H), 3.11 (d, J=12.5 Hz, 1H), 3.22-3.30 (m, 3H), 3.40 (quint, J=6.5 Hz, 1H), 4.01 (br d, J=5.5 Hz, 1H), 4.09-4.18 (m, 3H); MS m/z 367 [M+H]$^+$.

Reference Example 8

(2S,5R)—N-[2-(Dimethylamino)ethoxy]-7-oxo-6-(sulfooxy)-1,6-diazabicyclo[3.2.1]octane-2-carboxamide (VII-4)

[Chemical Formula 46]

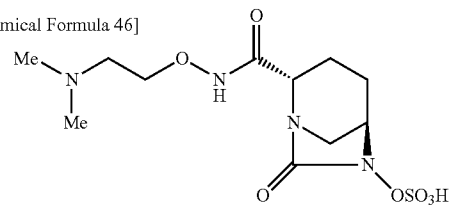

VII-4

Step 1

(2S,5R)-6-Benzyloxy-N-[2-(dimethylamino)ethoxy]-7-oxo-1,6-diazabicyclo[3.2.1]octane-2-carboxamide (IV-4)

A solution of (2S,5R)-6-(benzyloxy)-7-oxo-1,6-diazabicyclo[3.2.1]octane-2-carboxylic acid (553 mg, 2.00 mmol) in dehydrated dichloromethane (10 mL) was cooled to 0° C. under argon atmosphere, and isobutyl chloroformate (289 μL, 2.20 mmol) was added dropwise. Triethylamine (293 μL) was then added, and the mixture was stirred for 30 minutes to prepare a mixed acid anhydride in the reaction system. To this reaction mixture were added slowly 2-(aminooxy)-N,N-dimethylethanamine dihydrochloride (591 mg) and triethylamine (930 μL) while being washed with dehydrated dichloromethane (7.0 mL), followed by stirring for 1 hour at the same temperature. After filtering this reaction mixture, the residue was washed with methanol, and the filtrate was concentrated under reduced pressure. The resulting residue was dissolved in dichloromethane and water, and the organic layer extracted with dichloromethane was dried over magnesium sulfate and then concentrated under reduced pressure. The resulting residue was subjected to silica gel column chromatography (aminosilica, chloroform/methanol=10/1) to afford 291.1 mg of the title compound as a colorless oil (yield 40%).

$^1$H NMR (400 MHz, CDCl$_3$) δ 1.45-1.85 (m, 4H), 2.29 (s, 6H), 2.60 (t, J=5.2 Hz, 2H), 2.81 (d, J=11.6 Hz, 1H), 2.97 (br.d., J=11.6 Hz, 1H), 3.28-3.34 (m, 1H), 3.92-4.07 (m, 3H), 4.90 (d, J=11.6 Hz, 1H), 5.05 (d, J=11.6 Hz, 1H), 7.35-7.48 (m, 5H); MS m/z 363 [M+H]$^+$.

Step 2

(2S,5R)—N-[2-(Dimethylamino)ethoxy]-6-hydroxy-7-oxo-1,6-diazabicyclo[3.2.1]octane-2-carboxamide (V-4)

In a similar manner to Reference Example 5, the title compound was obtained from the total amount of the compound of Step 1 (quantitative).

$^1$H NMR (400 MHz, CDCl$_3$) δ 1.74-1.84 (m, 1H), 1.87-1.98 (m, 1H), 2.03-2.12 (m, 1H), 2.15-2.24 (m, 1H), 2.36 (s, 6H), 2.67-2.74 (m, 2H), 3.07 (br.d., J=11.6 Hz, 1H), 3.12 (br.d., J=11.6 Hz, 1H), 3.67-3.72 (m, 1H), 3.83 (br.d., J=6.4 Hz, 1H), 3.96-4.06 (m, 2H); MS m/z 273 [M+H]$^+$.

Step 3

(2S,5R)—N-[2-(Dimethylamino)ethoxy]-7-oxo-6-(sulfooxy)-1,6-diazabicyclo[3.2.1]octane-2-carboxamide (VII-4)

The reaction mixture obtained in a similar manner to Reference Example 5 was diluted with chloroform and washed with water to obtain pyridinium (2S,5R)—N-[2-(dimethylamino)ethoxy]-7-oxo-6-(sulfooxy)-1,6-diazabicyclo[3.2.1]octane-2-carboxamide. This was neutralized with saturated sodium bicarbonate water and then purified by octadecylsilica gel column chromatography to afford 130.7 mg of the title compound (2 step yield 43%).

$^1$H NMR (400 MHz, D$_2$O) δ 1.68-1.84 (m, 2H), 1.86-2.04 (m, 2H), 2.80 (s, 6H), 3.09-3.17 (m, 2H), 3.17-3.29 (m, 2H), 3.80-3.90 (m, 1H), 4.02-4.13 (m, 3H); MS m/z 353 [M+H]$^+$.

Reference Example 9

(2S,5R)—N-{[(2S)-2-Aminopropyl]oxy}-7-oxo-6-(sulfooxy)-1,6-diazabicyclo[3.2.1]octane-2-carboxamide (VII-5)

[Chemical Formula 47]

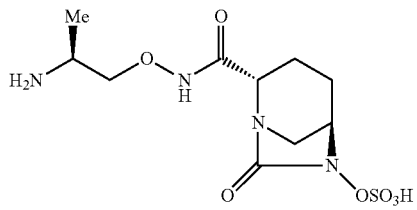

VII-5

Step 1 tert-Butyl{(2S)-1-[({[(2S,5R)-6-benzyloxy-7-oxo-1,6-diazabicyclo[3.2.1]oct-2-yl]carbonyl}amino)oxy]propan-2-yl}carbamate (IV-5)

In a similar manner to Reference Example 7, a crude product was obtained from (2S,5R)-6-(benzyloxy)-7-oxo-1,6-diazabicyclo[3.2.1]octane-2-carboxylic acid (414 mg, 1.50 mmol) and (S)-tert-butyl(1-(aminooxy)propan-2-yl)carbamate (550 mg) and was then subjected to purification by silica gel column chromatography to afford 585.6 mg of the title compound (yield 87%).

$^1$H NMR (400 MHz, CDCl$_3$) δ 1.17 (d, J=6.4 Hz, 3H), 1.44 (s, 9H), 1.55-1.70 (m, 1H), 1.90-2.10 (m, 2H), 2.26-2.34 (m, 1H), 2.80 (d, J=12.0 Hz, 1H), 3.06 (br.d., J=12.0 Hz, 1H), 3.27-3.34 (m, 1H), 3.64-3.74 (m, 1H), 3.86-3.98 (m, 3H), 4.81 (br.d., J=7.6 Hz, 1H), 4.90 (d, J=11.6 Hz, 1H), 5.05 (d, J=11.6 Hz, 1H), 7.34-7.45 (m, 5H), 9.60 (br.s., 1H); MS m/z 449 [M+H]$^+$.

Step 2 tert-Butyl{(2S)-1-[({[(2S,5R)-6-hydroxy-7-oxo-1,6-diazabicyclo[3.2.1]oct-2-yl]carbonyl}amino)oxy]propan-2-yl}carbamate (V-5)

In a similar manner to Reference Example 5, the title compound was obtained from the total amount of the compound of Step 1 (quantitative).

$^1$H NMR (400 MHz, CD$_3$OD) δ 1.16 (d, J=6.4 Hz, 3H), 1.44 (s, 9H), 1.74-1.84 (m, 1H), 1.86-1.98 (m, 1H), 2.03-2.12 (m, 1H), 2.21 (br.dd., J=15.2, 6.8 Hz, 1H), 3.06 (d, J=12.0 Hz, 1H), 3.14 (br.d., J=12.0 Hz, 1H), 3.68-3.72 (m, 1H), 3.74-3.87 (m, 4H); MS m/z 359 [M+H]$^+$.

Step 3

(2S,5R)—N-{[(2S)-2-aminopropyl]oxy}-7-oxo-6-(sulfooxy)-1,6-diazabicyclo[3.2.1]octane-2-carboxamide (VII-5)

In a similar manner to Reference Example 5, tetrabutylammonium tert-butyl{(2S)-1-[({[(2S,5R)-7-oxo-6-(sulfooxy)-1,6-diazabicyclo[3.2.1]oct-2-yl]carbonyl}amino)oxy]propan-2-yl}carbamate was obtained from the total amount of the compound of Step 2 (quantitative). MS m/z 437[M-Bu$_4$N]$^-$.

The total amount of the above-mentioned tetrabutylammonium salt was deprotected with trifluoroacetic acid, and after purification by octadecylsilica gel column chromatography, 117.1 mg of the title compound was obtained (3 step yield 26%).

$^1$H NMR (400 MHz, D$_2$O) δ 1.17 (d, J=6.8 Hz, 3H), 1.66-1.89 (m, 2H), 1.91-2.08 (m, 2H), 3.02 (d, J=12.0 Hz, 1H), 3.18 (br.d., J=12.0 Hz, 1H), 3.47-3.58 (m, 1H), 3.82 (dd, J=11.8, 9.4 Hz, 1H), 3.92-4.02 (m, 2H), 4.05-4.10 (m, 1H); MS m/z 339 [M+H]$^+$.

Reference Example 10

(2S,5R)—N-{[(2R)-2-Aminopropyl]oxy}-7-oxo-6-(sulfooxy)-1,6-diazabicyclo[3.2.1]octane-2-carboxamide (VII-6)

[Chemical Formula 48]

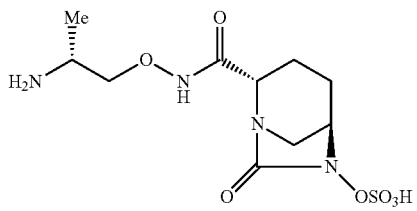

VII-6

Step 1 tert-Butyl {(2R)-1-[({[(2S,5R)-6-benzyloxy-7-oxo-1,6-diazabicyclo[3.2.1]oct-2-yl]carbonyl}amino)oxy]propan-2-yl}carbamate (IV-6)

In a similar manner to Reference Example 7, a crude product was obtained from (2S,5R)-6-(benzyloxy)-7-oxo-1,6-diazabicyclo[3.2.1]octane-2-carboxylic acid (414 mg, 1.50 mmol) and (R)-tert-butyl(1-(aminooxy)propan-2-yl)carbamate (569 mg) and was then subjected to purification by silica gel column chromatography to afford 625 mg of the title compound (yield 93%).

$^1$H NMR (400 MHz, CDCl$_3$) δ 1.14 (d, J=6.4 Hz, 3H), 1.43 (s, 9H), 1.53-1.70 (m, 1H), 1.90-2.06 (m, 2H), 2.28-2.36 (m, 1H), 2.79 (d, J=12.0 Hz, 1H), 3.02 (br.d., J=12.0 Hz, 1H), 3.28-3.33 (m, 1H), 3.56-3.68 (m, 1H), 3.84 (dd, J=11.2, 3.6 Hz, 1H), 3.92-4.04 (m, 2H), 4.66 (br d, J=8.0 Hz, 1H), 4.91 (d, J=11.2 Hz, 1H), 5.06 (d, J=11.2 Hz, 1H), 7.35-7.45 (m, 5H), 9.94 (br.s., 1H); MS m/z 449 [M+H]$^+$.

Step 2 tert-Butyl{(2R)-1-[({[(2S,5R)-6-hydroxy-7-oxo-1,6-diazabicyclo[3.2.1]oct-2-yl]carbonyl}amino)oxy]propan-2-yl}carbamate (V-6)

In a similar manner to Reference Example 5, the title compound was obtained from the total amount of the compound of Step 1 (quantitative).

$^1$H NMR (400 MHz, CD$_3$OD) δ 1.15 (d, J=6.4 Hz, 3H), 1.44 (s, 9H), 1.73-1.84 (m, 1H), 1.86-2.00 (m, 1H), 2.01-

2.12 (m, 1H), 2.19-2.29 (m, 1H), 3.06 (d, J=11.6 Hz, 1H), 3.10-3.20 (m, 1H), 3.67-3.72 (m, 1H), 3.73-3.92 (m, 4H); MS m/z 359 [M+H]⁺.

Step 3

(2S,5R)—N-{[(2R)-2-Aminopropyl]oxy}-7-oxo-6-(sulfooxy)-1,6-diazabicyclo[3.2.1]octane-2-carboxamide (VII-6)

In a similar manner to Reference Example 5, tetrabutylammonium tert-butyl{(2R)-1-[({[(2S,5R)-7-oxo-6-(sulfooxy)-1,6-diazabicyclo[3.2.1]oct-2-yl]carbonyl}amino)oxy]propan-2-yl}carbamate was obtained from the total amount of the compound of Step 2 (quantitative). MS m/z 437 [M-Bu₄N]⁻.

The total amount of the above-mentioned tetrabutylammonium salt was deprotected with trifluoroacetic acid, and after purification by octadecylsilica gel column chromatography, 212.6 mg of the title compound was obtained (3 step yield 45%).

¹H NMR (400 MHz, D₂O) δ 1.17 (d, J=6.8 Hz, 3H), 1.66-1.78 (m, 1H), 1.78-1.88 (m, 1H), 1.90-2.06 (m, 2H), 3.02 (d, J=12.0 Hz, 1H), 3.18 (br.d., J=12.0 Hz, 1H), 3.48-3.58 (m, 1H), 3.83 (dd, J=11.8, 9.0 Hz, 1H), 3.94 (br.d., J=7.2 Hz, 1H), 3.98 (dd, J=11.8, 3.4 Hz, 1H), 4.06-4.10 (m, 1H); MS m/z 339 [M+H]⁺.

Reference Example 11

(2S,5R)—N-(3-Aminopropoxy)-7-oxo-6-(sulfooxy)-1,6-diazabicyclo[3.2.1]octane-2-carboxamide (VII-7)

[Chemical Formula 49]

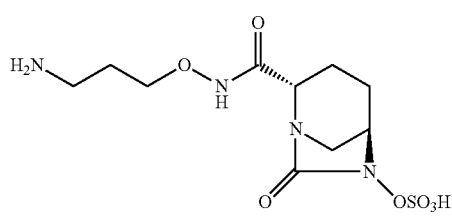

VII-7

Step 1 tert-Butyl{3-[({[(2S,5R)-6-benzyloxy-7-oxo-1,6-diazabicyclo[3.2.1]oct-2-yl]carbonyl}amino)oxy]propyl}carbamate (IV-7)

In a similar manner to Reference Example 5, a crude product was obtained from (2S,5R)-6-(benzyloxy)-7-oxo-1,6-diazabicyclo[3.2.1]octane-2-carboxylic acid (390 mg, 1.41 mmol) and tert-butyl(3-(aminooxy)propyl)carbamate (730 mg) and was then subjected to purification by silica gel column chromatography to afford 398.1 mg of the title compound (yield 63%).

¹H NMR (400 MHz, CDCl₃) δ 1.44 (s, 9H), 1.50-1.67 (m, 1H), 1.75-1.86 (m, 2H), 1.88-2.07 (m, 2H), 2.28-2.37 (m, 2H), 2.77 (d, J=11.0 Hz, 1H), 3.01 (br.d, J=11.0 Hz, 1H), 3.20-3.38 (m, 3H), 3.89-4.04 (m, 3H), 4.90 (d, J=11.4 Hz, 1H), 5.05 (d, J=11.4 Hz, 1H), 5.17 (br.s., 1H), 7.36-7.45 (m, 5H), 9.21 (br.s., 1H); MS m/z 449 [M+H]⁺.

Step 2 tert-Butyl{3-[({[(2S,5R)-6-hydroxy-7-oxo-1,6-diazabicyclo[3.2.1]oct-2-yl]carbonyl}amino)oxy]propyl}carbamate (V-7)

In a similar manner to Reference Example 5, the title compound was obtained from the compound of the above-mentioned Step 1 (392.8 mg, 876 µmol) (quantitative).

¹H NMR (400 MHz, CD₃OD) δ 1.43 (s, 9H), 1.73-1.99 (m, 4H), 2.01-2.12 (m, 1H), 2.13-2.24 (m, 1H), 3.07 (d, J=11.6 Hz, 1H), 3.09-3.21 (m, 3H), 3.69 (br.s., 1H), 3.80-3.96 (m, 3H); MS m/z 359 [M+H]⁺.

Step 3

(2S,5R)—N-(3-Aminopropoxy)-7-oxo-6-(sulfooxy)-1,6-diazabicyclo[3.2.1]octane-2-carboxamide In a similar manner to Reference Example 5, tetrabutylammonium tert-butyl{3-[({[(2S,5R)-7-oxo-6-(sulfooxy)-1,6-diazabicyclo[3.2.1]oct-2-yl]carbonyl}amino)oxy]propyl}carbamate was obtained from the total amount of the compound of Step 2 (quantitative).

¹H NMR (400 MHz, CDCl₃) δ 1.01 (t, J=7.4 Hz, 12H), 1.33-1.53 (m, 8H), 1.47 (s, 9H), 1.55-1.96 (m, 12H), 2.14-2.23 (m, 1H), 2.31-2.41 (m, 1H), 2.85 (br.d., J=11.2 Hz, 1H), 3.15-3.42 (m, 11H), 3.88-4.07 (m, 3H), 4.35 (br.s., 1H), 5.27 (br s, 1H), 9.26 (br.s., 1H); MS m/z 437 [M-Bu₄N]⁻.

The total amount of the above-mentioned tetrabutylammonium salt was deprotected with trifluoroacetic acid, and after purification by octadecylsilica gel column chromatography, 138.4 mg of the title compound was obtained (3 step yield 47%).

¹H NMR (400 MHz, D₂O) δ 1.67-2.05 (m, 6H), 3.00-3.19 (m, 4H), 3.82-3.94 (m, 3H), 4.05-4.10 (m, 1H); MS m/z 337 [M−H]⁻.

Reference Example 12

(2S,5R)—N-[(2S)-Azetidin-2-ylmethoxy]-7-oxo-6-(sulfooxy)-1,6-diazabicyclo[3.2.1]octane-2-carboxamide (VII-8)

[Chemical Formula 50]

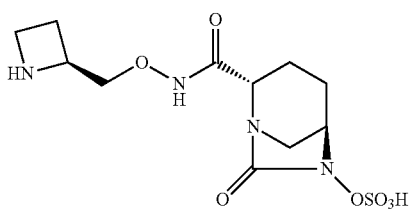

VII-8

Step 1 tert-Butyl(2S)-2-{[({[(2S,5R)-6-benzyloxy-7-oxo-1,6-diazabicyclo[3.2.1]oct-2-yl]carbonyl}amino)oxy]methyl}azetidine-1-carboxylate (IV-8)

In a similar manner to Reference Example 8, a crude product was obtained from (2S,5R)-6-(benzyloxy)-7-oxo-1, 6-diazabicyclo[3.2.1]octane-2-carboxylic acid (553 mg, 2.00 mmol) and (S)-tert-butyl 2-((aminooxy)methyl)azetidine-1-carboxylate (578 mg) and was then subjected to purification by silica gel column chromatography to afford 760.1 mg of the title compound (yield 83%).

$^1$H NMR (400 MHz, CDCl$_3$) δ 1.46 (s, 9H), 1.56-1.70 (m, 1H), 1.88-2.07 (m, 3H), 2.23-2.34 (m, 2H), 2.84 (d, J=11.6 Hz, 1H), 3.02 (d, J=11.6 Hz, 1H), 3.28 (br s, 1H), 3.77-4.03 (m, 4H), 4.06-4.15 (m, 1H), 4.37-4.48 (m, 1H), 4.89 (d, J=11.6 Hz, 1H), 5.04 (d, J=11.6 Hz, 1H), 7.34-7.44 (m, 5H), 10.63 (br.s., 1H); MS m/z 461 [M+H]$^+$.

Step 2 tert-Butyl(2S)-2-{[({[(2S,5R)-6-hydroxy-7-oxo-1,6-diazabicyclo[3.2.1]oct-2-yl]carbonyl}amino)oxy]methyl}azetidine-1-carboxylate (V-8)

In a similar manner to Reference Example 5, the title compound was obtained from the compound of the above-mentioned Step 1 (699 mg, 1.52 mmol) (quantitative).

$^1$H NMR (400 MHz, CD$_3$OD) δ 1.44 (s, 9H), 1.74-1.85 (m, 1H), 1.86-1.99 (m, 1H), 2.02-2.14 (m, 1H), 2.16-2.40 (m, 3H), 3.06 (d, J=11.6 Hz, 1H), 3.10-3.17 (m, 1H), 3.67-3.74 (m, 1H), 3.75-3.93 (m, 3H), 4.01 (dd, J=10.6, 10.6 Hz, 1H), 4.14 (dd, J=10.6, 10.6 Hz, 1H), 4.37-4.47 (m, 1H); MS m/z 371 [M+H]$^+$.

Step 3

(2S,5R)—N-[(2S)-Azetidin-2-ylmethoxy]-7-oxo-6-(sulfooxy)-1,6-diazabicyclo[3.2.1]octane-2-carboxamide (VII-8)

In a similar manner to Reference Example 5, tetrabutylammonium tert-butyl(2S)-2-{[({[(2S,5R)-7-oxo-6-(sulfooxy)-1,6-diazabicyclo[3.2.1]oct-2-yl]carbonyl}amino)oxy]methyl}azetidine-1-carboxylate was obtained from the total amount of the compound of Step 2 (quantitative).

$^1$H NMR (400 MHz, CDCl$_3$) δ 1.01 (t, J=7.2 Hz, 12H), 1.30-2.10 (m, 19H), 1.46 (s, 9H), 2.12-2.39 (m, 3H), 2.89 (br.d., J=12.0 Hz, 1H), 3.23-3.39 (m, 9H), 3.76-3.93 (m, 3H), 3.95-4.06 (m, 1H), 4.08-4.18 (m, 1H), 4.33 (br.s., 1H), 4.37-4.50 (m, 1H); MS m/z 449 [M-Bu$_4$N]$^-$.

The total amount of the above-mentioned tetrabutylammonium salt was deprotected with trifluoroacetic acid, and after purification by octadecylsilica gel column chromatography, 172.3 mg of the title compound was obtained (3 step yield 32%).

$^1$H NMR (500 MHz, D$_2$O) δ 1.71-1.83 (m, 1H), 1.84-1.97 (m, 1H), 1.98-2.16 (m, 2H), 2.36-2.49 (m, 1H), 2.50-2.61 (m, 1H), 3.10 (d, J=12.0 Hz, 1H), 3.22-3.30 (m, 1H), 3.92-4.12 (m, 5H), 4.25-4.36 (m, 1H), 4.68-4.77 (m, 1H); MS m/z 351 [M+H]$^+$.

Reference Example 13

(2S,5R)-7-Oxo-N-[(2R)-pyrrolidin-2-ylmethoxy]-6-(sulfooxy)-1,6-diazabicyclo[3.2.1]octane-2-carboxamide (VII-9)

[Chemical Formula 51]

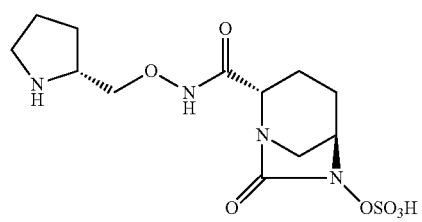

VII-9

Step 1 tert-Butyl(2R)-2-{[({[(2S,5R)-6-benzyloxy-7-oxo-1,6-diazabicyclo[3.2.1]oct-2-yl]carbonyl}amino)oxy]methyl}pyrrolidine-1-carboxylate (IV-9)

In a similar manner to Reference Example 5, a crude product was obtained from (2S,5R)-6-(benzyloxy)-7-oxo-1,6-diazabicyclo[3.2.1]octane-2-carboxylic acid (390 mg, 1.41 mmol) and (R)-tert-butyl 2-((aminooxy)methyl)pyrrolidine-1-carboxylate (796 mg) and was then subjected to purification by silica gel column chromatography to afford 336 mg of the title compound (yield 50%).

$^1$H NMR (400 MHz, CDCl$_3$) δ 1.45 (s, 9H), 1.52-1.72 (m, 1H), 1.80-2.09 (m, 6H), 2.27-2.39 (m, 1H), 2.84 (br.d., J=12.4 Hz, 1H), 2.96-3.08 (m, 1H), 3.28-3.44 (m, 3H), 3.60-3.86 (m, 2H), 3.89-4.06 (m, 1H), 4.14-4.29 (m, 1H), 4.90 (d, J=11.2 Hz, 1H), 5.06 (d, J=11.2 Hz, 1H), 7.32-7.47 (m, 5H), 10.56 (s, 1H); MS m/z 475 [M+H]$^+$.

Step 2 tert-Butyl(2R)-2-{[({[(2S,5R)-6-hydroxy-7-oxo-1,6-diazabicyclo[3.2.1]oct-2-yl]carbonyl}amino)oxy]methyl}pyrrolidine-1-carboxylate (V-9)

In a similar manner to Reference Example 5, the title compound was obtained from the total amount of the compound of Step 1 (quantitative).

$^1$H NMR (400 MHz, CD$_3$OD) δ 1.46 (s, 9H), 1.73-2.27 (m, 8H), 3.06 (d, J=11.6 Hz, 1H), 3.09-3.18 (m, 1H), 3.24-3.40 (m, 2H), 3.67-3.71 (m, 1H), 3.73-4.12 (m, 4H); MS m/z 385 [M+H]$^+$.

Step 3

(2S,5R)-7-Oxo-N-[(2R)-pyrrolidin-2-ylmethoxy]-6-(sulfooxy)-1,6-diazabicyclo[3.2.1]octane-2-carboxamide (VII-9)

In a similar manner to Reference Example 5, tetrabutylammonium tert-butyl(2R)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate was obtained from the total amount of the compound of Step 2 (quantitative).

$^1$H NMR (400 MHz, CDCl$_3$) δ 1.01 (t, J=7.4 Hz, 12H), 1.34-1.51 (m, 8H), 1.46 (s, 9H), 1.55-1.78 (m, 10H), 1.80-2.01 (m, 4H), 2.11-2.23 (m, 1H), 2.29-2.42 (m, 1H), 2.88 (br.d., J=11.2 Hz, 1H), 3.21-3.43 (m, 10H), 3.60-3.86 (m, 2H), 3.88-4.07 (m, 2H), 4.16-4.28 (m, 1H), 4.34 (br.s., 1H), 10.62 (br s, 1H); MS m/z 463 [M-Bu$_4$N+2H]$^+$.

The total amount of the above-mentioned tetrabutylammonium salt was deprotected with trifluoroacetic acid, and after purification by octadecylsilica gel column chromatography, 77.4 mg of the title compound was obtained (3 step yield 30%).

$^1$H NMR (500 MHz, D$_2$O) δ 1.66-2.18 (m, 8H), 3.14 (d, J=12.8 Hz, 1H), 3.23 (br.d. J=12.8 Hz, 1H), 3.30 (t, J=7.3 Hz, 2H), 3.89 (ddd, J=8.2, 8.2, 3.4 Hz, 1H), 3.92-4.01 (m, 2H), 4.09-4.18 (m, 2H); MS m/z 365 [M+H]$^+$.

Reference Example 14

(2S,5R)-7-Oxo-N-[(3R)-piperidin-3-ylmethoxy]-6-(sulfooxy)-1,6-diazabicyclo[3.2.1]octane-2-carboxamide (VII-10)

[Chemical Formula 52]

VII-10

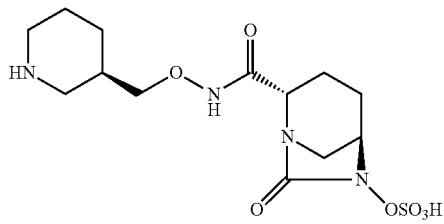

Step 1 tert-Butyl(3R)-3-{[({[(2S,5R)-6-benzyloxy-7-oxo-1,6-diazabicyclo[3.2.1]oct-2-yl]carbonyl}amino)oxy]methyl}piperidine-1-carboxylate (IV-10)

In a similar manner to Reference Example 8, a crude product was obtained from (2S,5R)-6-(benzyloxy)-7-oxo-1,6-diazabicyclo[3.2.1]octane-2-carboxylic acid (390 mg, 1.41 mmol) and (R)-tert-butyl 3-((aminooxy)methyl)piperidine-1-carboxylate (527 mg) and was then subjected to purification by silica gel column chromatography to afford 333 mg of the title compound (yield 48%).

$^1$H NMR (400 MHz, CDCl$_3$) δ 1.15-2.10 (m, 8H), 1.45 (s, 9H), 2.25-2.40 (m, 1H), 2.70-3.08 (m, 4H), 3.27-3.37 (m, 1H), 3.65-4.00 (m, 5H), 4.90 (d, J=11.2 Hz, 1H), 5.05 (d, J=11.2 Hz, 1H), 7.34-7.46 (m, 5H), 9.22 (br.s., 1H); MS m/z 489 [M+H]$^+$.

Step 2 tert-Butyl(3R)-3-{[({[(2S,5R)-6-hydroxy-7-oxo-1,6-diazabicyclo[3.2.1]oct-2-yl]carbonyl}amino)oxy]methyl}piperidine-1-carboxylate (V-10)

In a similar manner to Reference Example 5, the title compound was obtained from the total amount of the compound of Step 1 (quantitative).

$^1$H NMR (400 MHz, CD$_3$OD) δ 1.24-1.37 (m, 1H), 1.40-1.56 (m, 1H), 1.45 (s, 9H), 1.64-1.73 (m, 1H), 1.75-2.00 (m, 4H), 2.03-2.13 (m, 1H), 2.15-2.26 (m, 1H), 2.65-2.95 (m, 2H), 3.06 (d, J=12.0 Hz, 1H), 3.13 (br.d., J=12.0 Hz, 1H), 3.67-3.91 (m, 5H), 4.01-4.08 (m, 1H), MS m/z 399 [M+H]$^+$.

Step 3

(2S,5R)-7-Oxo-N-[(3R)-piperidin-3-ylmethoxy]-6-(sulfooxy)-1,6-diazabicyclo[3.2.1]octane-2-carboxamide (VII-10)

In a similar manner to Reference Example 5, tetrabutylammonium tert-butyl(3R)-2-{[({[(2S,5R)-7-oxo-6-(sulfooxy)-1,6-diazabicyclo[3.2.1]oct-2-yl]carbonyl}amino)oxy]methyl}piperidine-1-carboxylate was obtained from the total amount of the compound of Step 2 (quantitative).

$^1$H NMR (400 MHz, CDCl$_3$) δ 1.01 (dd, J=7.6&6.8 Hz, 12H), 1.11-1.99 (m, 23H), 1.46 (s, 9H), 2.12-2.24 (m, 1H), 2.30-2.42 (m, 1H), 2.67-2.96 (m, 3H), 3.19-3.38 (m, 9H), 3.70-3.99 (m, 5H), 4.35 (br.s., 1H), 9.16 (br.s., 1H); MS m/z 477 [M-Bu$_4$N]$^-$.

The total e amount of the above-mentioned tetrabutylammonium salt was deprotected with trifluoroacetic acid, and after purification by octadecylsilica gel column chromatography, 106 mg of the title compound was obtained (3 step yield 41%).

$^1$H NMR (400 MHz, D$_2$O) δ 1.16-1.28 (m, 1H), 1.54-1.88 (m, 5H), 1.92-2.16 (m, 3H), 2.72 (t, J=12.2 Hz, 1H), 2.81 (ddd, J=12.8&12.8&3.5 Hz, 1H), 3.02 (d, J=12.0 Hz, 1H), 3.15-3.28 (m, 2H), 3.37-3.44 (m, 1H), 3.70 (dd, J=10.3&7.6 Hz, 1H), 3.79 (dd, J=10.3&5.0 Hz, 1H), 3.88-3.94 (m, 1H), 4.06-4.10 (m, 1H); MS m/z 377 [M–H]$^-$.

Reference Example 15

(2S,5R)-7-Oxo-N-[(3S)-pyrrolidin-3-yloxy]-6-(sulfooxy)-1,6-diazabicyclo[3.2.1]octane-2-carboxamide (VII-11)

[Chemical Formula 53]

VII-11

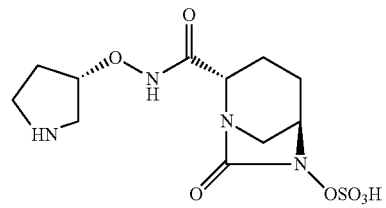

Step 1 tert-Butyl(3S)-3-[({[(2S,5R)-6-benzyloxy-7-oxo-1,6-diazabicyclo[3.2.1]oct-2-yl]carbonyl}amino)oxy]pyrrolidine-1-carboxylate (IV-11)

In a similar manner to Reference Example 5, a crude product obtained from (2S,5R)-6-(benzyloxy)-7-oxo-1,6-diazabicyclo[3.2.1]octane-2-carboxylic acid (553 mg, 2.00 mmol) and (S)-tert-butyl 3-(aminooxy)pyrrolidine-1-carboxylate (606 mg) was subjected to purification by silica gel column chromatography to afford 920.4 mg of the title compound (quantitative).

$^1$H NMR (400 MHz, CDCl$_3$) δ 1.46 (s, 9H), 1.61-1.68 (m, 1H), 1.89-2.09 (m, 3H), 2.15-2.19 (m, 1H), 2.28-2.34 (m, 1H), 2.75 (d, J=11.6 Hz, 1H), 2.95-3.06 (m, 1H), 3.31 (br s, 1H), 3.35-3.68 (m, 4H), 3.97 (d, J=7.6 Hz, 1H), 4.60 (br.d., J=23.2 Hz, 1H), 4.90 (d, J=11.6 Hz, 1H), 5.05 (d, J=11.6 Hz, 1H), 7.26-7.43 (m, 5H), 9.08 (br.d., J=23.2 Hz, 1H); MS m/z 461 [M+H]$^+$.

Step 2 tert-Butyl(3S)-3-[({[(2S,5R)-6-hydroxy-7-oxo-1,6-diazabicyclo[3.2.1]oct-2-yl]carbonyl}amino)oxy]pyrrolidine-1-carboxylate (V-11)

In a similar manner to Reference Example 5, the title compound was obtained from the compound of the above-mentioned Step 1 (869 mg, 1.89 mmol) (quantitative).

¹H NMR (400 MHz, CD₃OD) δ 1.47 (s, 9H), 1.75-2.12 (m, 4H), 2.13-2.25 (m, 2H), 3.05 (d, J=12.0 Hz, 1H), 3.13 (br.d., J=12.0 Hz, 1H), 3.25-3.50 (m, 2H), 3.61 (br.d., J=13.2 Hz, 1H), 3.70 (br.s., 1H), 3.86 (br d, J=7.2 Hz, 1H), 4.32-4.38 (m, 1H), 4.54-4.62 (m, 1H); MS m/z 371 [M+H]⁺.

Step 3

(2S,5R)-7-Oxo-N-[(3S)-pyrrolidin-3-yloxy]-6-(sulfooxy)-1,6-diazabicyclo[3.2.1]octane-2-carboxamide (VII-11)

In a similar manner to Reference Example 5, tetrabutylammonium tert-butyl(3S)-3-[({[(2S,5R)-7-oxo-6-(sulfooxy)-1,6-diazabicyclo[3.2.1]oct-2-yl]carbonyl}amino)oxy]pyrrolidine-1-carboxylate (quantitative) was obtained from the total amount of the compound of Step 2. MS m/z 449 [M-Bu₄N]⁻.

The total amount of the above-mentioned tetrabutylammonium salt was deprotected with trifluoroacetic acid, and after purification by octadecylsilica gel column chromatography, 170.7 mg of the title compound was obtained (3 step yield 26%).

¹H NMR (400 MHz, D₂O) δ 1.71-1.92 (m, 2H), 1.95-2.18 (m, 3H), 2.21-2.30 (m, 1H), 3.07 (d., J=12.2 Hz, 1H), 3.24 (br.d., J=12.2 Hz, 1H), 3.31-3.45 (m, 3H), 3.51 (d, J=13.6 Hz, 1H), 3.99 (br.d., J=6.0 Hz, 1H), 4.10-4.14 (m, 1H), 4.72-4.77 (m, 1H); MS m/z 349 [M−H]⁻.

Reference Example 16

(2S,5R)—N-(Azetidin-3-yl methoxy)-7-oxo-6-(sulfooxy)-1,6-diazabicyclo[3.2.1]octane-2-carboxamide (VII-12)

[Chemical Formula 54]

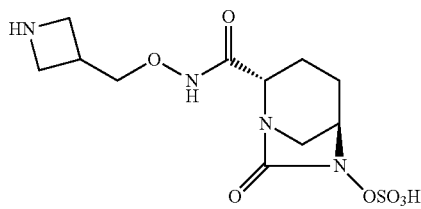

VII-12

Step 1 tert-Butyl 3-{[({[(2S,5R)-6-benzyloxy-7-oxo-1,6-diazabicyclo[3.2.1]oct-2-yl]carbonyl}amino)oxy]methyl}azetidine-1-carboxylate (IV-12)

In a similar manner to Reference Example 8, a crude product obtained from (2S,5R)-6-(benzyloxy)-7-oxo-1,6-diazabicyclo[3.2.1]octane-2-carboxylic acid (553 mg, 2.00 mmol) and tert-butyl 3-((aminooxy)methyl)azetidine-1-carboxylate (564 mg) was subjected to purification by silica gel column chromatography to afford 699.7 mg of the title compound (yield 76%).

¹H NMR (400 MHz, CDCl₃) δ 1.43 (s, 9H), 1.54-1.70 (m, 1H), 1.87-2.06 (m, 2H), 2.27-2.35 (m, 1H), 2.75 (d, J=11.6 Hz, 1H), 2.80-2.90 (m, 1H), 3.01 (br.d., J=11.6 Hz, 1H), 3.32 (br.s., 1H), 3.68-3.76 (m, 2H), 3.94 (br.d., J=7.6 Hz, 1H), 4.00-4.15 (m, 4H), 4.90 (d, J=11.8 Hz, 1H), 5.05 (d, J=11.8 Hz, 1H), 7.35-7.44 (m, 5H), 9.08 (br s, 1H); MS m/z 461 [M+H]⁺.

Step 2 tert-Butyl 3-{[({[(2S,5R)-6-hydroxy-7-oxo-1,6-diazabicyclo[3.2.1]oct-2-yl]carbonyl}amino)oxy]methyl}azetidine-1-carboxylate (V-12)

In a similar manner to Reference Example 5, the title compound was obtained from the compound of the above-mentioned Step 1 (642 mg, 1.39 mmol) (quantitative).

¹H NMR (400 MHz, CD₃OD) δ 1.43 (s, 9H), 1.74-1.85 (m, 1H), 1.86-1.97 (m, 1H), 2.04-2.13 (m, 1H), 2.16-2.24 (m, 1H), 2.84-2.94 (m, 1H), 3.05 (d, J=11.6 Hz, 1H), 3.13 (br.d., J=11.6 Hz, 1H), 3.68-3.82 (m, 3H), 3.83 (br.d., J=6.8 Hz, 1H), 3.97-4.06 (m, 4H); MS m/z 371 [M+H]⁺.

Step 3

(2S,5R)—N-(Azetidin-3-ylmethoxy)-7-oxo-6-(sulfooxy)-1,6-diazabicyclo[3.2.1]octane-2-carboxamide (VII-12)

In a similar manner to Reference Example 5, tetrabutylammonium tert-butyl 3-{[({[(2S,5R)-7-oxo-6-(sulfooxy)-1,6-diazabicyclo[3.2.1]oct-2-yl]carbonyl}amino)oxy]methyl}azetidine-1-carboxylate was obtained from the total amount of the compound of Step 2 (quantitative).

¹H NMR (400 MHz, CDCl₃) δ 1.01 (t, J=7.2 Hz, 12H), 1.37-1.51 (m, 8H), 1.46 (s, 9H), 1.54-1.75 (m, 9H), 1.82-1.97 (m, 1H), 2.13-2.25 (m, 1H), 2.29-2.40 (m, 1H), 2.77-2.95 (m, 2H), 3.24-3.40 (m, 9H), 3.64-4.16 (m, 7H), 4.36 (br.s., 1H), 9.16 (br.s., 1H); MS m/z 449 [M-Bu₄N]⁻.

The total amount of the above-mentioned tetrabutylammonium salt was deprotected with trifluoroacetic acid, and after purification by octadecylsilica gel column chromatography, 164.7 mg of the title compound was Obtained (3 step yield 34%).

¹H NMR (400 MHz, D₂O) δ 1.65-1.89 (m, 2H), 1.92-2.06 (m, 2H), 3.06 (d, J=12.4 Hz, 1H), 3.10-3.22 (m, 2H), 3.90-4.00 (m, 5H), 4.07-4.14 (m, 3H); MS m/z 351 [M+H]⁺.

Reference Example 17

(3aR,7aS)-2-Hydroxy-3a,4,7,7a-tetrahydro-1H-isoindol-1,3(2H)-dione

[Chemical Formula 55]

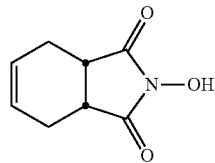

Hydroxylamine sulfate (24.975 g, 0.152 mol) was dissolved in water (100 mL), and (3aR,7aS)-3a,4,7,7a-tetrahydroisobenzofuran-1,3-dione (45.228 g) was added. To the mixture was added a 25% aqueous sodium hydroxide solution (50 g) in small portions over 15 minutes, followed by stirring at 90° C. for 2 hours. The mixture was cooled to room temperature. The precipitated crystalline-solid was suction-filtered, followed by deliquoring for 30 minutes. The wet crystals were vacuum dried at 50° C. for 2 days to afford 42.87 g of the title compound (yield 87%).

$^1$H NMR (400 MHz, CDCl$_3$) δ 2.20-2.31 (m, 2H), 2.56-2.65 (m, 2H), 3.08-3.14 (m, 2H), 5.91 (dt, J=0.9, 2.7 Hz, 2H); MS m/z 166 [M−H]$^−$.

Reference Example 18

(3aR,7aS)-1,3-Dioxo-3a,4,7,7a-tetrahydro-1H-isoindol-2(3H)-yl(2S,5R)-6-(benzyloxy)-7-oxo-1,6-diazabicyclo[3.2.1]octane-2-carboxylate

[Chemical Formula 56]

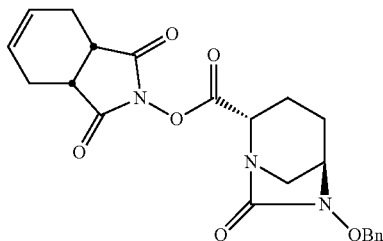

Step 1

1-tert-Butyl 2-((3aR,7aS)-1,3-dioxo-3a,4,7,7a-tetrahydro-1H-isoindol-2(3H)-yl)(2S,5R)-5-((benzyloxy)amino)piperidine-1,2-dicarboxylate

[Chemical Formula 57]

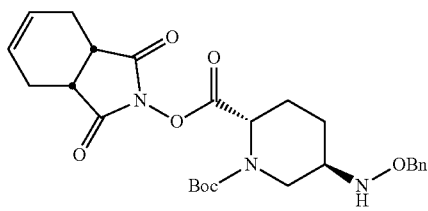

(2S,5R)-5-((Benzyloxy)amino)-1-(tert-butoxycarbonyl)piperidine-2-carboxylic acid (Reference Example 3, Step 1, 3.504 g, 10 mmol) was dissolved in dehydrated tetrahydrofuran (50 mL), followed by cooling to about −20° C. To the mixture were added dropwise isobutyl chloroformate (1.51 g) and then triethylamine (2.17 g), followed by stirring at the same temperature for 15 minutes. Then, to the reaction solution was added (3aR,7aS)-2-hydroxy-3a4,7,7a-tetrahydro-1H-isoindol-1,3(2H)-dione (Reference Example 17, 1.84 g), followed by stirring at the same temperature for 30 minutes and then at room temperature for 30 minutes. The reaction solution was diluted with ethyl acetate (200 mL), washed sequentially with ice-cold 10% citric acid (60 mL), saturated sodium bicarbonate (60 mL), and saturated brine (60 mL), dried over anhydrous magnesium sulfate, and filtered. The residue obtained by concentrating the filtrate under reduced pressure was subjected to silica gel column chromatography (hexane/ethyl acetate=2/1) to afford 4.689 g of the title compound as a colorless foamy solid (yield 94%).

$^1$H NMR (400 MHz, CDCl$_3$) δ1.47 (bs, 9H), 1.59-1.75 (m, 2H), 2.04-2.32 (m, 2H), 2.16-2.35 (m, 2H), 2.61 (d, J=15.2 Hz, 2H), 3.14-3.24 (m, 4H), 4.15-4.22 (m, 1H), 4.71 (q, J=11.6 Hz, 2H), 5.03 (bs, 1H), 5.97 (bs, 2H), 7.26-7.38 (m, 5H); MS m/z 500 [M+H]$^+$.

Step 2

The compound of the above-mentioned Step 1 (4.689 g, 9.386 mmol) was dissolved in dehydrated chloroform (50 mL), and triethylamine (1.40 g) was added, followed by ice-cooling. To the mixture was added triphosgene (1.09 g), followed by stirring for 0.5 hours, and the completion of the reaction for the title compound was confirmed by TLC. To the mixture was added methanol (0.255 mL) under ice-cooling, followed by stirring for 30 minutes. Subsequently, methanesulfonic acid (8.89 g) was added, followed by stirring for 30 minutes. The completion of the reaction for the title compound was confirmed by TLC. The mixture was added dropwise to an ice-cold 1 M aqueous potassium hydrogencarbonate solution (11.1 g/100 mL), followed by stirring for 0.5 hours. Chloroform (30 mL) was then added to separate the layers. The organic layer was washed sequentially with 1M hydrochloric acid (70 mL), saturated sodium bicarbonate (70 mL), and saturated brine (70 mL), dried over anhydrous magnesium sulfate, filtered and concentrated under reduced pressure. The residue is dissolved in chloroform (16 mL), and hexane (24 mL) was added, followed by stirring for 15 minutes. Further, hexane (8 mL) was added followed by stirring and aging for 15 minutes. The precipitated solid was filtered off, washed with a mixture of chloroform/hexane (2/3), and dried under reduced pressure to afford 3.51 g of the title compound as a colorless crystalline powder (yield 88%).

$^1$H NMR (400 MHz, CDCl$_3$) δ 1.67-1.77 (m, 1H), 2.08 (d, J=14.2 Hz, 1H), 2.14-2.26 (m, 2H), 2.30 (d, J=13.8 Hz, 2H), 2.55-2.66 (m, 2H), 3.10-3.24 (m, 4H), 3.34 (bs, 1H), 4.45 (d, J=6.4 Hz, 1H), 4.91 (d, J=11.2 Hz, 1H), 5.06 (d, J=11.4 Hz, 1H), 5.97 (bs, 2H), 7.34-7.45 (m, 5H); MS m/z 426 [M+H]$^+$.

Reference Example 19

(3aR,7aS)-2-Hydroxyhexahydro-1H-isoindol-1,3(2H-dione

[Chemical Formula 58]

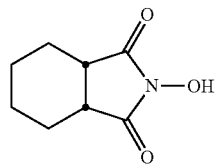

Hydroxylamine sulfate (24.975 g, 0.152 mol) was dissolved in water (75 mL), and (3aR,7aS)-hexahydroisobenzofuran-1,3-dione (48.000 g) was added. To the mixture was added a 25% aqueous sodium hydroxide solution (50 g) in small portions over 15 minutes, followed by stirring at 90° C. for 1 hour. The mixture was cooled to room temperature, extracted twice with chloroform 50 mL, dried over anhydrous sodium sulfate and filtered. The filtrate was concentrated under reduced pressure, the residue was dissolved in chloroform, impurities were filtered out, and the solvent was concentrated under reduced pressure. The residue was dissolved by adding ethyl acetate, the solution was concentrated under reduced pressure and it was dried in vacuo for further 2 days to afford 49.35 g of the title compound as a colorless solid (yield 94%).

$^1$H NMR (400 MHz, CDCl$_3$) δ 1.45 (dt, J=3.0, 5.9 Hz, 4H), 1.71-1.90 (m, 4H), 2.84-2.92 (m, 2H), 6.01 (brs, 1H); MS m/z 168 [M−H]$^−$.

Reference Example 20

(3aR,7aS)-1,3-Dioxohexahydro-1H-isoindol-2(3H)-yl(2S,5R)-6-(benzyloxy)-7-oxo-1,6-diazabicyclo[3.2.1]octane-2-carboxylate

[Chemical Formula 59]

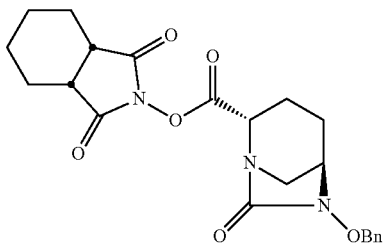

Step 1

1-tert-Butyl 2-((3aR,7aS)-1,3-dioxohexahydro-1H-isoindol-2(3H)-yl)(2S,5R)-5-((benzyloxy)amino)piperidine-1,2-dicarboxylate

[Chemical Formula 60]

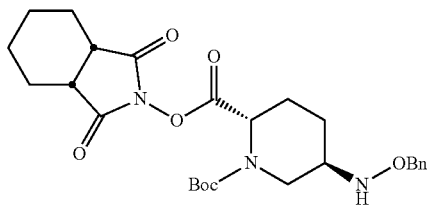

(2S,5R)-5-((Benzyloxy)amino)-1-(tert-butoxycarbonyl)piperidine-2-carboxylic acid (Reference Example 3, Step 1, 3.504 g, 10 mmol) was dissolved in dehydrated tetrahydrofuran (50 mL), followed by cooling to about −20° C. To the mixture were added dropwise isobutyl chloroformate (1.51 g) and then triethylamine (2.17 g), followed by stirring at the same temperature for 15 minutes. Then, to the reaction solution was added (3aR,7aS)-2-hydroxyhexahydro-1H-isoindol-1,3(2H)-dione (Reference Example 19, 1.86 g), followed by stirring at the same temperature for 30 minutes and then at room temperature for 30 minutes. The reaction solution was diluted with ethyl acetate (200 mL), washed sequentially with ice-cold 10% citric acid (60 mL), saturated sodium bicarbonate (60 mL), and saturated brine (60 mL), dried over anhydrous magnesium sulfate, and filtered. The residue obtained by concentrating the filtrate under reduced pressure was subjected to silica gel column chromatography (hexane/ethyl acetate=2/1) to afford 4.521 g of the title compound as a colorless foamy solid (yield 90%).

$^1$H NMR (400 MHz, CDCl$_3$) δ 1.35-1.58 (m, 13H), 1.62 (bs, 1H), 1.76 (bs, 2H), 1.90 (bs, 4H), 1.95-2.15 (m, 2H), 3.00 (bs, 2H), 3.15-3.30 (m, 2H), 4.16-4.25 (m, 1H), 4.72 (q, J=11.6 Hz, 2H), 5.30-5.53 (m, 1H), 7.26-7.38 (m, 5H); MS m/z 502 [M+H]$^+$.

Step 2

The compound of the above-mentioned Step 1 (4.521 g, 9.01 mmol) was dissolved in dehydrated chloroform (50 mL), and triethylamine (1.350 g) was added, followed by ice-cooling. To the mixture was added triphosgene (1.043 g), followed by stirring for 0.5 hours, and the completion of the reaction for the title compound was confirmed by TLC. To the mixture was added methanol (0.245 mL) under ice-cooling, followed by stirring for 30 minutes. Subsequently, methanesulfonic acid (8.53 g) was added, followed by stirring for 30 minutes. The completion of the reaction for the title compound was confirmed by TLC. The mixture was added dropwise to an ice-cold 1M aqueous potassium hydrogencarbonate solution (10.668 g/90 mL), followed by stirring for 0.5 hours. Chloroform (33 mL) was then added to separate the layers. The organic layer was washed sequentially with 1M hydrochloric acid (70 mL), saturated sodium bicarbonate (70 and saturated brine (70 mL), dried over anhydrous magnesium sulfate, filtered and concentrated under reduced pressure. The residue was subjected to silica gel column chromatography (chloroform/ethyl acetate=6/1) to afford 3.106 g of the title compound as a colorless solid (yield 81%).

$^1$H NMR (400 MHz, CDCl$_3$) δ1.50 (bs, 4H), 1.62 (bs, 1H), 1.68-1.84 (m, 1H), 1.91 (bs, 4H), 2.04-2.27 (m, 2H), 3.02 (bs, 2H), 3.15 (s, 2H), 3.35 (bs, 1H), 4.47 (d, 6.6 Hz, 1H), 4.92 (d, J=11.2 Hz, 1H), 5.07 (d, J=11.4 Hz, 1H), 7.34-7.45 (m, 5H); MS m/z 428 [M+H]$^+$.

Example 1 tert-Butyl{2-[({[(2S,5R)-6-benzyloxy-7-oxo-1,6-diazabicyclo[3.2.1]oct-2-yl]carbonyl}amino)oxy]ethyl}carbamate (IV-1)

Example 1a

[Chemical Formula 61]

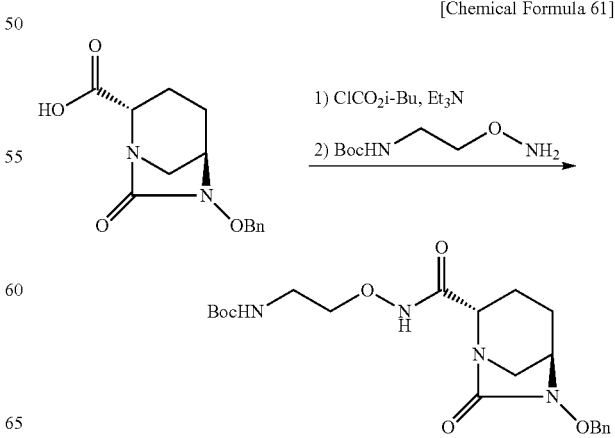

A solution of (2S,5R)-6-(benzyloxy)-7-oxo-1,6-diazabicyclo[3.2.1]octane-2-carboxylic acid (4.80 kg, 17.373 mol) in dehydrated ethyl acetate (62 L) was cooled to −30° C., isobutyl chloroformate (2.52 kg) and triethylamine (1.85 kg) were sequentially added dropwise, followed by stirring at −30° C. for 15 minutes. To the reaction solution was added a solution of tert-butyl 2-(aminooxy)ethylcarbamate in dehydrated ethyl acetate (15 wt %, 23.45 kg) over 30 minutes (washed with 2 L of dehydrated ethyl acetate), and the temperature was elevated to 0° C. over 1 hour. The mixture was washed sequentially with 8% citric acid (65 L), 5% sodium bicarbonate (60 L), and water (60 L), and concentrated to 24 L. To the concentrate was added ethyl acetate (24 L), and the mixture was substitution-concentrated twice to 24 L. To the resulting concentrate was added ethyl acetate (29 L) and hexane (72 L), followed by stirring overnight. To the mixture was added dropwise hexane (82 L), followed by stirring for 2 hours. The precipitated crystals were filtered, washed with hexane, and dried in vacuo to afford 5.51 kg of the title compound (yield 76%). Instrumental data were consistent with those of Reference Example 5, Step 1.

Example 1b

[Chemical Formula 62]

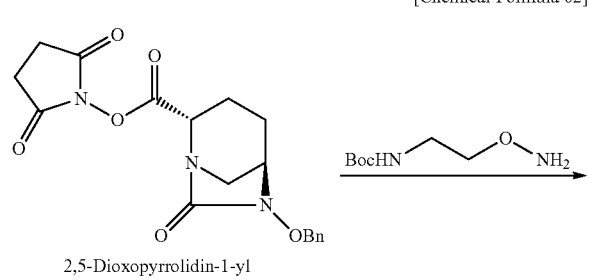

2,5-Dioxopyrrolidin-1-yl (2S,5R)-6-(benzyloxy)-7-oxo-1,6-diazabicyclo[3.2.1]octane-2-carboxylate (Reference Example 3, 373 mg, 1 mmol) was dissolved in dehydrated dichloromethane (5 mL), and to this was added a solution of tert-butyl 2-(aminooxy)ethylcarbamate (194 mg) in dehydrated dichloromethane (2 mL, washed with 1 mL) under ice-cooling, followed by stirring for 1 hour. The reaction solution was diluted with ethyl acetate (65 mL), washed sequentially with 10% citric acid (20 mL), saturated sodium bicarbonate (20 mL), and saturated brine (20 mL), dried over anhydrous magnesium sulfate, filtered, and concentrated under reduced pressure to afford 362 mg of the title compound (yield 83%). Instrumental data were consistent with those of the compound of Reference Example 5, Step 1.

Example 1c

[Chemical Formula 63]

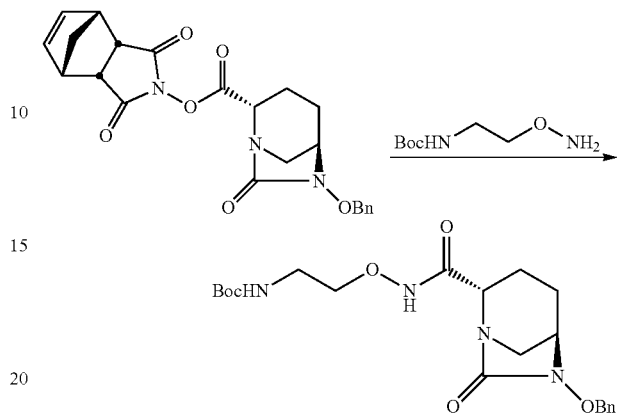

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Reference Example 4, 49.7 g, 113.6 mmol) was suspended in dehydrated ethyl acetate (650 mL). To the suspension were added a solution of tert-butyl 2-(aminooxy)ethylcarbamate (24.2 g) in dehydrated ethyl acetate (134 mL) and triethylamine (13.8 g) at room temperature, followed by stirring for 2.5 hours. The reaction solution was diluted with ethyl acetate (0.8 L), washed sequentially with ice-cold 0.25 M hydrochloric acid (1 L), saturated sodium bicarbonate (1 L), and water (1 L), and concentrated under reduced pressure to afford 48.08 g of the title compound (yield 98%, HPLC area ratio of 99% or more). Instrumental data were consistent with those of the compound of Reference Example 5, Step 1.

Example 1d

[Chemical Formula 64]

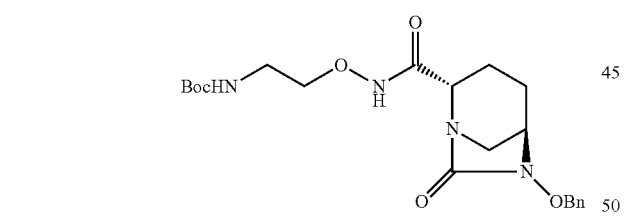

(3aR,7aS)-1,3-Dioxo-3a,4,7,7a-tetrahydro-1H-isoindol-2(3H)-yl(2S,5R)-6-(benzyloxy)-7-oxo-1,6-diazabicyclo[3.2.1]octane-2-carboxylate (Reference Example 18, 425 mg, 1 mmol) was dissolved in dehydrated chloroform (5 mL), and a solution of tert-butyl 2-(aminooxy)ethylcarbamate (211 mg) in dehydrated ethyl acetate (1.41 g) and triethylamine (121 mg) were added under ice-cooling, followed by stirring for 30 minutes. The reaction solution was diluted with ethyl acetate (75 mL), washed sequentially with 10% citric acid (35 mL), saturated sodium bicarbonate (35 mL), and saturated brine (35 mL), and dried over anhydrous magnesium sulfate, and the filtrate was concentrated under reduced pressure. The residue was subjected to silica gel column chromatography (hexane/ethyl acetate=1/2) to afford 481 mg of the title compound (quantitative). Instrumental data were consistent with those of the compound of Reference Example 5, Step 1.

Example 1e

[Chemical Formula 65]

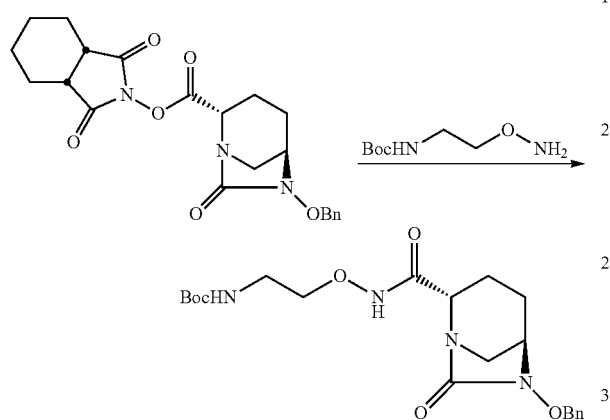

(3aR,7aS)-1,3-Dioxohexahydro-1H-isoindol-2(3H)-yl (2S,5R)-6-(benzyloxy)-7-oxo-1,6-diazabicyclo[3.2.1]octane-2-carboxylate (Reference Example 20, 427 mg, 1 mmol) was dissolved in dehydrated chloroform (5 mL), and a solution of tert-butyl 2-(aminooxy)ethylcarbamate (211 mg) in dehydrated ethyl acetate (1.41 g) and triethyl amine (121 mg) were added under ice-cooling, followed by stirring for 30 minutes. The reaction solution was diluted with ethyl acetate (75 mL), washed sequentially with 10% citric acid (35 mL), saturated sodium bicarbonate (35 mL), and saturated brine (35 mL), and dried over anhydrous magnesium sulfate, and the filtrate was concentrated under reduced pressure. The residue was subjected to silica gel column chromatography (hexane/ethyl acetate=1/2) to afford 418 mg of the title compound (yield 96%). Instrumental data were consistent with those of the compound of Reference Example 5, Step 1.

Example 2 tert-Butyl{2-[({[(2S,5R)-6-hydroxy-7-oxo-1,6-diazabicyclo[3.2.1]oct-2-yl]carbonyl}amino)oxy]ethyl}carbamate (V-1)

[Chemical Formula 66]

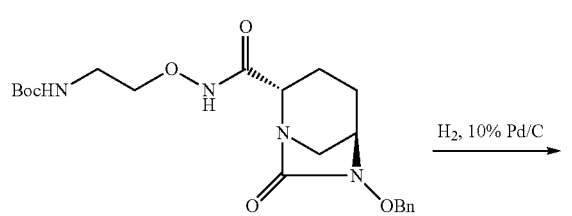

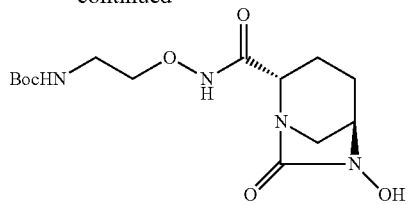

To a solution of tert-Butyl{2-[({[(2S,5R)-6-benzyloxy-7-oxo-1,6-diazabicyclo[3.2.1]oct-2-yl]carbonyl}amino)oxy]ethyl}carbamate (IV-1, 5.52 kg, 12.705 mol) in methanol (85 L), was added 10% palladium carbon catalyst (50% wet, 0.55 kg), followed by stirring for 1 hour under hydrogen pressure (0.1 MPa). The catalyst was filtered, and the solid was washed with methanol (25 L). The filtrates were combined and concentrated under reduced pressure to 39 L at a liquid temperature of 10° C. or less. To the concentrate was added acetonitrile (44 L), and the mixture was substitution-concentrated to 39 L at a liquid temperature of 10° C. or less. This operation was conducted twice. The mixture was cooled to 0° C., followed by stirring overnight. The precipitated crystals were filtered, washed with acetonitrile (24 L), and dried in vacuo to afford 3.63 kg of the title compound (yield 83%). Instrumental data were consistent with those of the compound of Reference Example 5, Step 2.

Example 3

Tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}carbamate (VI-1)

Example 3a

[Chemical Formula 67]

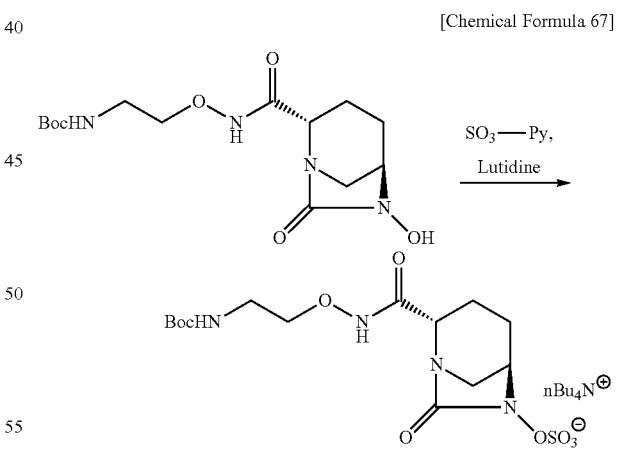

To acetonitrile (51 L) were sequentially added water (51 mL), tert-butyl{2-[({[(2S,5R)-6-hydroxy-7-oxo-1,6-diazabicyclo[3.2.1]oct-2-yl]carbonyl}amino)oxy]ethyl}carbamate (V-1, 3.53 kg, 10.251 mol), sulfur trioxide-pyridine complex (3.95 kg), and 2,6-lutidine (2.21 kg), followed by stirring at 35 to 45° C. overnight. The mixture was filtered to remove insolubles, and the solid was washed with acetonitrile (11 L). The filtrates were combined and concentrated to 17 L. The concentrate was cooled to 10° C. or less, and the layers were separated with 9% sodium dihydrogenphosphate (60 L) and ethyl acetate (113 L). The organic layer was again extracted with 9% sodium dihydrogenphosphate (11 L). To the resulting aqueous layer were added ethyl acetate (113 L), an aqueous solution of 30% tetrabutylammonium hydrogensulfate (12.87 kg), and 37% sodium dihydrogenphosphate (56.5 kg), followed by stirring for 15 minutes. The organic layer was separated, washed with 20% sodium dihydrogenphosphate (60 L), dried over anhydrous magnesium sulfate (2.5 kg), filtered, and then concentrated under reduced pressure. The crystals of the title compound were precipitated in the concentrated solutions, and were dissolved in ethyl acetate, and the total liquid volume was adjusted to 20 L to afford 32.55 kg of a solution of the title compound in ethyl acetate (net 6.25 kg, yield 92%). The solution was subjected to the next step without further purification.

Example 3b

One-Pot synthesis from tert-butyl{2-[({[(2S,5R)-6-benzyloxy-7-oxo-1,6-diazabicyclo[3.2.1]oct-2-yl]carbonyl}amino)oxy]ethyl}carbamate (IV-1)

[Chemical Formula 68]

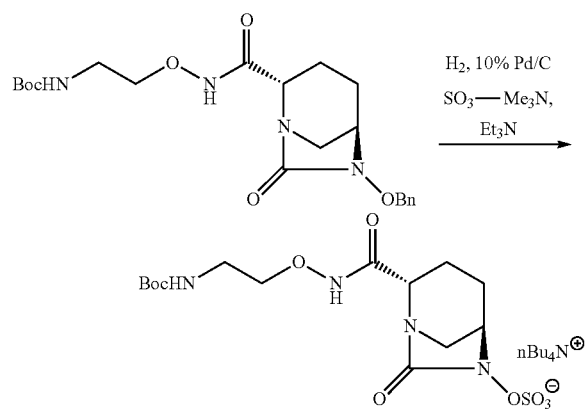

To a solution of tert-butyl{2-[({[(2S,5R)-6-benzyloxy-7-oxo-1,6-diazabicyclo[3.2.1]oct-2-yl]carbonyl}amino)oxy]ethyl}carbamate (IV-1, 515 mg, 1.16 mmol) in isopropanol (7 mL) were added water (5 mL), sulfur trioxide-trimethylamine complex (196 mg), triethylamine (0.0407 mL), and 10% palladium carbon catalyst (53.3% wet, 95.0 mg) under hydrogen atmosphere, followed by stirring at room temperature for 2 hours. A 10% palladium carbon catalyst (53.3% wet, 63.5 mg) was further added, and the mixture was stirred at room temperature for 3 hours under hydrogen atmosphere and then substituted with argon gas, followed by stirring at room temperature for 1 hour. The catalyst in the reaction solution was filtered through a Celite pad and washed with isopropanol/water (1/1, 40 mL), and then was filtered through MF (Millipore) and washed with isopropanol/water (1/1, 15 mL). The isopropanol was then distilled off under reduced pressure. To the resulting aqueous solution were added sodium dihydrogenphosphate (5.29 g), ethyl acetate (20 mL), and tetrabutylammonium hydrogensulfate (476 mg), followed by stirring at room temperature for 10 minutes. The mixture was then extracted twice with ethyl acetate. The organic layer was dried over sodium sulfate, filtered, and concentrated to afford 702 mg of the title compound (yield 91%).

Example 3c

Sequential synthesis from tert-butyl{2-[({[(2S,5R)-6-benzyloxy-7-oxo-1,6-diazabicyclo[3.2.1]oct-2-yl]carbonyl}amino)oxy]ethyl}carbamate (IV-1)

[Chemical Formula 69]

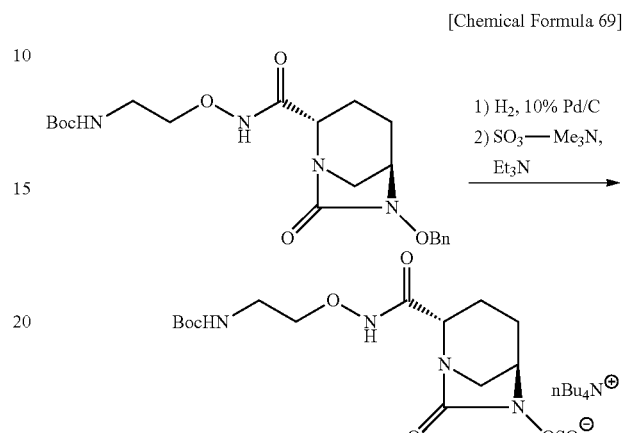

To a solution of tert-butyl{2-[({[(2S,5R)-6-benzyloxy-7-oxo-1,6-diazabicyclo[3.2.1]oct-2-yl]carbonyl}amino)oxy]ethyl}carbamate (IV-1, 5.0 g, 11.51 mmol) in isopropanol (80 mL) was added 10% palladium carbon catalyst (50% wet, 0.5 g), followed by stirring for 2 hours under hydrogen atmosphere. The catalyst in the reaction solution was filtered through a Celite pad, and the solid was washed with isopropanol (15 mL). The filtrates were then combined, and to this were added water (47.5 mL), sulfur trioxide-trimethylamine complex (1.8 g), and triethylamine (0.237 g), followed by stirring at 25 to 30° C. for 24 hours. The mixture was concentrated to 47 mL under reduced pressure. To this were added sodium dihydrogenphosphate (11.87 g), ethyl acetate (200 mL), and tetrabutylammonium hydrogensulfate (4.688 g), followed by stirring for 10 minutes. The organic layer was separated, and the aqueous layer was further extracted with ethyl acetate (2×100 mL). The combined organic phases were dried over magnesium sulfate and filtered. The organic solvent of the filtrate was concentrated under reduced pressure to afford a solution of the title compound in ethyl acetate (net 6.522 g, yield 85%)

Example 4

(2S,5R)—N-(2-Aminoethoxy)-7-oxo-6-(sulfooxy)-1,6-diazabicyclo[3.2.1]octane-2-carboxamide (VII-1-CR)

[Chemical Formula 70]

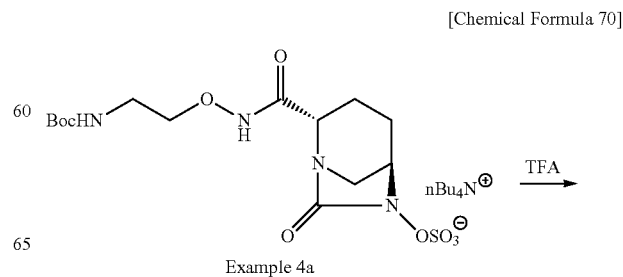

Example 4a

-continued

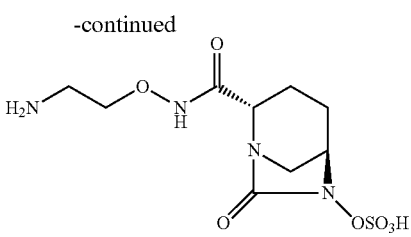

A solution of tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}carbamate (VI-1, 788 g, net 467.1 g, 0.701 mol) in dichloromethane (934 mL) was cooled to −20° C. under nitrogen stream, trifluoroacetic acid (934 mL) was added dropwise over 15 minutes, and the temperature was elevated to 0° C., followed by stirring for 1 hour. The reaction solution was cooled to −20° C., and to this was added dropwise diisopropyl ether (4.17 L), and the temperature of the mixture was elevated to −6° C., and the mixture was stirred for 1 hour. The precipitates were filtered and washed with diisopropyl ether (2×1 L), and the wet solid was dried in vacuo to afford 342.08 g of the title compound (net 222.35 g, yield 98%, HPLC area ratio of 96.1%, CE/TFA 27 mol %).

Example 4b

Tetrabutylammonium tert-butyl{2-[({[(2S,5R)-7-oxo-6-(sulfooxy)-1,6-diazabicyclo[3.2.1]oct-2-yl]carbonyl}amino)oxy]ethyl}carbamate (VI-1, ethyl acetate solution of 15.60 kg, net 2.98 kg) was cooled to a liquid temperature of 0° C. or less and concentrated to 9 L. To the concentrate was added dichloromethane (9 L), and the mixture was cooled to −20° C. under a nitrogen stream. To the mixture was added dropwise trifluoroacetic acid (16.5 L) at −5° C. or less over about 1 hour, followed by stirring at −5 to 0° C. for 1 hour. To the reaction solution was added ethyl acetate cooled to 0° C. in portions at 7° C. or less (4×8.3 L, 24.6 L, 57.8 L in total), followed by stirring at 0° C. overnight. The precipitates were filtered, washed with ethyl acetate (13.5 L, 9 L) and dried in vacuo to afford 1.74 kg of the title compound (net 1.43 kg, yield 99%, HPLC area ratio of 99.1%, CE/TFA 10 mol %, GC/EtOAc 14%).

Example 5

Crystalline form I of (2S,5R)—N-(2-aminoethoxy)-7-oxo-6-(sulfooxy)-1,6-diazabicyclo[3.2.1]octane-2-carboxamide (VII-1)

Example 5a

A 0.5 M acetic acid buffer (pH 5.5, 35 mL) was ice-cooled, and to this were added (2S,5R)—N-(2-aminoethoxy)-7-oxo-6-(sulfooxy)-1,6-diazabicyclo[3.2.1]octane-2-carboxamide (VII-1-CR, 36 g) and cooled 5M sodium hydroxide alternately to adjust the pH to 5.5. The mixture was subjected to octadecylsilica gel column chromatography (3.6 L) and eluted with water. Active fractions were collected and concentrated under reduced pressure with an water bath of 35° C. The precipitated crystals were dried in vacuo overnight. 2.10 g of the resulting crystals was pulverized, and then isopropanol/water (19/1, 13 mL) was added under ice-cooling, followed by triturating at 0° C. for 1 hour. The suspension was filtered, followed by washing with cooled isopropanol/water (19/1, 80 mL). The resulting crystals were dried in vacuo to afford 1.68 g of the title compound (yield 80%). DSC endothermic peak: 111° C. Solubility in an aqueous 60% isopropanol solution: 0.44% (10° C.), 0.48% (20° C.). The title compound showed a characteristic peak pattern in powder X-ray diffraction pattern as shown in Table 4 and FIG. 1 below. Instrument and assay parameters were as follows: the powder X-ray diffractometer: RINT2100 from Rigaku Corporation; X-ray source: CuKα1, tube voltage: 40 kV, tube current: 40 mA, scanning speed 4°/min, scanning range: 2θ=3 to 40°.

TABLE 4

Powder X-ray data
Powder X-ray diffraction of Crystalline form I

| 2θ (Cuka) | Latticer spacing (d) Å | Relative intensity I/IO |
|---|---|---|
| 12.04 | 7.34 | 13 |
| 15.64 | 5.66 | 53 |
| 16.02 | 5.53 | 26 |
| 16.70 | 5.30 | 58 |
| 17.66 | 5.02 | 49 |
| 19.02 | 4.66 | 100 |
| 20.30 | 4.37 | 46 |
| 20.74 | 4.28 | 11 |
| 21.88 | 4.06 | 10 |
| 24.16 | 3.68 | 11 |
| 24.56 | 3.62 | 15 |
| 25.66 | 3.47 | 18 |
| 26.54 | 3.36 | 17 |
| 26.96 | 3.30 | 13 |
| 28.18 | 3.16 | 12 |
| 28.72 | 3.11 | 14 |
| 29.44 | 3.03 | 16 |
| 29.86 | 2.99 | 13 |
| 35.90 | 2.50 | 10 |

Example 5b (2S,5R)—N-(2-Aminoethoxy)-7-oxo-6-(sulfooxy)-1,6-diazabicyclo[3.2.1]octane-2-carboxamide (VII-1-CR, net 4.253 g) was dissolved in a 0.2 M phosphate buffer (pH 6.5, 73 mL) and the pH was adjusted to 5.5, followed by dilution with water (20 mL). The mixture was concentrated to 130 mL, subjected to resin purification (SP207, 260 mL), and eluted with water (238 mL) and an aqueous 10% isopropanol solution (780 mL). Active fractions were collected and concentrated to 30 mL under reduced pressure. To this was introduced activated carbon (Seisei Shirasagi, 87 mg), followed by stirring at room temperature for 30 minutes. The activated carbon was filtered off with a membrane filter, and the filtrate was subjected to lyophilisation to afford 4.07 g of (2S,5R)—N-(2-aminoethoxy)-7-oxo-6-(sulfooxy)-1,6-diazabicyclo[3.2.1]octane-2-carboxamide (VII-1) in an amorphous form (yield 95.7%). This amorphous compound (0.2 g) was dissolved in water (0.8 mL), and the solution was added isopropanol (1.2 mL) and seeded with crystalline form I (Example 5a, 1 mg) at room temperature, followed by stirring with a stirring bar for 3 hours. The precipitated crystals were filtered and dried to afford 0.1 g of the title compound (yield 50%). The crystals showed the same peak pattern as the crystals of Example 5a in powder X-ray diffraction pattern.

Example 5c (2S,5R)—N-(2-Aminoethoxy)-7-oxo-6-(sulfooxy)-1,6-diazabicyclo[3.2.1]octane-2-carboxamide (VII-1-CR, net 2.113 g) and a 0.2 M phosphate buffer (pH 6.5, 73 mL) were added alternately, and the pH was adjusted to 4.6, followed by dilution with water (27 mL). The mixture was concentrated to 80 mL under reduced pressure, and then the pH was adjusted to 5.4 with a 0.2 M phosphate buffer (pH 6.5, 16 mL), followed by dilution with water (48 mL). The mixture was subjected to resin purification (SP207, 240 mL), and eluted with water (276 mL) and an aqueous 10% isopropanol solution (720 mL). Active fractions were collected and concentrated under reduced pressure to 12 mL. To this was added activated carbon (Seisei Shirasagi, 40 mg), followed by stirring at room temperature for 30 minutes. The activated carbon was filtered off through a membrane filter, followed by dilution with water to 14 mL. The aqueous solution was seeded with crystalline form I (Example 5b, 6 mg), stirred with a stirring bar at room temperature. To the resulting suspension was added dropwise isopropanol (84 mL) over 1 hour. After completion of dropwise addition, the mixture was stirred for 3 hours. The precipitated crystals were filtered and dried to afford 1.834 g of the title compound (yield 86.8%). Water content: 5.37%, the content of anhydrous product: 95.3%, HPLC area ratio of 99.3%. The crystals showed the same peak pattern as the crystals of Example 5a in powder X-ray diffraction pattern.

Example 6

Crystalline form II of (2S,5R)—N-(2-aminoethoxy)-7-oxo-6-(sulfooxy)-1,6-diazabicyclo[3.2.1]octane-2-carboxamide (VII-1)

Example 6a

A 0.2 M phosphate buffer (pH 6.5, 0.8 L) was cooled to 10° C. or less. To this were added while stirring (2S,5R)—N-(2-aminoethoxy)-7-oxo-6-(sulfooxy)-1,6-diazabicyclo[3.2.1]octane-2-carboxamide (VII-1-CR, net 49.96 g) and a cooled 0.2 M phosphate buffer (pH 6.5) alternately in small portions to adjust the pH between 4.2 and 5.5 and finally to pH 5.5. The mixture was diluted with water (the total amount of 1.8 L) and concentrated under reduced pressure at a liquid temperature of 18° C. or less to 1.6 L. The concentrate was diluted with water to 1.8 L (HPLC area ratio of 96.7%), subjected to resin purification (Sepabeads SP207, 3 L), and eluted with water (0.83 L) and an aqueous 10% isopropanol solution to collect active fractions. The active fractions were combined (1.5 L) and concentrated under reduced pressure at a liquid temperature of 15° C. or less to 0.5 L. To this was added activated carbon (0.88 g), followed by stirring for 30 minutes. The activated carbon was filtered off through a membrane filter and washed with water (0.05 L×2). The filtrates were combined and concentrated under reduced pressure at a liquid temperature of 15° C. or less to 0.2 L, and the liquid temperature was adjusted to 10 to 15° C. To the mixture was added dropwise isopropanol (0.25 L) over 10 minutes. After stirring for 1 hour, isopropanol (0.6 L) was further added dropwise over 15 minutes. The mixture was stirred for 1 hour, and the precipitated crystals were filtered, washed with isopropanol (0.2 L), and dried in vacuo until the material-temperature became 20° C. to afford 44.69 g of the title compound (yield 85%, water content 5.9%, HPLC area ratio of 100%). DSC endothemilc peak: 92° C. Solubility in an aqueous 60% isopropanol solution: 0.67% (10° C.), 0.74% (20° C.).

Figure 2:
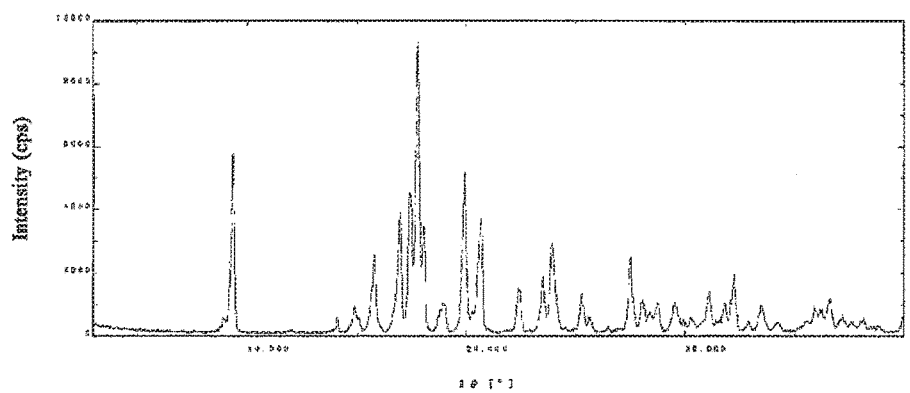
FIG. 2 shows a powder X-ray diffraction pattern of crystalline form II.

The title compound also showed a characteristic peak pattern in powder X-ray diffraction pattern as shown in Table 5 and FIG. 2 below. Instrument and assay parameters were as follows: powder X-ray diffractometer: RINT2100 from Rigaku Corporation; X-ray source: CuKα1, tube voltage: 40 kV, tube current: 40 mA, scanning speed 4°/min, scanning range: 2θ=3 to 40°.

TABLE 5

Powder X-ray data
Powder X-ray diffraction of Crystalline form II

| Peak position | | |
|---|---|---|
| 2θ (CuKα) | Lattice spacing (d) Å | Relative intensity I/I0 |
| 9.34 | 9.46 | 62 |
| 15.76 | 5.62 | 28 |
| 16.94 | 5.23 | 42 |
| 17.38 | 5.10 | 49 |
| 17.74 | 5.00 | 100 |
| 18.04 | 4.91 | 37 |
| 18.98 | 4.67 | 11 |
| 19.92 | 4.45 | 56 |
| 20.68 | 4.29 | 40 |
| 22.42 | 3.96 | 16 |
| 23.52 | 3.78 | 19 |
| 23.94 | 3.71 | 31 |
| 25.30 | 3.52 | 14 |
| 27.50 | 3.24 | 26 |
| 28.06 | 3.18 | 12 |
| 28.74 | 3.10 | 12 |
| 29.54 | 3.02 | 12 |
| 31.08 | 2.88 | 14 |
| 31.82 | 2.81 | 11 |
| 32.24 | 2.77 | 19 |
| 33.50 | 2.67 | 11 |
| 35.92 | 2.50 | 10 |
| 36.62 | 2.45 | 13 |

Example 6b

Experiment on Crystal Transformation of Crystalline Form II of (2S,5R)—N-(2-aminoethoxy)-7-oxo-6-(sulfooxy)-1,6-diazabicyclo[3.2.1]octane-2-carboxamide (VII-1)

A small amount of a suspension of the crystals of Example 6a was taken and stirred at room temperature for one day. The precipitated crystals were collected and subjected to powder X-ray crystal diffraction. No crystal transformation to a different crystal form was observed.

Example 7

Crystalline Form III of (2S,5R)—N-(2-aminoethoxy)-7-oxo-6-(sulfooxy)-1,6-diazabicyclo[3.2.1]octane-2-carboxamide (VII-1)

Example 7a

A 0.2 M phosphate buffer (pH 6.5, 3.0 L) was cooled to 10° C. or less, and to this were added while stirring (2S,5R)—N-(2-aminoethoxy)-7-oxo-6-(sulfooxy)-1,6-diazabicyclo[3.2.1]octane-2-carboxamide (VII-1-CR, net 133.334 g) and a cooled 0.2 M phosphate buffer (pH 6.5, 1.8 L) alternately in small portions to adjust the pH between 5.1 and 5.5, and finally to pH 5.3. The mixture was concentrated under reduced pressure at a liquid temperature of 18° C. or less to 3.6 L. The pH of the concentrate was adjusted to pH 5.5 with a 0.2 M phosphate buffer (pH 6.5). The concentrate was diluted with water to 4.8 L, subjected to resin purification (Sepabeads SP207, 7 L), and eluted with water (7.2

Figure 3:
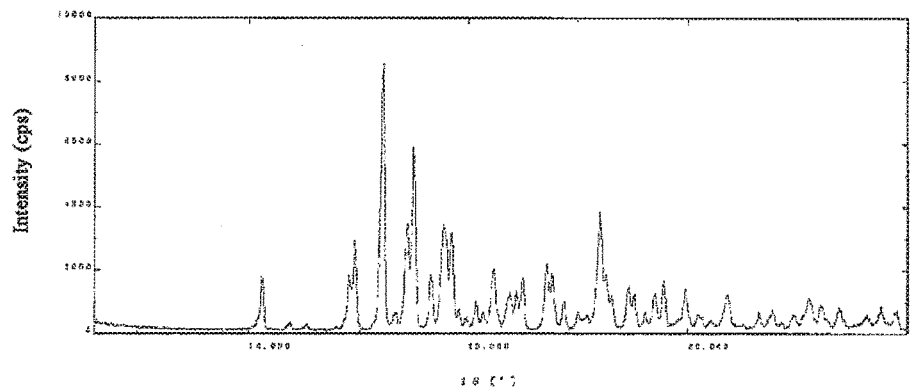
FIG. 3 shows a powder X-ray diffraction pattern of crystalline form III.

L) and an aqueous 10% isopropanol solution to collect active fractions. The active fractions were combined (3.1 L) and concentrated under reduced pressure at a liquid temperature of 15° C. or less to 1.8 L. To this was added activated carbon (2.66 g), followed by stirring for 30 minutes. The activated carbon was filtered off through a membrane filter and washed with water (0.39 L). The filtrates were combined and concentrated under reduced pressure at a liquid temperature of 18° C. or less to 0.6 L. The liquid temperature of the concentrate was adjusted to 20 to 25° C., and to this was added dropwise isopropanol (0.77 L). Crystalline form II (Example 6a, 0.63 g) were then seeded, followed by stirring for 1 hour. To the mixture was further added dropwise isopropanol (1.93 L) over 1.5 hours, followed by stirring for 30 minutes. The precipitated crystals were filtered, washed with isopropanol (1 L), and dried in vacuo until the material temperature became 20° C. 127.3 g of the title compound containing a small amount of crystalline form II was obtained (yield 90%, water content 5.3%, HPLC area ratio of 99.9%). The crystals obtained in this step were used as seed crystals, and a similar step was repeated. The resulting crystals were further used as seed crystals in the next step to afford the title compound as crystalline form III alone in powder X-ray crystal diffraction. DSC endothermic peak: 102° C. Solubility in an aqueous 60% isopropanol solution: 0.76% (10° C.), 0.80% (20° C.). The title compound showed a characteristic peak pattern in powder X-ray diffraction pattern as shown in Table 6 and FIG. 3 below. Instrument and assay parameters were as follows: powder X-ray diffractometer: RINT2100 from Rigaku Corporation; X-ray source: CuKα1, tube voltage: 40 kV, tube current: 40 mA, scanning speed 4°/min, scanning range: 2θ=3 to 40°.

TABLE 6

Powder X-ray data
Powder X-ray diffraction of Crystalline form III

Peak position

| 2θ (Cuka) | Lattice spacing (d) Å | Relative intensity I/IO |
|---|---|---|
| 10.62 | 8.32 | 20 |
| 14.52 | 6.10 | 20 |
| 14.80 | 5.98 | 33 |
| 16.08 | 5.51 | 100 |
| 17.18 | 5.16 | 39 |
| 17.48 | 5.07 | 68 |
| 18.28 | 4.85 | 20 |
| 18.86 | 4.70 | 39 |
| 19.24 | 4.61 | 37 |
| 20.38 | 4.35 | 10 |
| 21.16 | 4.20 | 23 |
| 21.90 | 4.06 | 13 |
| 22.22 | 4.00 | 13 |
| 21.50 | 3.95 | 20 |
| 23.60 | 3.77 | 24 |
| 23.84 | 3.73 | 20 |
| 24.38 | 3.65 | 10 |
| 26.00 | 3.42 | 44 |
| 26.28 | 3.39 | 21 |
| 26.54 | 3.36 | 12 |
| 27.30 | 3.26 | 16 |
| 27.58 | 3.23 | 13 |
| 28.50 | 3.13 | 13 |
| 28.90 | 3.09 | 18 |
| 29.88 | 2.99 | 15 |
| 31.84 | 2.81 | 12 |
| 35.54 | 2.52 | 11 |

Example 7b

A 0.2 M phosphate buffer (pH 6.5, 7.2 L) was cooled to 10° C. or less, and to this were added while stirring (2S,5R)—N-(2-aminoethoxy)-7-oxo-6-(sulfooxy)-1,6-diazabicyclo[3.2.1]octane-2-carboxamide (VII-1-CR, net 1.2 kg) and an ice-cooled 0.2 M phosphate buffer (pH 6.5, 3.5 L) alternately in small portions to adjust the pH between 4.2 and 4.8, and finally to 4.6. The mixture was diluted with water (19.3 L) (the total amount of 30 L) and concentrated under reduced pressure at a liquid temperature of 18° C. or less to 24 L. The pH of the concentrate was adjusted to pH 5.4 with 0.2 M phosphate buffer (pH 6.5, 2.4 L) (HPLC area ratio of 98.5%). The concentrate was diluted with water to 43.2 L, subjected to resin purification (Sepabeads SP207, 75 L) and eluted with water (83 L) and an aqueous 10% isopropanol solution to collect active fractions. The active fractions were combined (33 L) and concentrated at a liquid temperature of 15° C. or less to 7.2 L. To this was added activated carbon (24 g), followed by stirring for 30 minutes. The activated carbon was filtered off through a membrane filter and washed with water (0.4 L×2). The filtrates were combined, and the temperature of the liquid was adjusted to 20 to 25° C. This was seeded with crystalline form III (Example 7a, 3.6 g). To the mixture was added dropwise isopropanol (50.4 L) over 1 hour, followed by stirring overnight. The precipitated crystals were filtered, washed with isopropanol (4.8 L), and dried in vacuo until the material temperature became 20° C. to afford 1.17 kg of the title compound (yield 90%, water content 5.3%, HPLC area ratio of 100%). The crystals showed the same peak pattern as the crystals of Example 7a in powder X-ray diffraction pattern.

Example 7c

Experiment on Crystal Transformation of Crystalline form III of (2S,5R)—N-(2-aminoethoxy)-7-oxo-6-(sulfooxy)-1,6-diazabicyclo[3.2.1]octane-2-carboxamide (VII-1)

In the step of Example 7a, a small amount was taken out of the suspension immediately after the seeding and of the suspension after the dropwise addition of isopropanol, and each of the taken-out portions was stirred with a stirring bar at room temperature for one day and four days. The precipitated crystals were collected and subjected to powder X-ray crystals diffraction. No crystal transformation to a different crystal form was observed.

Example 7d

X-Ray Diffraction-Differential Scanning Calorimetry (XRD-DSC) Experiment on Crystalline Form of (2S,5R)—N-(2-aminoethoxy)-7-oxo-6-(sulfooxy)-1,6-diazabicyclo[3.2.1]octane-2-carboxamide (VII-1)

Crystal transformation by heating in polymorphism of crystalline form III of Example 7a was examined using XRD-DSC. Heating and cooling conditions were as follows: the temperature was elevated at a rate of 2° C./min from room temperature to 160° C. and then cooled to 63° C. under a constant relative humidity (RH) of 60%. DSC and XRD of the samples were successively measured. Instrument and assay parameters were as follows: powder X-ray diffractometer: SmartLab and XRD-DSC from Rigaku Corporation; X-ray source: CuKα1, tube voltage: 45 kV, tube current: 200 mA, scanning speed 80°/min, scanning range: 2θ=5 to 35°.

Example 8

Crystalline Form IV of (2S,5R)—N-(2-aminoethoxy)-7-oxo-6-(sulfooxy)-1,6-diazabicyclo[3.2.1]octane-2-carboxamide (VII-1)

Example 8a 0.20 g of crystalline form III of Example 7a was dissolved in 2 mL of water. To this was added dropwise while stirring methanol (30 mL), followed by standing at 20-25° C. overnight. The mixture is filtered, washed with methanol (2×2 mL), and dried in vacuo at room temperature overnight to afford 0.13 g of the title compound (yield 68%).

Figure 4:
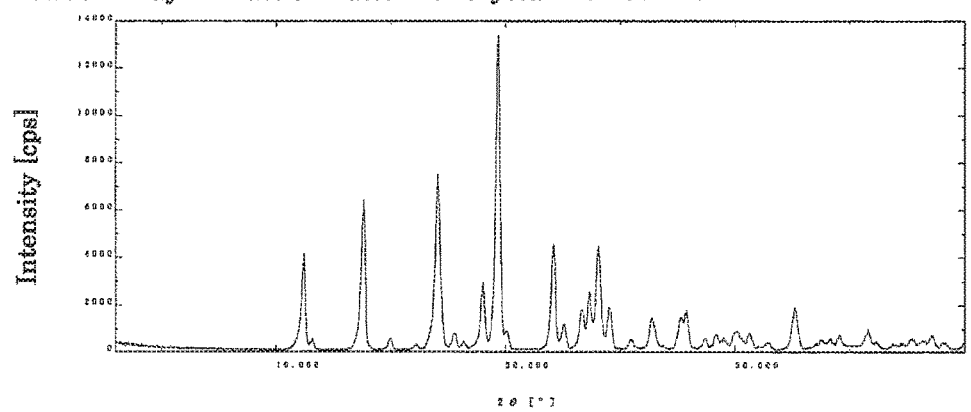
FIG. 4 shows a powder X-ray diffraction pattern of crystalline form IV.

The title compound showed a characteristic peak pattern in powder X-ray diffraction pattern as shown in Table 7 and FIG. 4 below. Instrument and assay parameters were as follows: powder X-ray diffractometer: RINT2100 from Rigaku Corporation; X-ray source: CuKα1, tube voltage: 40 kV, tube current: 40 mA, scanning speed 4°/min, scanning range: 2θ=3 to 40°.

TABLE 7

Powder X-ray data
Powder X-ray diffraction of Crystalline form IV

| 2θ (Cukα) | Peak position Lattice spacing (d) Å | Relative intensity I/I0 |
|---|---|---|
| 11.22 | 7.88 | 31 |
| 13.80 | 6.41 | 46 |
| 17.04 | 5.20 | 56 |
| 19.00 | 4.67 | 21 |
| 19.70 | 4.50 | 100 |
| 22.10 | 4.02 | 34 |
| 23.34 | 3.81 | 13 |
| 23.68 | 3.75 | 19 |
| 24.06 | 3.70 | 34 |
| 24.56 | 3.62 | 14 |
| 26.36 | 3.38 | 11 |
| 27.62 | 3.23 | 10 |
| 27.88 | 3.20 | 13 |
| 32.64 | 2.74 | 14 |

Example 8b

To 25 g of crystalline form III of Example 7a was added methanol (200 mL), followed by stirring at 20-25° C. for 3.5 hours. The mixture was filtered, washed with methanol (2×20 mL), and dried in vacuo at room temperature overnight to afford 23 g of the title compound (yield 99%). The crystals showed the same peak pattern as the crystals of Example 8a in powder X-ray diffraction pattern.

Example 8c

To 25 g of crystalline form III of Example 7a was added ethanol (200 mL), followed by stirring at 20-25° C. for 3.5 hours. The mixture was filtered, washed with ethanol (2×20 mL), and dried in vacuo at room temperature overnight to afford 23 g of the title compound (yield 99%). The crystals showed the same peak pattern as the crystals of Example 8a in powder X-ray diffraction pattern.

Example 8d

Experiment on Crystal Transformation of Crystalline Form IV of (2S,5R)—N-(2-aminoethoxy)-7-oxo-6-(sulfooxy)-1,6-diazabicyclo[3.2.1]octane-2-carboxamide (VII-1)

Crystalline form IV of Examples 8a-c was taken and isopropanol/water (6/1) was added thereto and suspended and stirred at 25° C. or 40° C. for one week. Samples were taken after 12 hours, 24 hours (one day), 48 hours (two days), 72 hours (three days), 96 hours (four days) and 168 hours (one week), and subjected to powder X-ray crystal diffraction after through-flow drying. No crystal transformation to a different crystal form was observed at all stirring times.

Example 9a

Evaluation of the Stability of Crystalline Forms I-IV of (2S,5R)—N-(2-aminoethoxy)-7-oxo-6-(sulfooxy)-1,6-diazabicyclo[3.2.1]octane-2-carboxamide (VII-1)

Crystalline form III of Example 7a were dissolved in water and subjected to lyophilisation to afford (2S,5R)—N-(2-aminoethoxy)-7-oxo-6-(sulfooxy)-1,6-diazabicyclo [3.2.1]octane-2-carboxamide (VII-1) in an amorphous form. The compounds in an amorphous form and crystalline forms I-IV of Examples 5-8 were each weighed in a screw bottle, and stability tests were conducted at each of the temperatures and humidity conditions. The methods of measurement of related substances, content measurement, and water content measurement were as follows. The results are shown in Table 9.

Measurement of Related Substances and Content

Samples were dissolved in water, and these solutions were used as sample solutions. The sample solutions each in the amount of 5 μL were tested under the following conditions by JP16, Liquid Chromatography <2.01> to obtain the amount of each related substance (%) and the total amount of related substances (%), and the content.

Test Conditions:
Column: Waters Atlantis dc18, 5 μm, 4.6×250 mm
Column temperature: a constant temperature of about 35° C.
Injected amount: 5 μL
Detector: an ultraviolet absorption photometer (wavelength: 210 nm)
Mobile phase A: 1.32 g of diammonium hydrogenphosphate was dissolved in 900 mL of water, and phosphoric acid was added to adjust the pH to 3.0. To this was then added water to make 1000 mL.
Mobile phase B: Acetonitrile for liquid chromatography
Gradient program: The mixing ratio of mobile phase A to mobile phase B was controlled as the following time program.

TABLE 8

| Time after injection (min) | Mobile phase A (vol %) | Mobile phase B (vol %) |
|---|---|---|
| 0-5 | 100 | 0 |
| 5-20 | 100 → 90 | 0 → 10 |
| 20-30 | 90 | 10 |

Flow rate: 1.0 mL/min
Retention time: about 6.5 minutes
Measurement time: 30 minutes
Water Content Measurement
About 20 mg of the product was precisely measured and tested by JP16, Water Determination <2.48> Coulometric titration.

TABLE 9

Storage conditions: 40° C./75% RH, airtight container

| Crystalline form | At start | | | 1 month | | | 3 months | | |
|---|---|---|---|---|---|---|---|---|---|
| | Water content (%) | Total amount of related substances (%) | Content (%) | Water content (%) | Total amount of related substances (%) | Content (%) | Water content (%) | Total amount of related substances (%) | Content (%) |
| Amorphous form | 1.3 | 0.5 | 99.4 | 3.3 | 6.6 | 93.3 | 3.8 | 12.3 | 87.5 |
| Form I | 5.4 | 0.1 | 99.9 | 5.4 | 0.0 | 99.9 | 5.6 | 0.1 | 99.8 |
| Form II | 5.7 | 0.1 | 99.8 | 5.6 | 0.0 | 99.8 | 5.9 | 0.5 | 99.3 |
| Form III | 5.3 | 0.0 | 99.9 | 5.3 | 0.0 | 100.0 | 5.5 | 0.0 | 99.9 |
| Form IV | 0.1 | 0.0 | 99.9 | 0.1 | 0.0 | 99.8 | NT | NT | NT |

Example 9b

Evaluation of the Stability of Crystalline Form III of (2S,5R)—N-(2-aminoethoxy)-7-oxo-6-(sulfooxy)-1,6-diazabicyclo[3.2.1]octane-2-carboxamide (VII-1) in a Packaging Container Crystalline form III was packaged under the following conditions and stability tests were conducted at each of the temperatures and humidity conditions under analysis conditions of Example 9a. The results are shown in Tables 10-12.

Packaging Container

Inner bag: a low-density polyethylene•nylon tie band
Outer bag: an aluminium laminated bag•heat sealed

TABLE 10

Stability of Crystalline form III
Inner bag: a low-density polyethylene bag • nylon tie band
Outer bag: an aluminium laminated bag • heat sealed
Storage conditions: 25° C./60% RH

| Test Parameters | At start | 3 months |
|---|---|---|
| Total amount of related substances (%) | 0.09 | 0.07 |
| Water content (%) | 5.32 | 5.23 |
| Content (%) | 99.9 | 99.9 |

TABLE 11

Stability of Crystalline form III
Inner bag: a low-density polyethylene bag • nylon tie band
Outer bag: an aluminium laminated bag • heat sealed
Storage conditions: 40° C./75% RH

| Test Parameters | At start | 1 month | 2 months | 3 months |
|---|---|---|---|---|
| Total amount of related substances (%) | 0.09 | 007 | 0.04 | 0.06 |
| Water content (%) | 5.20 | 5.51 | 5.27 | 5.29 |
| Content (%) | 99.9 | 99.9 | 99.9 | 99.9 |

TABLE 12

Stability of Crystalline form III
Inner bag: a low-density polyethylene bag • nylon tie band
Outer bag: an aluminium laminated bag • heat sealed
Storage conditions: 60° C.

| Test Parameters | At start | 2 weeks | 4 weeks |
|---|---|---|---|
| Total amount of related substances (%) | 0.09 | 0.02 | 0.04 |
| Water content (%) | 5.20 | 5.10 | 5.08 |
| Content (%) | 99.9 | 99.9 | 99.9 |

Example 10 tert-Butyl{2-[({[(2S,5R)-6-benzyloxy-7-oxo-1,6-diazabicyclo[3.2.1]oct-2-yl]carbonyl}amino)oxy]ethyl}(methyl)carbamate (IV-2)

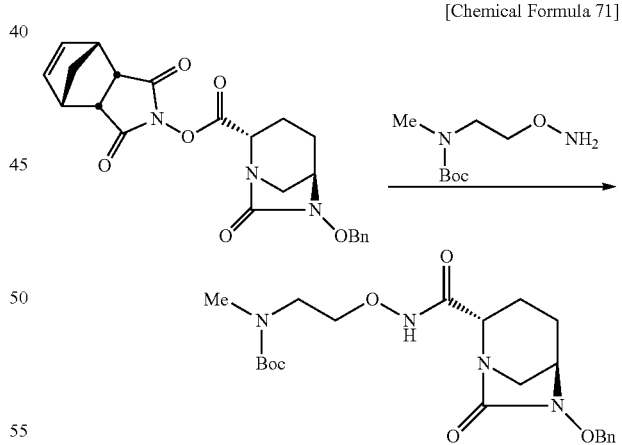

[Chemical Formula 71]

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Reference Example 4, 144 mg, 0.329 mmol) was dissolved in dehydrated dichloromethane (2.5 mL), and to this was added a solution of tert-butyl(2-(aminooxy)ethyl)(methyl)carbamate (88.8 mg) in dehydrated dichloromethane (0.5 mL), followed by stirring at room temperature for 18 hours. The reaction solution was diluted with ethyl acetate (10 mL) and washed sequentially with 0.25 M hydrochloric acid, saturated sodium bicarbonate, and saturated brine, dried over anhydrous sodium sulfate, filtered, and concentrated under reduced pressure to afford 132 mg of the title compound (yield 89%), Instrumental data were consistent with those of the compound of Reference Example 6, Step 1.

Example 11 tert-Butyl{3-[({[(2S,5R)-6-benzyloxy-7-oxo-1,6-diazabicyclo[3.2.1]oct-2-yl]carbonyl}amino)oxy]propyl}carbamate (IV-7)

[Chemical Formula 72]

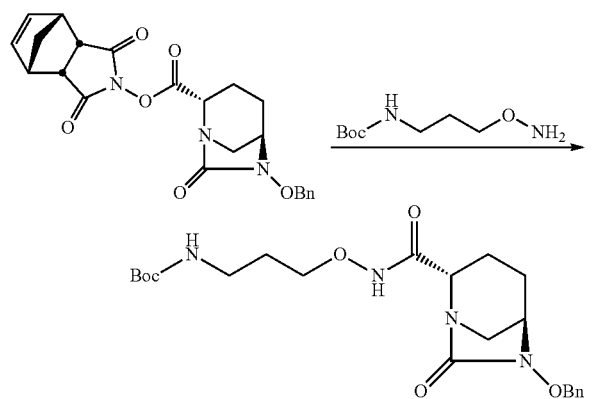

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Reference Example 4, 148 mg, 0.339 mmol) was dissolved in dehydrated dichloromethane (2.5 mL). To this was added a solution of tert-butyl 3-(aminooxy)propylcarbamate (90.9 mg) in dehydrated dichloromethane (0.5 mL), followed by stirring for 18 hours at room temperature. The reaction solution was diluted with ethyl acetate (10 mL), washed sequentially with 0.25 M hydrochloric acid, saturated sodium bicarbonate, and saturated brine, dried over anhydrous sodium sulfate, filtered, and concentrated under reduced pressure to afford 134 mg of the title compound (yield 88%). Instrumental data were consistent with those of the compound of Reference Example 11, Step 1.

Example 12 tert-Butyl(2S)-2-{[({[(2S,5R)-6-benzyloxy-7-oxo-1,6-diazabicyclo[3.2.1]oct-2-yl]carbonyl}amino)oxy]methyl}azetidine-1-carboxylate (IV-8)

[Chemical Formula 73]

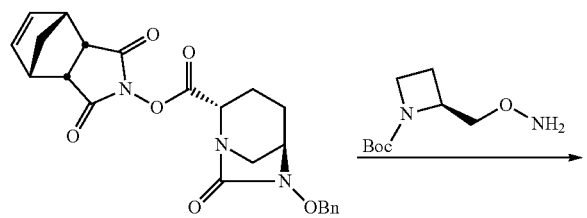

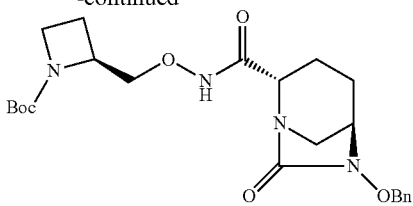

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Reference Example 4, 145 mg, 0.331 mmol) was dissolved in dehydrated dichloromethane (2.5 mL). To this was added a solution of (S)-tert-butyl 2-((aminooxy)methyl)azetidine-1-carboxylate (93.2 mg) in dehydrated dichloromethane (0.5 mL), followed by stirring at room temperature for 21 hours. The reaction solution was diluted with ethyl acetate (10 mL), washed sequentially with 0.25 M hydrochloric acid, saturated sodium bicarbonate water, and saturated brine, dried over anhydrous sodium sulfate, filtered, and concentrated under reduced pressure to afford 127 mg of the title compound (yield 83%). Instrumental data were consistent with those of the compound of Reference Example 12, Step 1.

Example 13 tert-Butyl(3S)-3-[({[(2S,5R)-6-benzyloxy-7-oxo-1,6-diazabicyclo[3.2.1]oct-2-yl]carbonyl}amino)oxy]pyrrolidine-1-carboxylate (IV-11)

[Chemical Formula 74]

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Reference Example 4, 145 mg, 0.332 mmol) was dissolved in dehydrated dichloromethane (2.5 mL). To this was added a solution of (S)-tert-butyl 3-(aminooxy)pyrrolidine-1-carboxylate (91.6 mg) in dehydrated dichloromethane (0.5 mL), followed by stirring at room temperature for 19 hours. The reaction solution was diluted with ethyl acetate (10 mL), washed sequentially with 0.25 M hydrochloric acid, saturated sodium bicarbonate, and saturated brine, dried over anhydrous sodium sulfate, filtered, and concentrated under reduced pressure to afford 145 mg of the title compound (yield 95%). Instrumental data were consistent with those of the compound of Reference Example 15, Step 1.

Example 14 tert-Butyl 3-{[({[(2S,5R)-6-benzyloxy-7-oxo-1,6-diazabicyclo[3.2.1]oct-2-yl]carbonyl}amino)oxy]methyl}azetidine-1-carboxylate (IV-12)

[Chemical Formula 75]

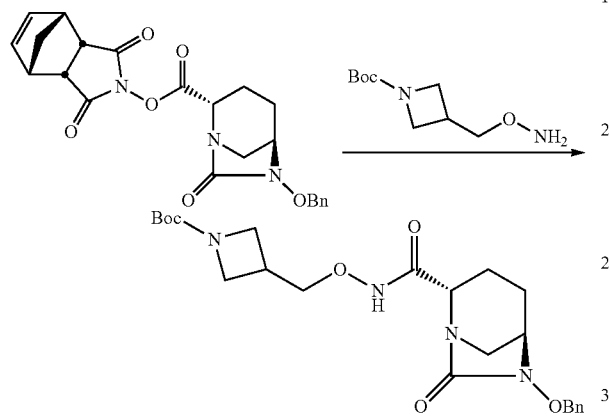

(1R,2S,6R,7S)-3,5-Dioxo-4-azatricyclo[5.2.1.0$^{2,6}$]dec-8-en-4-yl(2S,5R)-6-(benzyloxy)-7-oxo-1,6-diazabicyclo[3.2.1]octane-2-carboxylate (Example 4, 140 mg, 0.320 mmol) was dissolved in dehydrated dichloromethane (2.5 mL). To this was added a solution of tert-butyl 3-((aminooxy)methyl)azetidine-1-carboxylate (91.5 mg) in dehydrated dichloromethane (0.5 mL), followed by stirring at room temperature for 20 hours. The reaction solution was diluted with ethyl acetate (10 mL), washed sequentially with 0.25 M hydrochloric acid, saturated sodium bicarbonate, and saturated brine, dried over anhydrous sodium sulfate, filtered, and concentrated under reduced pressure to afford 132 mg of the title compound (yield 90%). Instrumental data were consistent with those of the compound of Reference Example 16, Step 1.

The invention claimed is:

1. A process for producing a compound represented by Formula (VII), the process comprising reacting a compound represented by the following Formula (III):

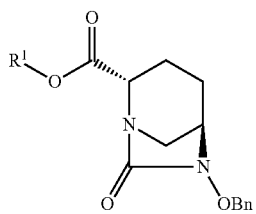

with a compound R$^3$ONH$_2$ to obtain a compound represented by the following Formula (IV):

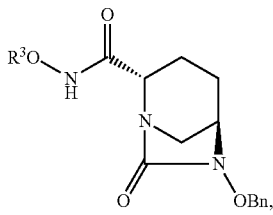

treating the compound of Formula (IV) with a palladium carbon catalyst under a hydrogen atmosphere, simultaneously or consecutively subjecting the resultant compound to a sulfation reaction with a sulfur trioxide-trimethylamine complex in the presence of a catalytic amount of base in a hydrous solvent and treating the resultant compound with tetrabutylammonium hydrogensulfate to obtain a compound represented by the following Formula (VI):

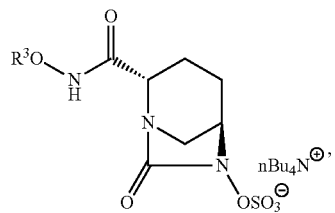

followed by, in a case where the R$^3$ONHC(=O)— side chain has a protecting group, removing the protecting group with an acid, and precipitating a crude product by adding a poor solvent to the resultant reaction solution to obtain a crude compound represented by the following Formula (VII-CR):

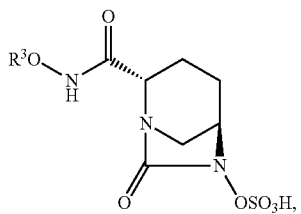

followed by alternately adding the crude compound represented by Formula (VII-CR) and an ice-cold buffer to obtain a solution having a pH of 4 to 5.5, optionally carrying out desalting with a synthetic adsorbent to produce a compound represented by the following Formula (VII):

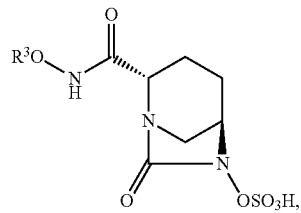

wherein in the above formulas, OBn is benzyloxy; $R^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2.6}$]dec-8-en-4-yl; and $R^3$ is a $C_{1-6}$ alkyl or a heterocyclyl, wherein $R^3$ is optionally substituted with 1 to 5 $R^4$ groups, wherein $R^4$ is selected from the group consisting of a $C_{1-6}$ alkyl, a heterocyclyl, $R^5(R^6)N$- and a protecting group, wherein $R^4$ is optionally substituted with one or more groups selected from the group consisting of a $C_{1-6}$ alkyl, a heterocyclyl, $R^5(R^6)$N- and a protecting group, wherein $R^5$ and $R^6$ each independently is hydrogen or a $C_{1-6}$ alkyl or together form a heterocyclyl, wherein $R^3$, $R^5$ and $R^6$ can together undergo ring closure.

2. A process for producing a compound represented by a Formula (IV), the process comprising reacting a compound represented by the following Formula (III):

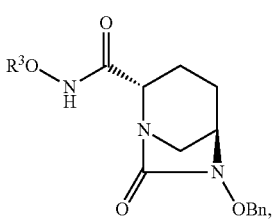

III with a compound: $R^3ONH_2$ to produce a compound represented by the following Formula (IV):

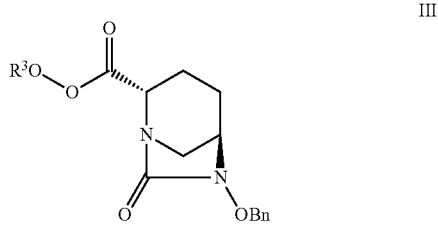

IV wherein in the above formulas, same as OBn is benzyloxy; $R^1$ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2.6}$]dec-8-en-4-yl; and $R^3$ is a $C_{1-6}$ alkyl or a heterocyclyl, wherein $R^3$ is optionally substituted with 1 to 5 $R^4$ groups, wherein $R^4$ is selected from the group consisting of a $C_{1-6}$ alkyl, a heterocyclyl, $R^5(R^6)N$- and a protecting group, wherein $R^4$ is optionally substituted with one or more groups selected from the group consisting of a $C_{1-6}$ alkyl, a heterocyclyl, $R^5(R^6)N$- and a protecting group, wherein $R^5$ and $R^6$ each independently is hydrogen or a $C_{1-6}$ alkyl or together form a heterocyclyl, wherein $R^3$, $R^5$ and $R^6$ can together undergo ring closure.

3. A process for producing a compound represented by a Formula (VI), the process comprising treating a compound represented by the following Formula (IV):

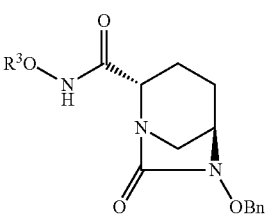

IV with a palladium carbon catalyst under a hydrogen atmosphere, simultaneously or consecutively subjecting the compound of Formula IV to a sulfation reaction with a sulfur trioxide-trimethylamine complex in the presence of a catalytic amount of base in a hydrous solvent, and treating the resultant compound with tetrabutylammonium hydrogensulfate to produce a compound represented by the following Formula (VI):

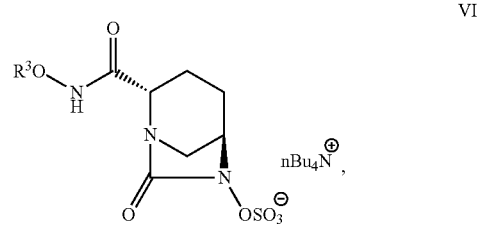

VI wherein in the above formulas, OBn is benzyloxy and $R^3$ is a $C_{1-6}$ alkyl or a heterocyclyl, wherein $R^3$ is optionally substituted with 1 to 5 $R^4$ groups, wherein $R^4$ is selected from the group consisting of a $C_{1-6}$ alkyl, a heterocyclyl, $R^5(R^6)N$- and a protecting group, wherein $R^4$ is optionally substituted with one or more groups selected from the group consisting of a $C_{1-6}$ alkyl, a heterocyclyl, $R^5(R^6)N$- and a protecting group, wherein $R^5$ and $R^6$ each independently is hydrogen or a $C_{1-6}$ alkyl or together form a heterocyclyl, wherein $R^3$, $R^5$ and $R^6$ can together undergo ring closure.

4. A process for producing a compound represented by Formula (VII), the process comprising alternately adding a crude compound represented by the following Formula (VII-CR):

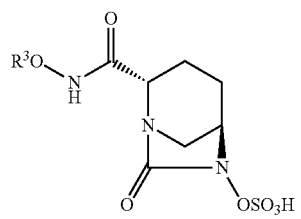

VII-CR and an ice-cold buffer to obtain a solution having a pH of 4 to 5.5, optionally carrying out desalting with a synthetic adsorbent to produce the compound represented by the following Formula (VII):

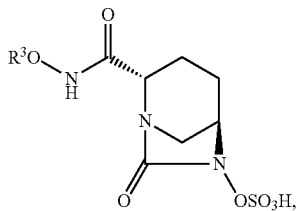

VII

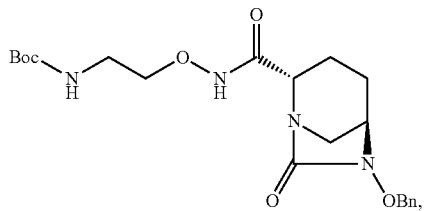

IV-1 wherein each of the Formulas VII-CR and VII, $R^3$ is is a $C_{1-6}$ alkyl or a heterocyclyl, wherein $R^3$ is optionally substituted with 1 to 5 $R^4$ groups, wherein $R^4$ is selected from the group consisting of a $C_{1-6}$ alkyl, a heterocyclyl, $R^5(R^6)N-$ and a protecting group, wherein $R^4$ is optionally substituted with one or more groups selected from the group consisting of a $C_{1-6}$ alkyl, a heterocyclyl, $R^5(R^6)N-$ and a protecting group, wherein $R^5$ and $R^6$ each independently is hydrogen or a $C_{1-6}$ alkyl or together form a heterocyclyl, wherein $R^3$, $R^5$ and $R^6$ can together undergo ring closure.

5. The process according to any of claim 1, 2, 3 or 4, wherein $R^3$ in Formulas (IV), (VI), (VII-CR) and (VII) is selected from the group consisting of:
2-(tert-butoxycarbonylamino)ethyl;
2-aminoethyl;
2-((tert-butoxycarbonyl)(methyl)amino)ethyl;
2-(methylamino)ethyl;
2-((tert-butoxycarbonyl)(isopropyl)amino)ethyl;
2-(isopropylamino)ethyl;
2-(dimethylamino)ethyl;
(2S)-2-((tert-butoxycarbonyl)amino)propyl;
(2S)-2-(amino)propyl;
(2R)-2-((tert-butoxycarbonyl)amino)propyl;
(2R)-2-(amino)propyl;
3-((tert-butoxycarbonyl)amino)propyl;
3-(amino)propyl;
(2S)-tert-butoxycarbonylazetidin-2-ylmethyl;
(2S)-azetidin-2-ylmethyl;
(2R)-tert-butoxycarbonylpyrrolidin-2-ylmethyl;
(2R)-pyrrolidin-2-ylmethyl;
(3R)-tert-butoxycarbonylpiperidin-3-ylmethyl;
(3R)-piperidin-3-ylmethyl;
(3S)-tert-butoxycarbonylpyrrolidin-3-yl;
(3S)-pyrrolidin-3-yl;
1-(tert-butoxycarbonyl)azetidin-3-yl; and
azetidin-3-yl.

6. A process for producing a compound represented by Formula (VII-1), the process comprising reacting a compound represented by the following Formula (III):

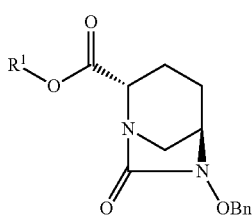

III with tert-butyl 2-(aminooxy)ethylcarbamate in the presence of a base to obtain a compound represented by the following Formula (IV-1):

followed by treating the compound of Formula IV-1 with a palladium carbon catalyst under a hydrogen atmosphere, simultaneously or consecutively subjecting the resultant compound to a sulfation reaction with a sulfur trioxide-trimethylamine complex in the presence of a catalytic amount of base in a hydrous solvent, and treating the resultant compound with tetrabutylammonium hydrogensulfate to obtain a compound represented by the following Formula (VI-1):

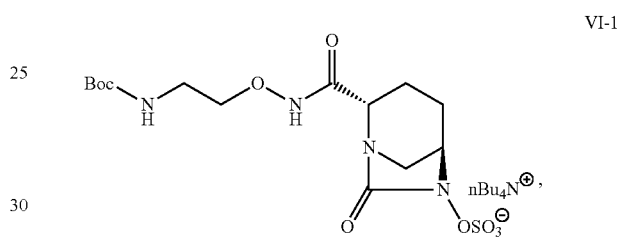

VI-1 followed by removing the tert-butoxycarbonyl group with trifluoroacetic acid and dropping ethyl acetate into the resultant reaction solution to precipitate a crude product and obtain a crude compound represented by the following Formula (VII-1-CR):

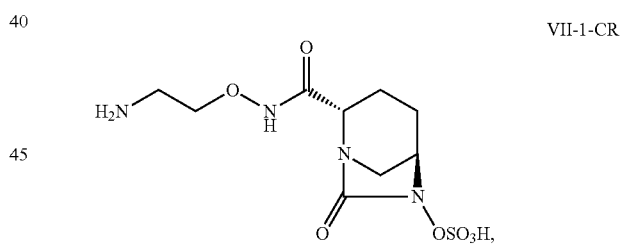

VII-1-CR followed by alternately adding the crude compound represented by Formula (VII-1-CR) and an ice-cold phosphate buffer to obtain a solution having a pH of 4 to 5.5, optionally carrying out desalting with a synthetic adsorbent to produce a compound represented by the following Formula (VII-1):

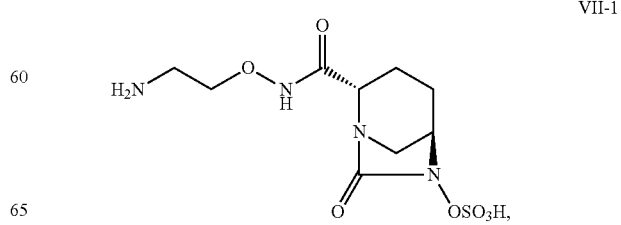

VII-1 wherein in the above formulas, OBn is benzyloxy and R¹ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2.6}$]dec-8-en-4-yl.

7. A process for producing a compound represented by Formula (IV-1), the process comprising reacting a compound represented by the following Formula (III):

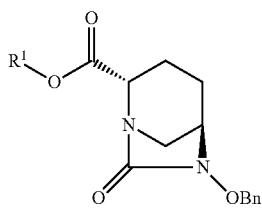

III with tert-butyl 2-(aminooxy)ethylcarbamate in the presence of a base to produce the compound represented by the following Formula (IV-1):

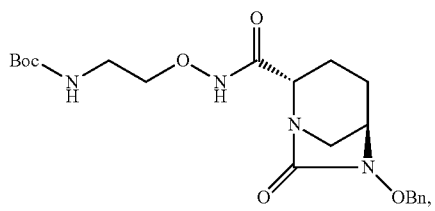

IV-1 wherein Boc is a tert-butoxycarbonyl group and in the above formulas, OBn is benzyloxy and R¹ is 2,5-dioxopyrrolidin-1-yl, 1,3-dioxo-3a,4,7,7a-tetrahydro-1H-isoindol-2(3H)-yl, 1,3-dioxohexahydro-1H-isoindol-2(3H)-yl, or 3,5-dioxo-4-azatricyclo[5.2.1.0$^{2.6}$]dec-8-en-4-yl.

8. A process for producing a compound represented by Formula (VI-1), the process comprising treating a compound represented by the following Formula (IV-1):

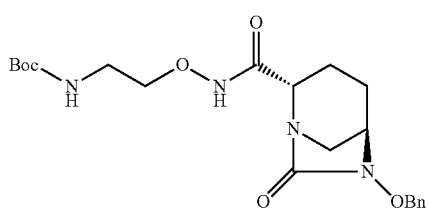

IV-1 with a palladium carbon catalyst under a hydrogen atmosphere, simultaneously or consecutively subjecting to a sulfation reaction using sulfur trioxide-trimethylamine complex in the presence of a catalytic amount of a base in a hydrous solvent, and carrying out treating with tetrabutylammonium hydrogensulfate to produce the compound represented by the following Formula (VI-1):

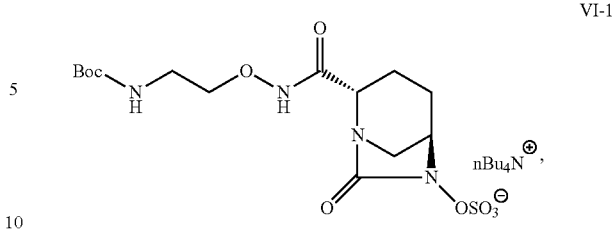

VI-1 wherein Boc is a tert-butoxycarbonyl group and in the above formulas, and OBn is benzyloxy.

9. A process for producing a compound represented by Formula (VII-1), the process comprising alternately adding a crude compound represented by the following Formula (VII-1-CR):

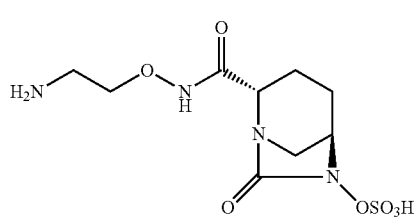

VII-1-CR and an ice-cold phosphate buffer to obtain a solution having a pH of 4 to 5.5, optionally carrying out desalting with a synthetic adsorbent to produce the compound represented by the following Formula (VII-1):

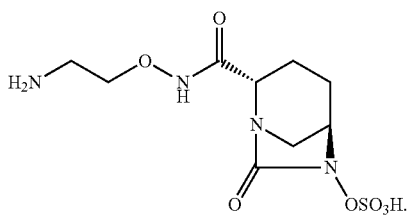

VII-1

10. The process according to claim 1, wherein in the formula (III), R¹ is selected from the group consisting of 1,3-dioxo-3a,4,7,7a-tetrahydro-1H-isoindol-2(3H)-yl, 1,3-dioxohexahydro-1H-isoindol-2 (3H)-yl and 3,5-dioxo-4-azatricyclo[5.2.1.0$^{2.6}$]dec-8-en-4-yl.

11. The process according to claim 2, wherein in the formula (III), R¹ is selected from the group consisting of 1,3-dioxo-3a,4,7,7a-tetrahydro-1H-isoindol-2(3H)-yl, 1,3-dioxohexahydro-1H-isoindol-2 (3H)-yl and 3,5-dioxo-4-azatricyclo[5.2.1.0$^{2.6}$]dec-8-en-4-yl.

12. The process according to claim 6, wherein in the formula (III), R¹ is selected from the group consisting of 1,3-dioxo-3a,4,7,7a-tetrahydro-1H-isoindol-2(3H)-yl, 1,3-dioxohexahydro-1H-isoindol-2 (3H)-yl and 3,5-dioxo-4-azatricyclo[5.2.1.0$^{2.6}$]dec-8-en-4-yl.

13. The process according to claim 7, wherein in the formula (III), R¹ is selected from the group consisting of 1,3-dioxo-3a,4,7,7a-tetrahydro-1H-isoindol-2(3H)-yl, 1,3-dioxohexahydro-1H-isoindol-2 (3H)-yl and 3,5-dioxo-4-azatricyclo[5.2.1.0$^{2.6}$]dec-8-en-4-yl.

14. The process according to claim 1, wherein the hydrous solvent is a mixture of water and an alcohol selected from the group consisting of methanol, ethanol and isopropanol.

15. The process according to claim 3, wherein the hydrous solvent is a mixture of water and an alcohol selected from the group consisting of methanol, ethanol and isopropanol.

16. The process according to claim 6, wherein the hydrous solvent is a mixture of water and an alcohol selected from the group consisting of methanol, ethanol and isopropanol.

17. The process according to claim 8, wherein the hydrous solvent is a mixture of water and an alcohol selected from the group consisting of methanol, ethanol and isopropanol.

* * * * *

UNITED STATES PATENT AND TRADEMARK OFFICE
CERTIFICATE OF CORRECTION

PATENT NO. : 10,131,665 B2
APPLICATION NO. : 15/027956
DATED : November 20, 2018
INVENTOR(S) : Takao Abe et al.

It is certified that error appears in the above-identified patent and that said Letters Patent is hereby corrected as shown below:

In the Specification

Column 4, Line 61, delete "position)." and insert --position),--.

Column 10, Line 30, delete "above" and insert --above)--.

Column 12, Line 14, delete "dorinenem," and insert --doripenem,--.

Column 14, Line 31, delete "flomoxef" and insert --flomoxef,--.

Column 17, Line 38, delete "0.1" and insert --0.1%--.

Column 20, Line 43, delete "(Boc)group." and insert --(Boc) group.--.

Column 22, Line 38, delete "carbamate," and insert --carbamate;--.

Column 22, Line 63, delete "(2 S," and insert --(2S,--.

Column 25, Line 63, delete "becampicillin," and insert --bacampicillin,--.

Column 26, Line 3, delete "cefepim," and insert --cefepime,--.

Column 26, Lines 4 to 5, delete "cefzopran," and insert --cefozopran,--.

Column 26, Line 5, delete "ceftaxime," and insert --cefotaxime,--.

Column 26, Line 5, delete "ceftiam," and insert --cefotiam,--.

Column 26, Line 6, delete "ceftetam," and insert --cefotetan,--.

Signed and Sealed this
Thirtieth Day of April, 2019

Andrei Iancu
*Director of the United States Patent and Trademark Office*

CERTIFICATE OF CORRECTION (continued)
U.S. Pat. No. 10,131,665 B2

Column 26, Line 7, delete "cefnicid," and insert --cefonicid,--.

Column 26, Line 8, delete "cefperazone," and insert --cefoperazone,--.

Column 26, Line 22, delete "carbepenem," and insert --carbapenem,--.

Column 26, Lines 46 to 47, delete "carbepenems," and insert --carbapenems,--.

Column 30, Line 61, delete "ring" and insert --drying--.

Column 39, Line 10, delete "1.15" and insert --11.4--.

Column 40, Line 33, delete "ted-" and insert --tert- --.

Column 42, Line 21, delete "mu" and insert --mg--.

Column 42, Line 26, delete "[M-H]+" and insert --[M-H]- --.

Column 42, Line 31, delete "[3.4.1]" and insert --"[3.2.1]"--.

Column 48, Line 19, delete "(2 S," and insert --(2S,--.

Column 48, Line 20, after "-carboxamide" insert --(VII-7)--.

Column 50, Line 65, delete "(br.d." and insert --(br.d.,--.

Column 55, Line 6, delete "211);" and insert --2H);--.

Column 55, Line 55, delete "-3a4," and insert -- -3a,4,--.

Column 56, Line 43, delete "(2H-" and insert --(2H-)--.

Column 58, Line 26, delete "(70" and insert --(70 mL),--.

Column 58, Line 34, delete "(d," and insert --(d, J=--.

Column 66, Line 18, delete "Latticer" and insert --Lattice--.

Column 67, Line 63, delete "endothemilc" and insert --endothermic--.

Column 69, Line 51, delete "21.50" and insert --22.50--.

Column 70, Line 5, after "to" insert --pH--.

Column 74, Line 27, delete "5.10" and insert --5.20--.

Column 75, Line 3, delete "89%)," and insert --89%).--.
In the Claims
Column 79, Lines 21 to 29, Claim 2, Lines 5 to 13, delete " 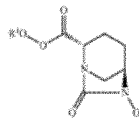 " and insert
-- 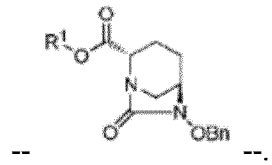 --.
Column 81, Line 12, Claim 4, Line 33, delete "is is" and insert --is--.